US008594848B2

(12) United States Patent
Ludwig

(10) Patent No.: US 8,594,848 B2
(45) Date of Patent: Nov. 26, 2013

(54) RECONFIGURABLE CHEMICAL PROCESS SYSTEMS

(75) Inventor: Lester F. Ludwig, Redwood Shores, CA (US)

(73) Assignee: Lester F. Ludwig, Belmont, CA (US)

(*) Notice: Subject to any disclaimer, the term of this patent is extended or adjusted under 35 U.S.C. 154(b) by 1195 days.

(21) Appl. No.: 11/946,678

(22) Filed: Nov. 28, 2007

(65) Prior Publication Data
US 2008/0069739 A1 Mar. 20, 2008

Related U.S. Application Data

(60) Provisional application No. 60/861,660, filed on Nov. 28, 2006.

(51) Int. Cl.
*B01J 19/00* (2006.01)

(52) U.S. Cl.
USPC ............... 700/266; 700/268; 702/22; 702/31; 702/32; 422/3; 422/62; 422/105; 422/114; 422/115; 435/3; 436/55

(58) Field of Classification Search
USPC ............... 422/3, 62, 105–116; 435/3; 436/55; 700/266, 268; 702/22, 31, 32
See application file for complete search history.

(56) References Cited

U.S. PATENT DOCUMENTS

| 5,606,950 | A | * | 3/1997 | Fujiwara et al. ............ 123/399 |
| 6,415,384 | B1 | | 7/2002 | Dave | |
| 2008/0223721 | A1 | | 9/2008 | Cohen et al. | |
| 2009/0121476 | A1 | | 5/2009 | Malito et al. | |

OTHER PUBLICATIONS

Fluidic Valves for Variable-Configuration Gas Treatment, V.Tesar, Institution of Chemical Engineers, Trans IChemE, Part A, Sep. 2005, Chemical Engineering Research and Design, 83(A9): 1111-1121, available at http://eprints.whiterose.ac.uk/758/1/tesary6.pdf.
Development of a Microfluidic Unit for Sequencing Fluid Samples for Composition Analysis, V. Tesar*, J. R. Tippetts, Y. Y. LOWand R. W. K. Allen, Institution of Chemical Engineers, Trans IChemE, Part A, Jun. 2004, Chemical Engineering Research and Design, 82(A6): 708-718, available at http://eprints.whiterose.ac.uk/468/1/tesarv2.pdf.
Sampling by Fluidics and Microfluidics, V. Tesař, Acta Polytechnica vol. 42 No. 2/2002.

(Continued)

*Primary Examiner* — Brian R Gordon
*Assistant Examiner* — Shogo Sasaki
(74) *Attorney, Agent, or Firm* — Procopio, Cory, Hargreaves & Savitch LLP

(57) ABSTRACT

Systems and methods for software-reconfigurable chemical process systems useful in a wide range of applications. Embodiments may include software control of internal processes, automated provisions for cleaning internal elements with solvents, provisions for clearing and drying gasses, and multitasking operation. In one family of embodiments, a flexible software-reconfigurable multipurpose reusable "Lab-on-a-Chip" or "embedded chemical processor" is realized that can facilitate a wide range of applications, instruments, and appliances. Through use of a general architecture, a single design can be economically manufactured in large scale and readily adapted to diverse specialized applications. Clearing and cleaning provisions may be used to facilitate reuse of the device, or may be used for decontamination prior to recycling or non-reclaimed disposal. In other embodiments, a flexible software-reconfigurable multipurpose reusable laboratory glassware setup may be realized, sparing talented laboratory staff from repetitive, complex, or low-level tasks occurring in analysis, synthesis, or small-scale chemical manufacturing.

20 Claims, 63 Drawing Sheets

(56) References Cited

OTHER PUBLICATIONS

Lectures on Chemical Reaction Networks: Introduction, Martin Feinberg, 1979, available at http://www.che.eng.ohio-state.edu/~feinberg/LecturesOnReactionNetworks/images/FeinbergLecture1.pdf, accessed on Jun. 12, 2006.
Lectures 2: Reaction Networks, Kinetics, and the Induced Differential Equations, Martin Feinberg, 1979, available at http://www.che.eng.ohio-state.edu/~feinberg/LecturesOnReactionNetworks/images/FeinbergLecture2.pdf, accessed on Jun. 12, 2006.
Lectures 3: Two Theorems, Martin Feinberg, 1979, available at http://www.che.eng.ohio-state.edu/~feinberg/LecturesOnReactionNetworks/images/FeinbergLecture3.pdf, accessed on Jun. 12, 2006.
Lectures 4: Some Definitions and Propositions, Martin Feinberg, 1979, available at http://www.che.eng.ohio-state.edu/~feinberg/LecturesOnReactionNetworks/images/FeinbergLecture4.pdf, accessed on Jun. 12, 2006.
Lectures 5: Proof of the Deficiency Zero Theorem, Martin Feinberg, 1979, available at http://www.che.eng.ohio-state.edu/~feinberg/LecturesOnReactionNetworks/images/FeinbergLecture5.pdf, accessed on Jun. 12, 2006.
A Toy Model of Chemical Reaction Networks, Gil Benko, Nov. 2002, available at http://www.tbi.univie.ac.at/papers/Abstracts/gil_dipl.pdf.
Development of a MEMS Microvalve Array for Fluid Flow Control, Nelsimar Vandelli, Donald Wroblewski, Margo Velonis, and Thomas Bifano, Journal of Microelectromechanical Systems, Vol. 7, No. 4, December 1998, available at http://sws1.bu.edu/bifano/PDF_files/23_Flow.pdf.
The Chemical Reaction Network Toolbox: Downloads and Instructions, Martin Feinberg, available at http://www.chbmeng.ohio-state.edu/~feinberg/cmt/, accessed on Jun. 12, 2006.
Device could convert waste heat into electricity, Elizabeth A. Thomson, MIT Tech Talk, Dec. 5, 2001, available at http://web.mit.edu/newsoffice/2001/electricity-1205.html, accessed on Jun. 12, 2006.
Development of a Rapid-Response Flow-Control System Using MEMS Microvalve Arrays, John Collier, Donald Wroblewski, and Thomas Bifano, Journal of Microelectromechanical Systems, vol. 13, No. 6, Dec. 2004, available at http://128.197.153.21/tgb/PDF_filesNalves.pdf.
A Novel Pressure Balanced Microfluidic Valve, J. M. Quero, A. Luque, L. G. Franquelo, Proc. ISCAS May 26-29, 2002, available at http://woody.us.es/~aluque/doc/pressure_balanced_microvalve.pdf.
Fabrication of Polysilicon Micro Valve Array, Jermaine White, 22rd Annual Microelectronic Engineering Conference, May 2004, available at http://www.rit.edu/~ue/ameccontent/17_JWhite.pdf.
Parker R-max™ Stream Switching System, Parker Instrumentation, Catalog 4140-R, Revised, Jun. 2002, available at http://www.plesneras/mod/products/upload/4140-R.pdf.
Fast Switching Valves: Ultra Fast and Highly Repeatable, FESTO Corp, Info 96 207 US, Jun. 2005, available at http://www.zycon.com/Literature/219948/75280/Info207_FastSwitchingV.pdf.
Electric Power Generated from Waste Heat, Translation of the AIST press released on May 31, 2005, available at http://www.aistgo.jp/aist_e/latest_research/2005/20050617/20050617.html, accessed on Jun. 12, 2006.
Flow Selection Valves: Series 105T Valve, Bio-Chem Fluidics, 2010, available at https://www.biochemfluidics.com/cart/store/comersus_listOneCategory.asp?idCategory=393, accessed on Jun. 12, 2006.
Flow Selection Valves: Series 080T Valve, Bio-Chem Fluidics, 2010, available at https://www.biochemfluidics.com/cart/store/comersus_listOneCategory.asp?idCategory=392, accessed on Jun. 12, 2006.
Cheminert® Valves for Flow Injection Analysis, FIAlab Instruments, 2010, available at http://www.flowinjection.com/valves.html, accessed on Jun. 12, 2006.
solenoid valves and eletric valve, Peter Paul Electronics Co., Inc., 2010, available at http://www.peterpaul.com/whats_new_display2.php4?cat_id=6, accessed on Jun. 12, 2006.
Gems Predyne Pneumatic Solenoid Valves & Miniature Solenoid Valves: general-purpose-valves, Gems Sensors & Controls, 2010, available at http://www.gemssensors.com/Search.aspx?q=general-purpose-valves, accessed on Jun. 12, 2006.
Gems Predyne Pneumatic Solenoid Valves & Miniature Solenoid Valves: isolation-valves, Gems Sensors & Controls, 2010, available at http://www.gemssensors.com/Search.aspx?q=isolation-valves, accessed on Jun. 12, 2006.
1200 Series Valve Solutions, Agilent Technologies, 2000-2010, available at http://www.chem.agilent.com/en-us/products/instruments/lc/1200seriesvalvesolutions/pages/defaultaspx, accessed on Jun. 12, 2006.
Valve matrix takes squeeze out of juice production, Prepared Foods, Oct., 1997, available at http://findarticles.com/p/articles/mi_m3289/is_n11_v166/ai_20224164/, accessed on Jun. 12, 2006.
Valve Matrix Operating Instructions, GEA Process Equipment Division, 2003, available at http://www.tuchenhagen.com/tuchenhagen/cmsdoc.nsf/webdoc/ndkw73galz.
Solenoid Valve Manifolds, Precision Dynamics, 2004, exercised on Jun. 12, 2006 at http://www.predyne.com/manifols.html, accessed on Jun. 12, 2006.
AquaCore: A Programmable Architecture for Microfluidics, Ahmed M. Amin, Mithuna Thottethodi, T. N. Vijaykumar Steven Wereley=, and Stephen C. Jacobson,, 2007, available at https://engineering.purdue.edu/ploc/publications/isca07.pdf.
Unified High-Level Synthesis and Module Placement for Defect-Tolerant Microfluidic Biochips*. Fei Su and Krishnendu Chakrabarty, 2005, available at http://people.ee.duke.edu/~krish/p825.pdf.
Architectural-Level Synthesis of Digital Microfluidics-Based Biochips, Fei Su and Krishnendu Chakrabarty, Published in Proc. IEEE International Conference on CAD, pp. 223-228, 2004, available at http://www.sigda.org/daforum/abs/44_attachment.pdf.
A Scheduling and Routing Algorithm for Digital Microfluidic. Ring Layouts with Bus-phase Addressing. Megha Gupta and Srinivas Akella, available at http://robotics.usc.edu/~megha/IROSfinalsubmit.pdf.
Digital microfluidics: is a true lab-on-a-chip possible?, Microfluidics and Nanofluidics, vol. 3, No. 3 / Jun. 2007.
Digital microfluidic design and optimization of classic and new fluidic functions for lab on a chip systems, Microfluidics and Nanofluidics, vol. 4, No. 3 / Mar. 2008.
Arrays for Digital Signal Processing Functions: Fault Tolerance and Functional Reconfiguration, A. Antola, R. Negrini, M.G. Sami and N. Scarabottolo, Reconfigurable Massively Parallel Computers, Hungwen Li and Quentin F. Stout, pp. 170-222, 1991.
Motivation: Mission-critical Computing, Problems and Solutions, Svetlana P. Kartashev and Steven I. Kartashev, Designing and Programming Modern Computer Systems: Supercomputing Systems : Reconfigurable Architectures, pp. 1-17, 1989.
Nonrobotic Automated Workstations for Solution Phase Synthesis, Laboratory Automation in the Chemical Industries, David G. Cork and Tohru Sugawara, pp. 41-72, 2002.
Heterogeneous System-Level Specification in Systemc, Fernando Herrera, Pablo Sánchez and Eugenio Villar Advances in Design and Specification Languages for SoCs, Pierre Boulet, pp. 199-206, 2006.
Introduction to Reconfigurable Hardware, Nikolaos Voros and Konstantinos Masselos, System Level Design of Reconfigurable Systems-on-Chip, pp. 15-26, 2005.
Design Flow for Reconfigurable Systems-on-Chip, Nikolaos Voros and Konstantinos Masselos, System Level Design of Reconfigurable Systems-on-Chip, pp. 107-131, 2005.
SystemC Based Approach, Yang Qu and Kari Tiensyrja, System Level Design of Reconfigurable Systems-on-Chip, pp. 107-131, 2005.
Synthesis of Multiplexed Biofluidic Microchips, Anton Pfeiffer, Tamal Mukherjee and Steinar Hauan, Design Automation Methods and Tools for Microfluidics-Based Biochips, pp. 271-300, 2006.
Modeling and Controlling Parallel Tasks in Droplet-Based Microfluidic Systems, Karl Bohringer, Design Automation Methods and Tools for Microfluidics-Based Biochips, pp. 301-327, 2006.
Performance Characterization of a Reconfigurable Planar Array Digital Microfluidic System, Eric Griffth, Srinivas Akella and Mark Goldberg, Design Automation Methods and Tools for Microfluidics-Based Biochips, pp. 329-356, 2006.

* cited by examiner

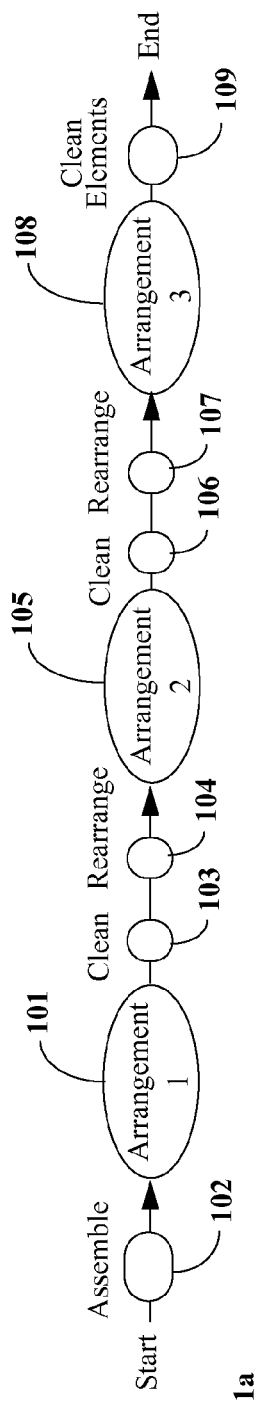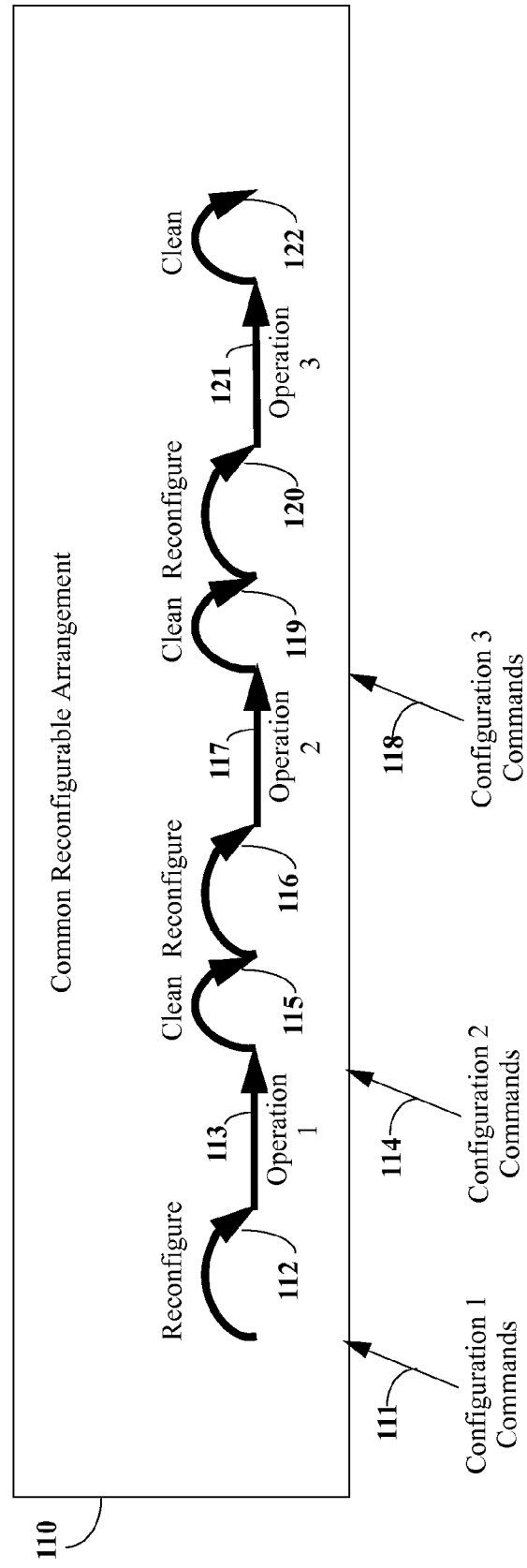

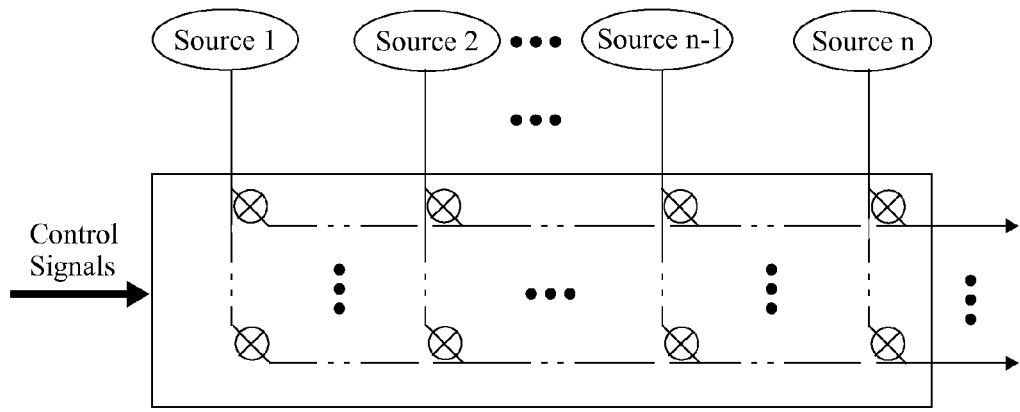
Figure 11a  A Lattice/Matrix Valve Complex of Simple On/Off Valves
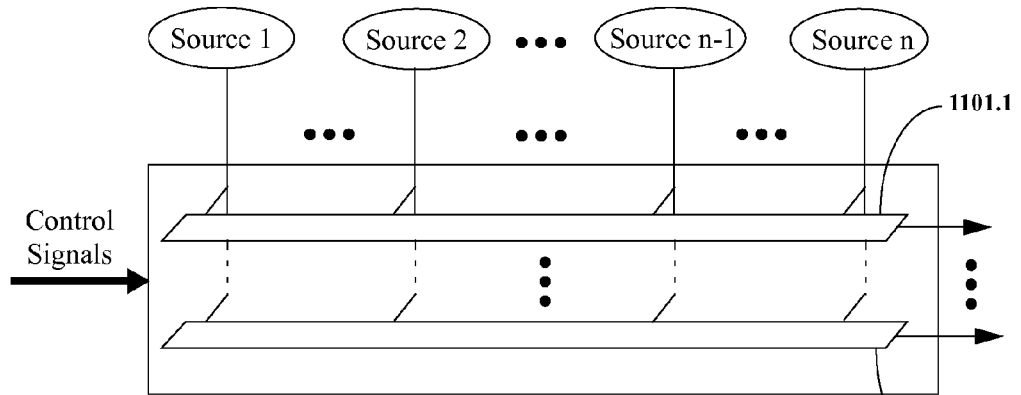
Figure 11b  A Lattice/Matrix Valve Complex of Multi-Port Valves
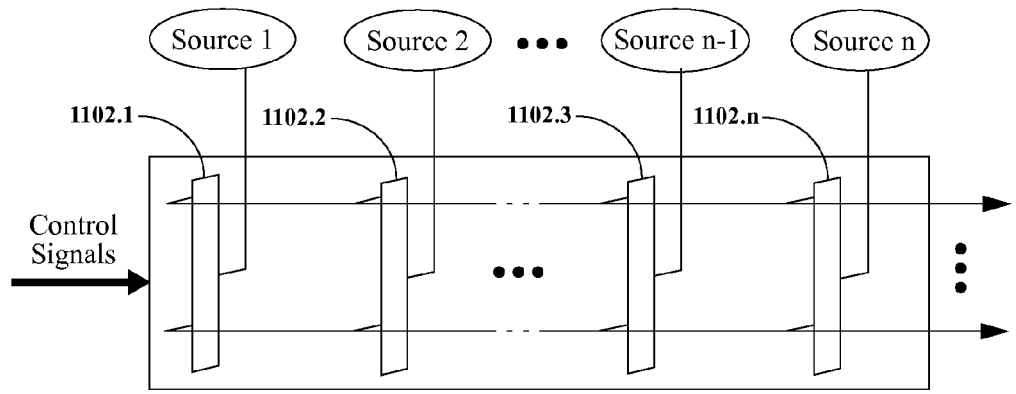
Figure 11c  Another Lattice/Matrix Valve Complex of Multi-Port Valves A Lattice/Matrix Valve Complex of Multi-Port Valves Another Lattice/Matrix Valve Complex of Multi-Port Valves

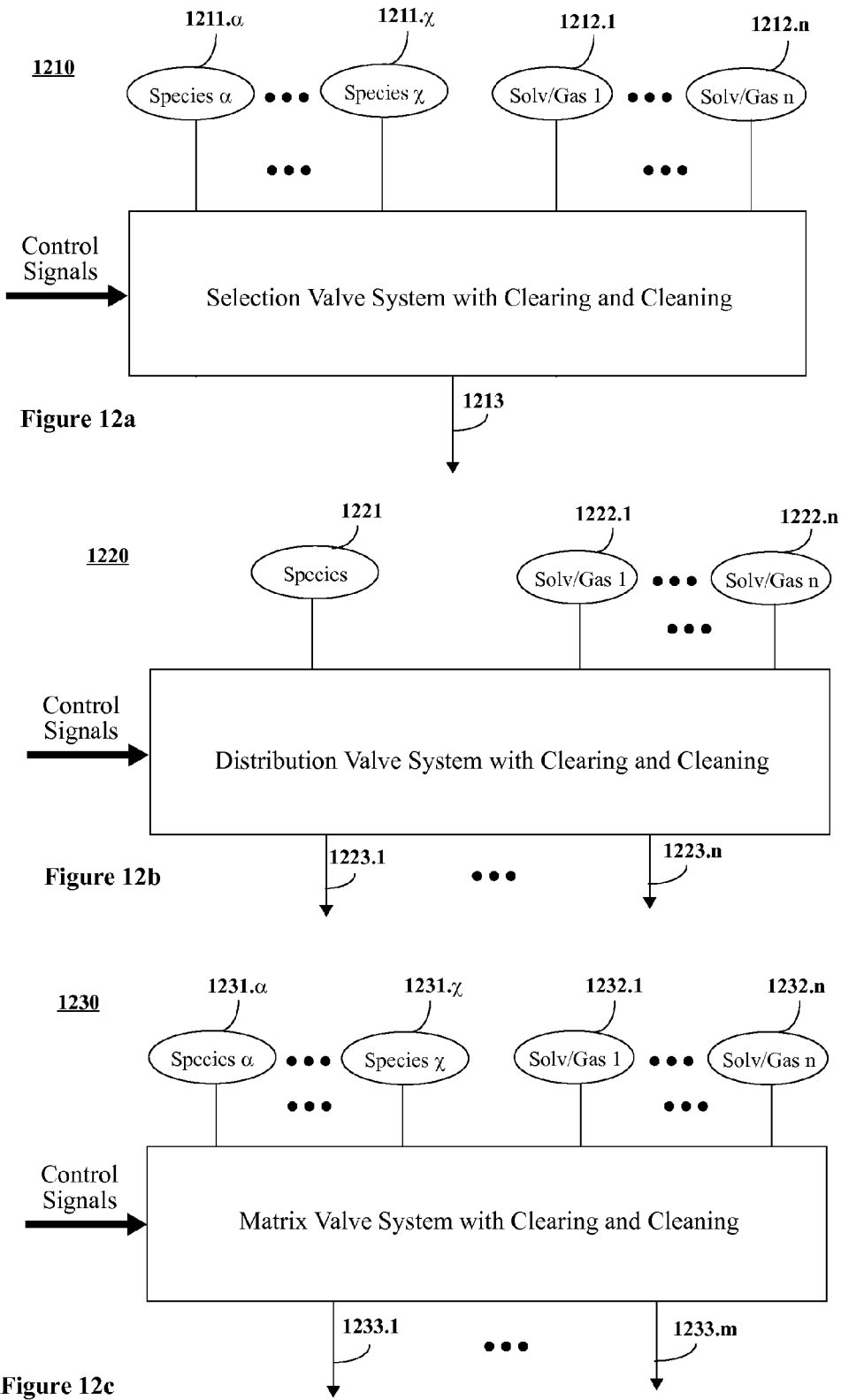

RECONFIGURABLE CHEMICAL PROCESS SYSTEMS

CROSS REFERENCE TO RELATED APPLICATIONS

Pursuant to 35 U.S.C. §119(e), this application claims benefit of priority from provisional patent application Ser. No. 60/861,660, filed Nov. 28, 2006, the contents of which are hereby incorporated by reference herein in their entirety.

BACKGROUND OF THE INVENTION

1. Field of the Invention

The invention relates generally to the structure and control of reconfigurable chemical reaction environments, and as such is applicable to micro-scale hybrid-process "chips," "lab-on-a-chip," multiple "lab-chip" systems, field-scale chemical instrumentation, laboratory-scale instruments and devices, chemical production plants, controlled catalytically-activated systems, enzyme networks, and various types of exogenously-activated (optical, electric field, thermal) chemical reaction systems.

2. Discussion of the Related Art

Processes, procedures, and equipment for commercial chemical production and experimental laboratory activities have a rich history and one of extensive continued development. In these, standard components (tanks, reaction chambers, flow reactors, dryers, piping, stirrers, cracking towers, and so forth in chemical plants; flasks, condensers, tubing, drying tubes, stirrers, bubbles, heating mantles and so forth in chemical laboratories) are configured in various ways to create environments for controlled chemical processes. In some applications, these standardized components are configured into a fixed arrangement that, subject to repairs, remains intact for the duration of the lifetime of the standardized component. In other applications, the standardized components may be assembled into first one configuration, then dismantled, cleaned, assembled into a second configuration, and so forth, thus hosting a variety of chemical reaction environments over the standardized component lifetimes. In a few selected applications, one or more standardized components may be assembled in mildly flexible arrangements, for example, a reaction vessel port may be connected by a "T-valve" to two alternative tanks, etc. However, in chemical plant and laboratory environments, such minor reconfiguration capabilities are rare, localized, and non-systemic.

In more recent times, automated specialized field and laboratory instruments have emerged for performing specialized tasks such as gas spectroscopy, electrophoresis, chromatography, and specialized segments of analytical chemistry. Such systems, especially more contemporary ones, often involve computer control of valves, pumps, heating elements, electric-field-inducing electrodes, etc. Although reconfiguration capabilities may be present in such systems, the range of possible configurations is again relatively limited and the overall resulting systems are suitable only for specific specialized tasks.

In recent years, the notion of "lab-on-a-chip" technology has emerged and shown considerable promise. Incorporating photolithography techniques perfected in semiconductor fabrication, ink jet technology, micro-fluidic and capillary hydrodynamics, micro-electromechanical system (MEMS) technologies, nano-scale processes, and other technologies and techniques, it is envisioned that miniature "instruments" or "laboratories" on the scale of microprocessor chips can be cost-effectively manufactured. In the currently accepted view, each such miniature laboratory would have a specific design exclusively dedicated to highly specified tasks, such as those relating to sample evaluation, matrix-array DNA sequencing, etc.

Each of the aforementioned environments, although involving various degrees of automation, are either dedicated to specific configurations and applications, or are flexibly reconfigurable only by extensive human intervention and handling. In the most flexible of these environments—i.e., the experimental chemical laboratory—individual glassware elements and associated devices are assembled in a configuration, used in that configuration, retrieved after the configuration is dismantled, cleaned, stored in inventory, retrieved from inventory, assembled into another configuration, etc.

SUMMARY OF THE INVENTION

In one aspect, a flexible software-reconfigurable multipurpose reusable "Lab-on-a-Chip" is realized. In another aspect, a flexible software-reconfigurable multipurpose reusable laboratory glassware setup is realized.

BRIEF DESCRIPTION OF THE DRAWINGS

The above and other aspects, features, and advantages of the present invention will become more apparent upon consideration of the following description of preferred embodiments, taken in conjunction with the accompanying drawing figures, wherein:

FIG. 1a depicts a sequence implemented in a laboratory or chemical production plant setting;

FIG. 1b depicts a sequence utilizing a common reconfigurable arrangement;

FIGS. 2a-2c illustrate further exemplary cases of the situation depicted in FIG. 1a;

FIGS. 11a-11e depict examples of a "matrix-valve" configuration;

FIGS. 12a-12e depict an example sequence of operation for an exemplary arrangement of multiple port valve structures or complexes selecting among a number of chemical species and/or solvent and cleaning gas inflows that are directed to a chemical reaction subsystem and multiple outflow destinations;

FIG. 20 depicts an alternate implementation of the general arrangement of the valve complex depicted in FIG. 16a;

FIG. 22b illustrates a modification of the valve structure of FIG. 22a;

DETAILED DESCRIPTION OF PREFERRED EMBODIMENTS

Figure 2C:
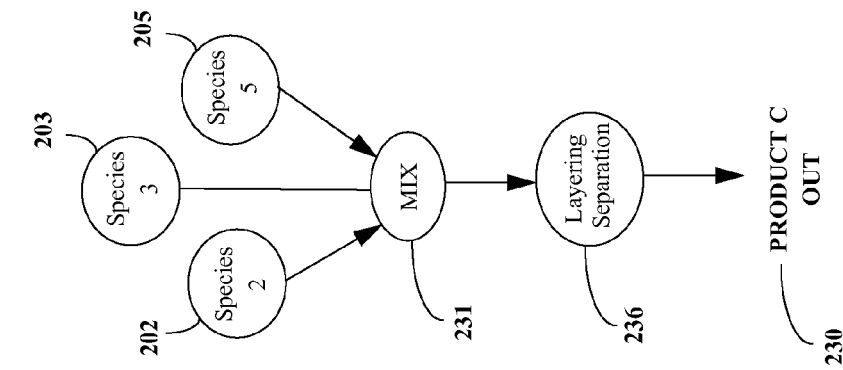

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention.

As each of "lab-on-a-chip," field-scale and laboratory-scale automated instrumentation systems, and economies of chemical plants continue to evolve, there is considerable opportunity for the perfection and incorporation of flexible reconfigurable chemical systems, particularly those that can support a wide range of chemical reaction environments under full or partially automated operation and reorganization.

Through the use of controllable valve subsystems, specific reactants may be selected and routed to reaction chambers whose temperature, pressure, optical properties, and other attributers may be automatically controlled and/or measured. Reaction chambers and transport conduits may be cleaned by pumping appropriate solvents and gases through them. By ganging such valve subsystems and structures together with additional networks of valves and transport conduits, increasingly arbitrary networks of chemical reaction and handling elements may be configured and operated under automated reorganization and control. In some applications, the design may be extended to include mid-transport reagent recovery and solvent recycling, while other applications may employ disposable valve, transport, and reaction elements. Additionally, partitioned subsets of the elements may be reserved for specialized reagents, reagents with divergent properties (viscosity, reactivity, etc.), reagents of frequent use (sample fluids, water or other reaction-supporting fluids, catalyst, indicators, etc.).

Although the approaches described thus far involve conventional chemical process control attributes and actions such as temperature, pressure, mixing, etc., the automated processes can be readily extended to a number of more exotic approaches including optical activation, color sensing, acoustic stimulation, electric field stimulation, flow-induced faraday induction, ferrite agitation, and the like.

Additionally, although the approaches described thus far involve physically separated structures, many of the methods and techniques can be applied to more complex chemical systems where enzyme and/or other selectable activated catalysts are used to invoke, control, and/or regulate isolated chemical reactions in a confluent elixir, substrate gel, intracellular cytoplasm, intercellular fluids, tissue, membrane, etc. As such, various systems and methods discloses herein may be further employed in life-science and biomedical applications. For example, one implementation can be used in simulated or in vitro environments for studying or manipulating biomedical processes within and/or among living cells. Further, although the context of the discussions thus far and in the following are made in terms of chemical species, chemical reactions, and chemical products, and chemical wastes, embodiments of the invention can be directly applied to biosystems and life-sciences applications. In these adaptations:

"Chemical species," "chemical products," and "chemical wastes" would be replaced with more complex substances such as microorganism serums, etc.;

"Chemical reactions" would be replaced with "bioreactions;"

"Chemical system elements" would be replaced with "bioreaction system elements."

One basic theme includes the creation of a controllably-configurable arrangement of elements for performing a wide range of chemical reactions, wherein the arrangement is both relatively fixed and internally comprises one or more controllably-configurable elements. The controllably-configurable elements are typically controlled by computational processes, usually involving electrical control signals produced by a microprocessor or other computer element. Some aspects are not limited to simply arrangements having a single human-operated or computer-operated valve, but rather and in particular are directed toward scale and variations in processes that would otherwise require a rearrangement of elements.

FIGS. 1a and 1b depict this more specifically for a situation involving sequential operation of three chemical production procedures and associated configurations. FIG. 1a depicts how such a sequence may be implemented in a laboratory or chemical production plant setting where at least some of the equipment (and possibly chemical species/reagents) are involved in more than one of the procedures. To begin, a first arrangement 101 of chemical equipment and chemical species/reagents is assembled 102, and the first procedure is performed. The equipment arrangement is then likely to be at least partially dismantled and cleaned 103. The cleaned equipment is then reassembled 104, possibly including at least some new equipment elements and not including other previously used equipment elements, to form a second arrangement 105 for use with at least some previously unemployed chemical species/reagents. The equipment arrangement is then likely to be at least partially dismantled and cleaned 106. The cleaned equipment is then reassembled 107, possibly including at least some new equipment elements and not including other previously used equipment elements, so as to form a third arrangement 108 for use with at least some previously unemployed chemical species/reagents. The equipment arrangement is then likely to be at least partially dismantled and cleaned 109.

FIG. 1b depicts how such a sequence might be done utilizing a common reconfigurable arrangement 110 provided for by the present invention. To begin, a first one or more configuration command(s) 111 are directed to common reconfigurable arrangement 110, causing a first arrangement of chemical equipment and chemical species/reagents to be internally configured 112, and the first operation is performed 113. A second one or more configuration command(s) 114 are directed to common reconfigurable arrangement 110, causing the equipment arrangement to be cleaned 115 and then internally reconfigured 116 to form a second arrangement, and the second operation is performed 117. A third one or more configuration command(s) 118 are directed to the common reconfigurable arrangement 110, causing the equipment arrangement to be cleaned 119 and then internally reconfigured 120 to form a third arrangement, and the third operation is performed 121. The equipment arrangement is then likely cleaned 122.

Figure 2B:
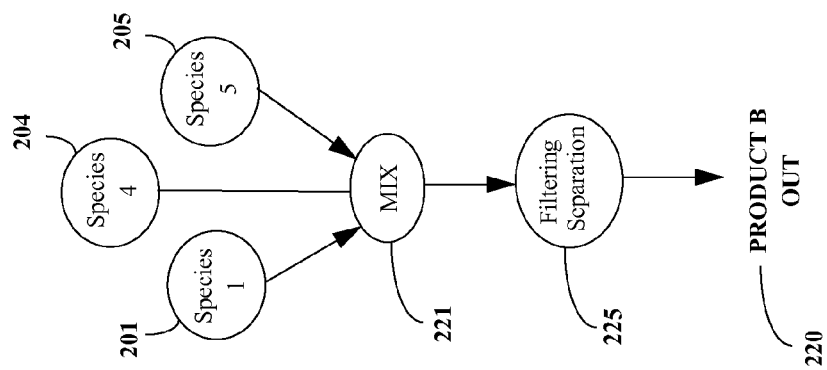
Figure 2A:
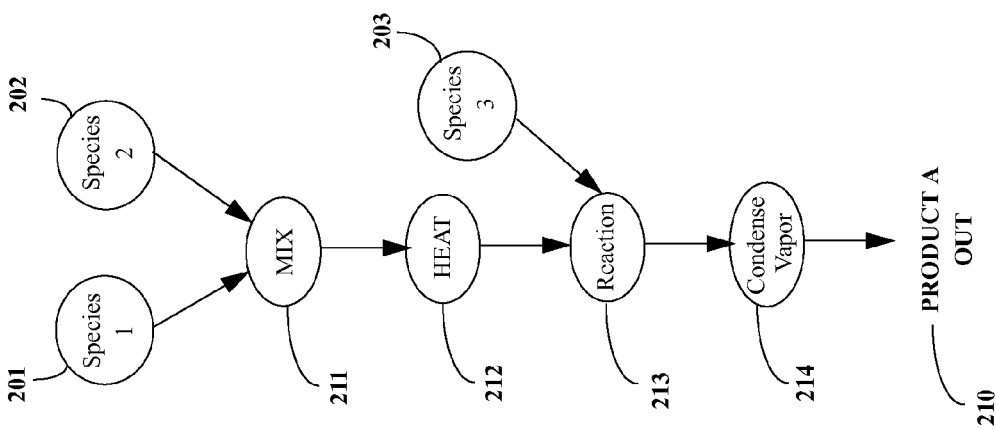

FIGS. 2a-2c illustrate further more specific exemplary cases of the situation depicted in FIG. 1a:

In the process illustrated in FIG. 2a, Species 1 201 and Species 2 202 are mixed 211, heated 212, and subsequently combined with Species 3 203 in a reaction chamber 213. The reaction produces a heated vapor for an interval of time which is then condensed 214 using a cooling operation to yield output Product A 210.

In the process illustrated in FIG. 2b, Species 1 201 is mixed 221 together with Species 4 204 and Species 5 205, and the mixture is then directed to a filtering separation process 225 to yield output Product B 220.

In the process illustrated in FIG. 2c, Species 2 202 is mixed 231 together with Species 3 203 and Species 5 205, and the mixture is then directed to a fluidic layering separation process 236 to yield output Product C 230.

Figure 3A:
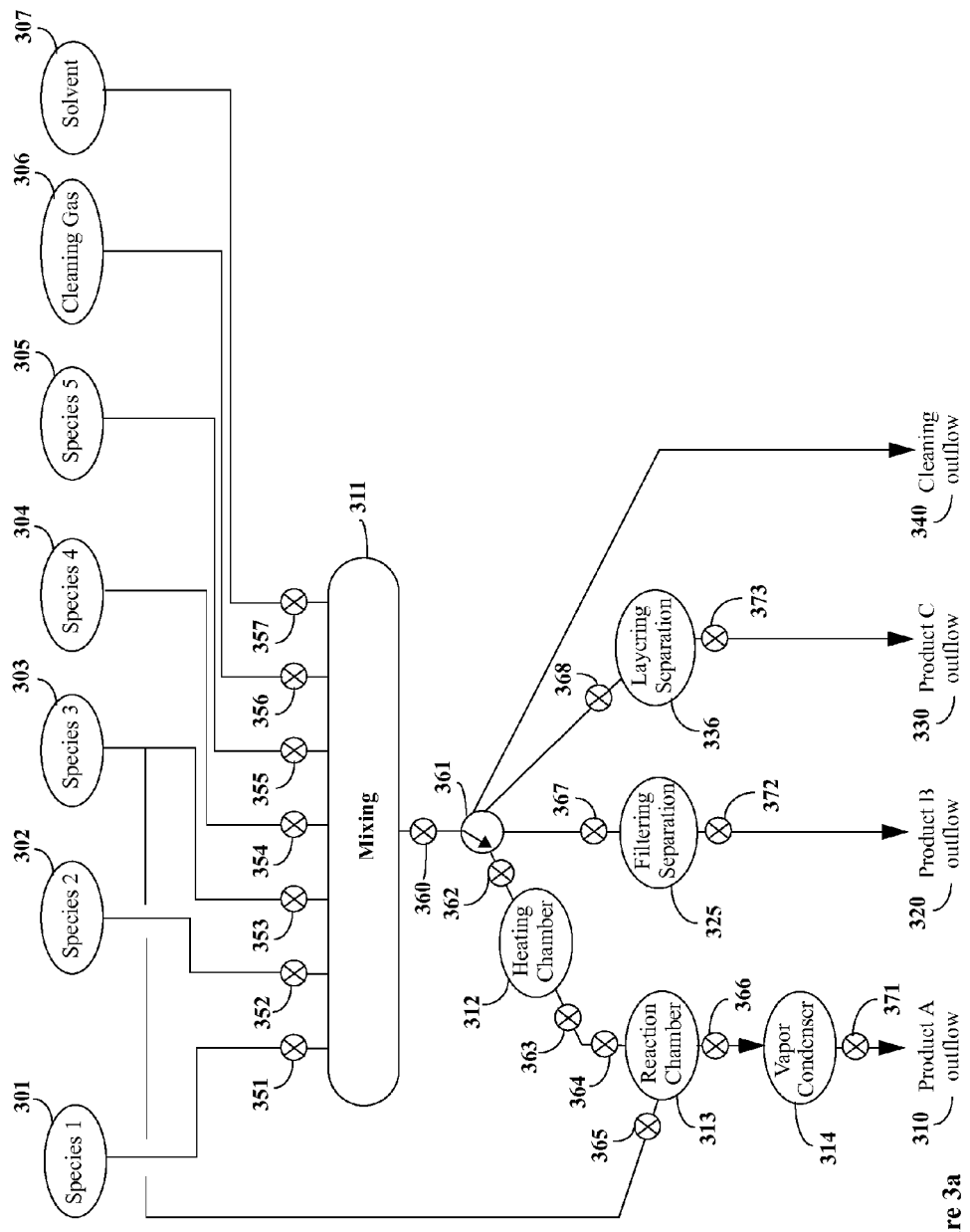
FIG. 3a illustrates an exemplary embodiment of a common reconfigurable arrangement of FIG. 1b.

FIG. 3a illustrates an exemplary embodiment of a common reconfigurable arrangement 110 of FIG. 1b, which can be controlled, in the manner depicted in FIG. 1b, for example, to sequentially perform the chemical procedures of FIGS. 2a-2c. As will be seen, one element in creating this common reconfigurable arrangement 110 is the incorporation of controllable valves. Although one skilled in the art will appreciate that many variations are possible, in this example a common mixing element 311 is fitted with a number of controllable on/off valves 351-357 that selectively permit isolated controlled flows of each of the five Species 301-305 as well as a cleaning-gas 306 and solvent 307 into the common mixing element 311. The embodiment of FIG. 3a additionally comprises an outflow gating valve 360 and a mutually-exclusive four-output distribution valve 361 to direct the mixing element's contents to one of four destinations:

a heating chamber 312, reaction chamber 313, and vapor condenser 314 in tandem,
a filtering separation element 325,
a layering separation element 336,
a cleaning-gas solvent outflow path 340.

Heating chamber 312 is shown having on/off isolating inlet gating valve 362 and outlet gating valve 363. Similarly, reaction chamber 313 includes on/off isolating inlet gating valves 364, 365 and outlet gating valve 363. In alternate implementations, the function of the heating chamber 312 may be integrated into the mixing element 311 and/or the reaction chamber 313. Of these, it is noted that heating done at the mixing element 311 can increase the required complexity for backflow and vapor isolation among the species feeds.

Referring still to FIG. 3a, the filtering separation element 325 is provided with on/off isolating inlet gating valve 367 and on/off outlet gating valve 372. Similarly, the layering separation element 336 is provided with on/off isolating inlet gating valve 368 and on/off outlet gating valve 373. The embodiment of FIG. 3a provides for the reaction chamber outlet valve 366 to connect directly to the vapor condensing element 314. In alternate embodiments additional flow isolation valves and coolant control valves may be added to assist operation of the vapor condenser 314. The vapor condenser 314 is shown with an on/off outlet gating valve 371, which in the exemplary configuration of FIG. 3a, subsequently controls the outflow of output Product A 310. In alternative embodiments, additional routing and storage elements may be provided. Similarly, the configuration of FIG. 3a depicts the on/off outlet gating valve 372 of the filtering separation element 325 controlling the outflow of output Product B 320. In alternative embodiments, additional routing and storage elements may be provided. Similarly, the exemplary configuration of FIG. 3a depicts the on/off outlet gating valve 373 of the layering separation element 336 controlling the outflow of output Product C 330. In alternative embodiments, additional routing and storage elements may be provided.

Vignettes of exemplary operation of the embodiment of FIG. 3a will now be described. In a first production modality, directed towards the production of output Product A 310, inlet valves 351 and 352 are operated to allow measured amounts of Species 1 301 and Species 2 302 to be directed to the mixing element 311. During or after mixing, control signal instruct the mutually-exclusive four-output distribution valve 361 to later direct the mixing element's contents to heating chamber 312. After mixing, the mixing element outlet valve 363 and heating chamber inlet valve 362 open in some temporal arrangement so that the contents of the mixing element 311 are directed to the heating chamber 312. At least the heating chamber inlet valve 362 may close during heating. After sufficient heating, the heating chamber outlet valve 363 and a first reaction chamber inlet valve 364 open in some temporal arrangement so that the contents of the heating chamber 312 are directed to the reaction chamber 313. Prior, simultaneous, or subsequent to this action, the second reaction chamber inlet valve 365 opens to allow inflow of a measured amount of Species 3 303 into the reaction chamber 313. During the earliest moments of the resulting chemical reaction, it is likely that at least these two inlet valves 364 and 365 are closed to permit build up of vapor pressure. At an appropriate point in the chemical reaction (which may be monitored by sensors, timers, etc.), the reaction chamber outlet valve 366 opens to allow heated vapor flow to the vapor condensing element 314 and opening the vapor condenser outlet valve 371 at the appropriate time to yield an outflow of output Product A 310.

At some point before or after the conclusion of the process for Product A 310, an associated cleaning phase begins. This may be treated as part of the first modality or executed as a function of a transition to a second production modality. Although a wide range of possible approaches is apparent to one skilled in the art, examples are provided here to serve as conceptual high-level illustrations.

In a first exemplary cleaning procedure aspect, control signals instruct the mutually-exclusive four-output distribution valve 361 to direct the mixing element's contents to the cleaning outflow path 340. The mixing element outlet valve 360 and mixing element cleaning-gas inlet valve 356 open in some temporal arrangement so that the cleaning-gas can blow (and/or evaporate) at least some remaining fluids and gasses out of the mixing element 311, outlet gate valve 360, and associated pathway conduits. This action of using a cleaning-gas to blow (and/or evaporate) at least some remaining fluids and gasses out of various previously used elements will be termed "clearing." It is noted that in some situations such gas-oriented clearing may not be appropriate due to possible precipitant formation, resulting dangerous conditions, reactions with the particular type of cleaning-gas, and the like.

Next, in this first exemplary cleaning procedure aspect, the mixing element cleaning-gas inlet valve 356 and/or mixing element outlet valve 360 may remain open or closed, and the mixing element solvent inlet valve 357 opens to allow solvent to enter the mixing element 311. By various approaches (such as outlet valve 360 operation, accelerated solvent inflow, solvent inlet directional design, internal agitation, etc.) the entire mixing element 311 is washed, including the inlet vestibules from the chemical species inlet valves 351-355. The laden solvent wash is then purged through the mixing element outlet valve 360, mutually-exclusive four-output distribution valve 361, and associated pathway conduits to direct the mixing element's contents to the cleaning outflow path 340. Then the cleaning-gas is blown through this same path to evaporate the remaining solvent. It may be advantageous to heat the cleaning-gas, the solvent, and/or various element surfaces to facilitate solvent action and evaporation. In some situations, measured use of cleaning-gas may be used to provide pressure to transport fluids from one entity or location to another.

Note that this first exemplary cleaning procedure aspect may, in principle, begin substantially immediately after the contents of the mixing element 311 is transferred to the heating chamber 312, and thus may occur in parallel with the remainder of the operations of the first production modality (heating, reaction with Species 3, vapor condensation, and the like).

In a second exemplary cleaning procedure aspect—applicable after the conclusion of Product A production—control signals instruct the mutually-exclusive four-output distribution valve 361 to direct the mixing element's contents to the tandem of the heating chamber 312, reaction chamber 313, vapor condenser 314, and associated pathways so as to clear, wash, purge, and evaporate solvent from these elements, associated valves, and associated pathways. Additional solvent and cleaning-gas inlets may be provided to the heating chamber 312, reaction chamber 313, vapor condenser 314, and associated pathways as may prove useful or essential in various embodiments. Additional cleaning outflow routing may also be provided, as in the exemplary variations shown in FIG. 3b. Here the on/off gating valves 371-373 are followed by intervening mutually-exclusive two-output distribution valves 381-383. For each of these intervening two-output distribution valves 381-383, one of the two outputs is directed to the respective product outflows 310, 320, 330) while the second of the two outputs is directed to the cleaning outflow 340.

Figure 3B:
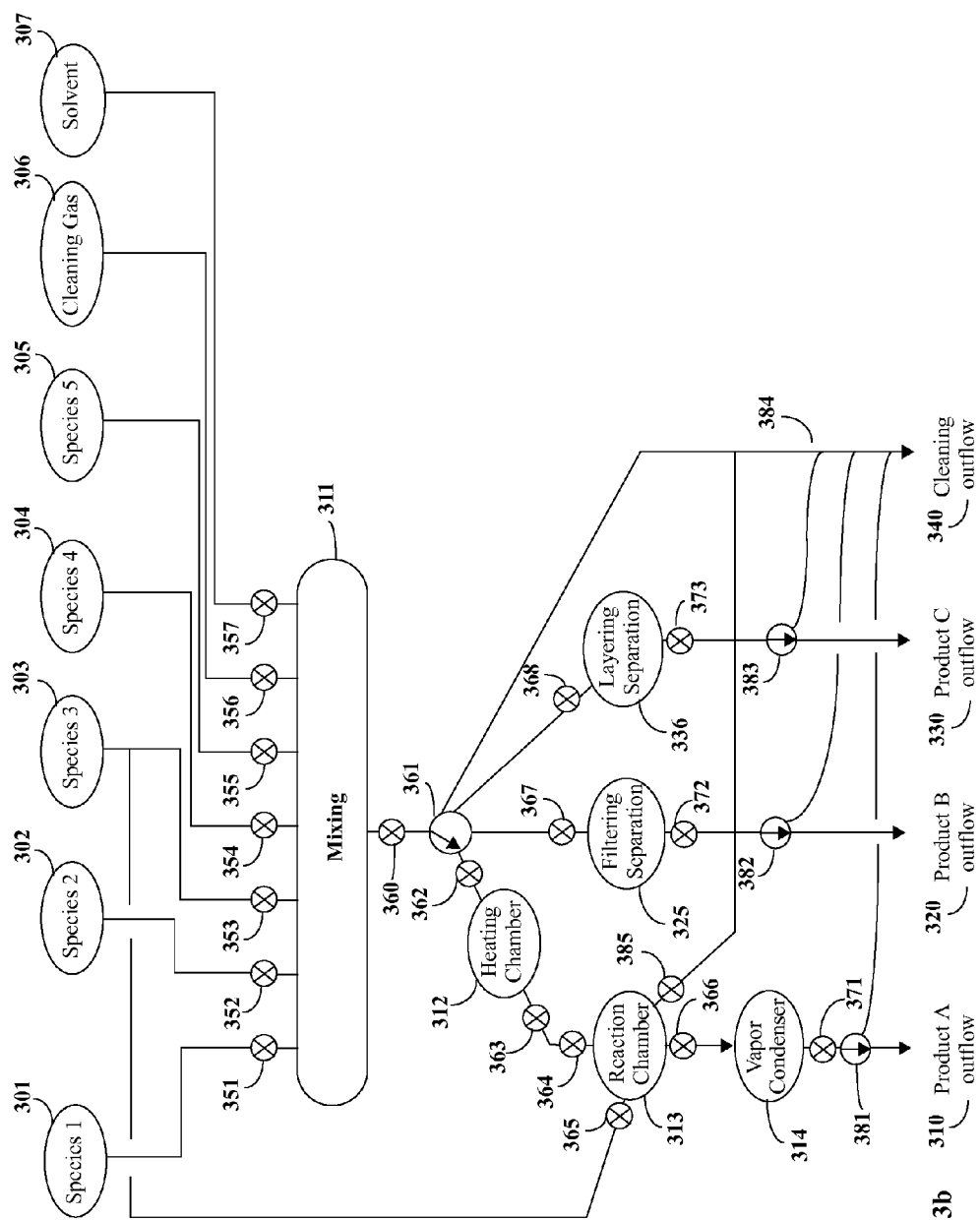
FIG. 3b illustrates additional cleaning outflow routing.

Note that the second exemplary cleaning procedure aspect may, in principle, begin substantially immediately after the conclusion of the outflow of output Product A. This is facilitated if the additional cleaning outflow routing, such as that depicted in FIG. 3b, is provided. If such cleaning outflow routing is provided along with appropriately situated additional solvent and cleaning-gas inlets for the heating chamber 312, reaction chamber 313, and associated pathways, sequenced segments of variations of the second exemplary cleaning procedure aspect may begin in fact prior to the conclusion of the production outflow of Product A 310. For example, the heating chamber 312 may be cleared and cleaned.

In an alternative approach, which merges most of both the first and second exemplary cleaning procedure aspects described above, there may be no use of the cleaning outflow path 340. Rather all flows involving the cleaning of the mixing element 311 are directed through the tandem of the heating chamber 312, reaction chamber 313, vapor condenser 314, and associated pathways so as to clear, wash, purge, and evaporate solvent from each of these elements, associated valves, and associated pathways. Note that in most implementations this approach cannot be initiated until the end, or near the end, of Product A 310 production.

With the conclusion of the clearing and cleaning of at least the mixing element 311, outlet gate valve 360, control signals instruct the mutually-exclusive four-output distribution valve 361, and associated pathway conduits (i.e., what amounts to, or may accomplish the same effect as the first exemplary cleaning procedure aspect), the exemplary system shown in FIG. 3a and FIG. 3b can then begin the production of Product B 320. One exemplary realization of this is described next.

In a second production modality, directed towards the production of output Product B 320, inlet valves 351, 354, and 355 are operated to allow measured amounts of, respectively, Species 1 301, Species 4 304, and Species 5 305 to be directed to the mixing element 311. During or after mixing, control signals instruct the mutually-exclusive four-output distribution valve 361 to later direct the mixing element's contents to filtering separation element 325. After mixing, the mixing element outlet valve 360 and filtering separation element inlet valve 367 open in some temporal arrangement so that the contents of the mixing element 311 are directed to the filtering separation element 325. At least the filtering separation element inlet valve 367 may close during subsequent filtering separation. After sufficient separation, the filtering separation element outlet valve 372 may be opened so as to yield an outflow of output Product B 320.

Clearing and cleaning may be realized in a similar fashion to that for the first production modality, as described above. Again, the clearing and cleaning may be partitioned into two parts: a first aspect associated with the mixing element 311 and mixing element outlet valve 360, and a second aspect associated with filtering separation element inlet valve 367, filtering separation element 325, and filtering separation element outlet valve 372. The first aspect may be active while the filtering separation process is still active, and the second aspect may be active while the mixing element 311 is being used for another production modality (for example, to begin the production of Product C 330). Alternatively, the two aspects of clearing and cleaning may be merged into a single operation in a manner similar to that described for the first production modality.

Similarly, in a third production modality, directed towards the production of output Product C 330, inlet valves 352, 353, and 355 are operated to allow measured amounts of, respectively, Species 2 302, Species 3 303, and Species 5 305 to be directed to the mixing element 311. During or after mixing, control signals instruct the mutually-exclusive four-output distribution valve 361 to later direct the mixing element's contents to layering separation element 336. After mixing, the mixing element outlet valve 360 and layering separation element inlet valve 368 open in some temporal arrangement so that the contents of the mixing element 311 are directed to the layering separation element 336. At least the layering separation element inlet valve 368 may close during subsequent filtered separation. After sufficient separation, the layering separation element outlet valve opens 373 to yield an outflow of output Product C 330.

Clearing and cleaning may be realized in a similar fashion to that for the first and second production modalities, as described above. Again, the clearing and cleaning may be partitioned into two parts: a first aspect associated with the mixing element 311 and mixing element outlet valve 360, and a second aspect associated with layering separation element inlet valve 368, layering separation element 336, and layering separation element outlet valve 373. The first aspect may be active while the layering separation process is still active, and the second aspect may be active while the mixing element 311 is being used for another production modality (for example, to again begin the production of Products A, B or a new product D). Alternatively, the two aspects of clearing and cleaning may be merged into a single operation in a manner similar to that described for the first production modality.

Figure 3C:
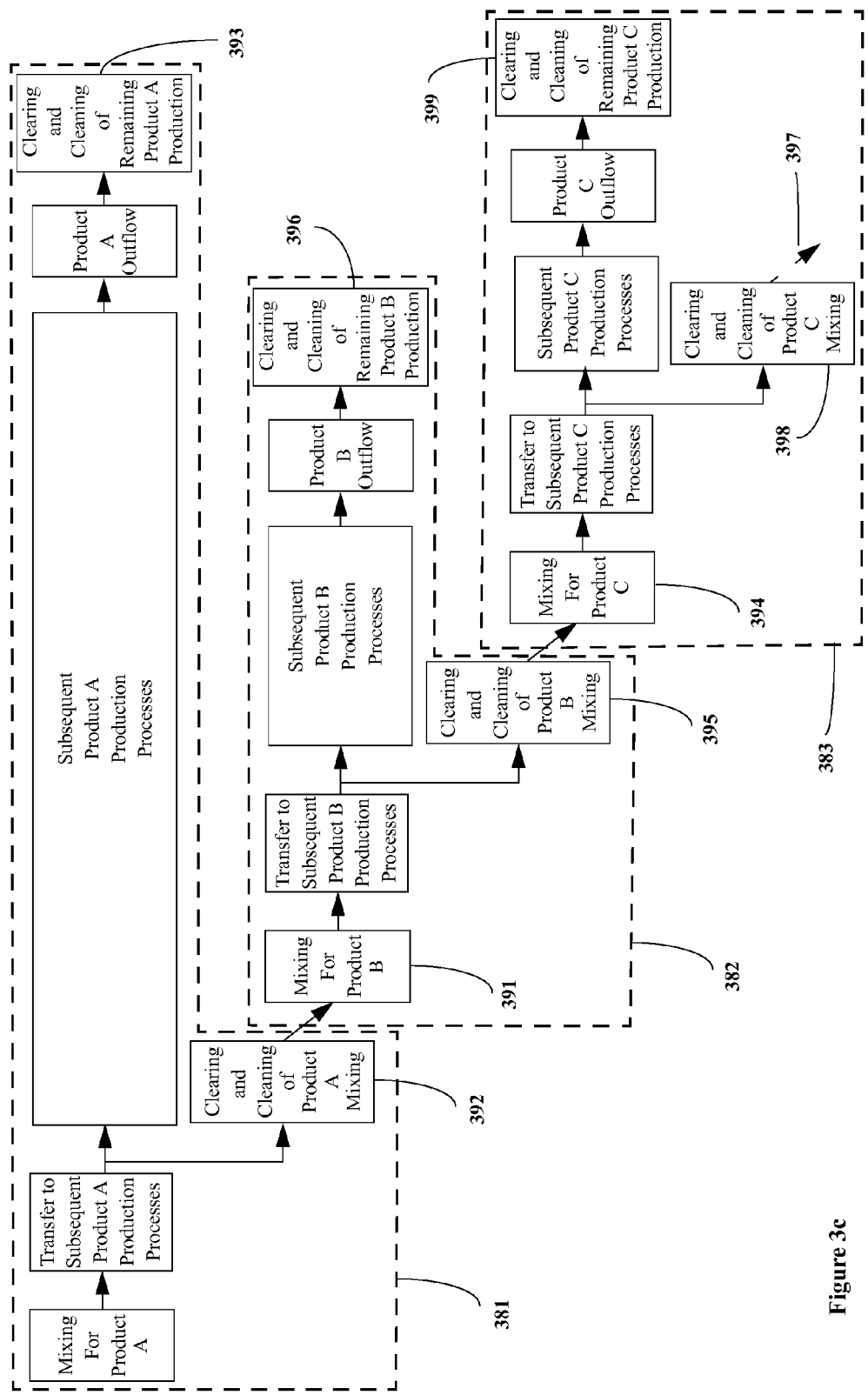
FIG. 3c shows an example that allows for pairwise-overlapping concurrent processing of Products A, B, and C.

Before continuing, a few additional remarks will be made regarding variations for alternate embodiments as would be appreciated by one skilled in the art:

Throughout the exemplary embodiments described above, additional valves may be introduced to provide additional isolation of species sources from phenomena that may occur in the mixing element 311;

The system can be implemented to permit more than one solvent and/or cleaning-gas to be used, as may be required by the overall collection of chemical species used;

By splitting the production process and clearing/cleaning processes into smaller matching sections, efficiency-improving process overlapping and concurrency ("pipelining") may be obtained. FIG. 3c shows an example of this which allows for the pairwise-overlapping concurrent processing 381, 382, 383 of, respectively, Products A, B, and C. In this exemplary arrangement:

the first operation 391 of the Product B production process 382 can begin subsequent to a mid-production Product A clearing and cleaning process 392 rather than at the very end operation 393 of Product A production;

the first operation 394 of the Product C production process 383 can begin subsequent to a mid-production Product B clearing and cleaning process 395 rather than at the very end operation 396 of Product B production;

the first operation 391 of an additional production process can begin subsequent to a mid-production Product C clearing and cleaning process 398 rather than at the very end operation 399 of Product C production;

If the production process for an early product is long, the concurrency can dramatically increase productivity. For example, FIG. 3c shows the later-starting production 382 of Product B completing before the completion of production 381 of Product A, and the even later-starting production 383 of Product C completing at about the same time as completion of the production 381 of Product A.

The example considered is functionally a relatively small-scale one:

Moderate overlap in chemical species

Relatively few operations in each production process

Less than moderate overlap in shared chemical handling and reaction resources.

Such a scale is a viable setting for laboratory automation, certain types of field-operated systems, special purpose applications, and modest complexity chemical production plants. However, as the overlap in chemical species and chemical handling resources increases, the opportunities for sharing and overall applicability of a reconfigurable chemical reaction system increase. As the number of separable operations in each production process increases, the opportunities for increased post-cleaning concurrency, and hence efficiency, for a fixed amount of shared chemical handling and reaction resources increases.

As the overall functionality scale described above increases, increased complexity is introduced in the control routing, passive conduits, cleaning, control, electrical power, storage, thermal management, and other elements and processes. The economies that are delivered by a reconfigurable chemical reaction system may then be weighed against costs of the design, fabrication, and operation of various embodiments. For example, when applied to lab-on-a-chip technology, a well-designed embodiment can have relatively minimal manufacturing costs due to use of photolithography and other related microscale and nanoscale manufacturing technologies. As another example, when applied to high-value special-purpose applications, the costs of complexity can often be readily justified. As yet another example, when applied to high-throughput chemical production plants, additional factors (including real-estate and facilities costs, markets for special chemicals, etc.) can also readily justify the additional complexity. These points will be considered further in a later section in conjunction with FIG. 26.

Chemical Reaction Network Representation

Because various embodiments of the present invention apply to a wide range of chemical reaction environments (including micro scale hybrid-process "chips," "lab-on-a-chip," multiple "lab-chip" systems, field-scale chemical instrumentation, laboratory-scale instruments and devices, chemical production plants, controlled catalytically-activated systems, enzyme networks, and various types of exogenously-activated (optical, electric field, thermal) chemical reaction systems), it is convenient to adopt a general framework such as that of "chemical reaction networks" [see for example the book by Oleg N. Temkin, Andrew V. Zeigarnik, Danail G. Bonchev *Chemical Reaction Networks: A Graph-Theoretical Approach*, CRC-Press, 1996, ISBN 0849328675, as well as "The Chemical Reaction Network Toolbox" CAD tool (software download available at Chemical Reaction Network http://www.che.eng.ohio-state.edu/~feinberg/crnt) and theoretical material such as the lectures by Martin Feinberg (available at http://www.che.eng.ohio-state.edu/~feinberg/LecturesOnReactionNetworks/)].

Such representations of sequences of chemical reactions are useful (although not required) for expressing the generalized capabilities of various embodiments because they abstract away from specific details of individual chemical processes and chemical reaction environments. Chemical reaction network representations further inherently provide great utility in that they simultaneously depict flow sequences in a natural setting for reaction design, lend themselves to powerful mathematical tools and structures (such as graph theory and systems of coupled differential and algebraic equations), and (as a result) provide a natural structure for computer-based modeling (particularly for modularized computational models). These advantages and attributes are also leveraged by various embodiments disclosed herein.

Figure 4A:
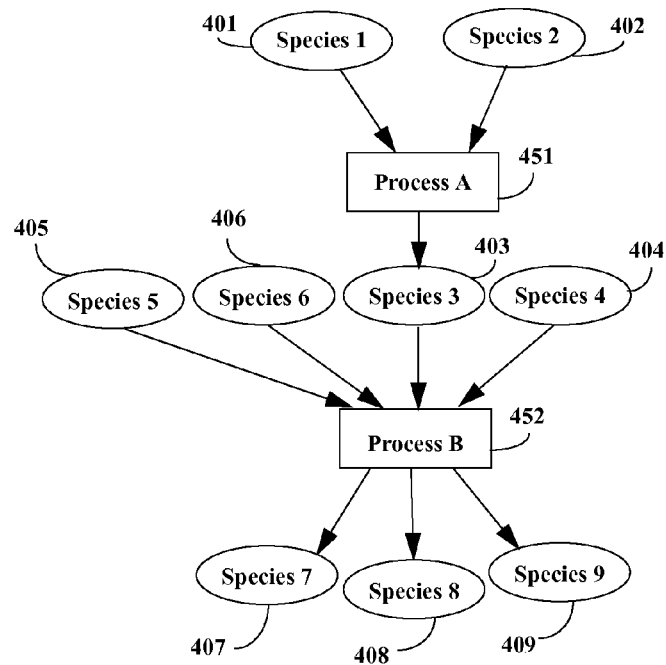
FIG. 4a illustrates one exemplary representation of a particular class of sequential chemical reactions.
Figure 4B:
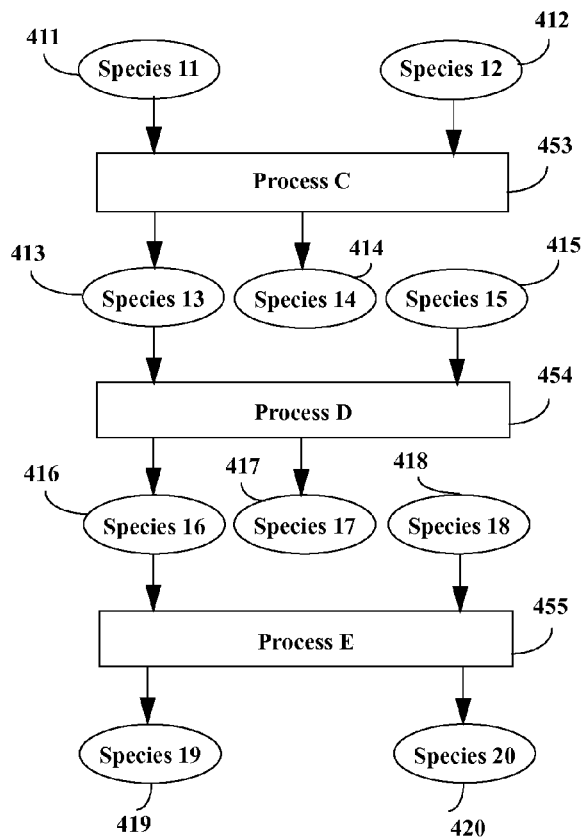
FIG. 4b illustrates another exemplary representation of a different class of sequential chemical reactions.

FIG. 4a illustrates one exemplary representation of a particular class of chemical reactions. For this example, two reagents or chemical sources (Species 1 401 and Species 2 402) are combined in a first process (Process A 451) to create an out-product (Species 3 403), which is in turn combined with three other reagents or chemical sources (Species 4, 5, 6 404-406) in a second process (Process B 452) resulting in out-products and by-products (Species 7, 8, 9 407-409). As another example, FIG. 4b illustrates a similar style representation of a different class of chemical reactions, this one involving four incoming reagents or chemical sources (Species 11, 12, 15, and 18 411, 412, 415, 418) combined over a series of three sequential processes (Processes C, D, and E 453-455) linked by intermediate products (Species 13 413 and 16 416), and producing an out-product (Species 19 419) and three by-products (Species 14 414, 17 417, and 20 420).

High-Level View and Exemplary Classes of Embodiments

Figure 5:
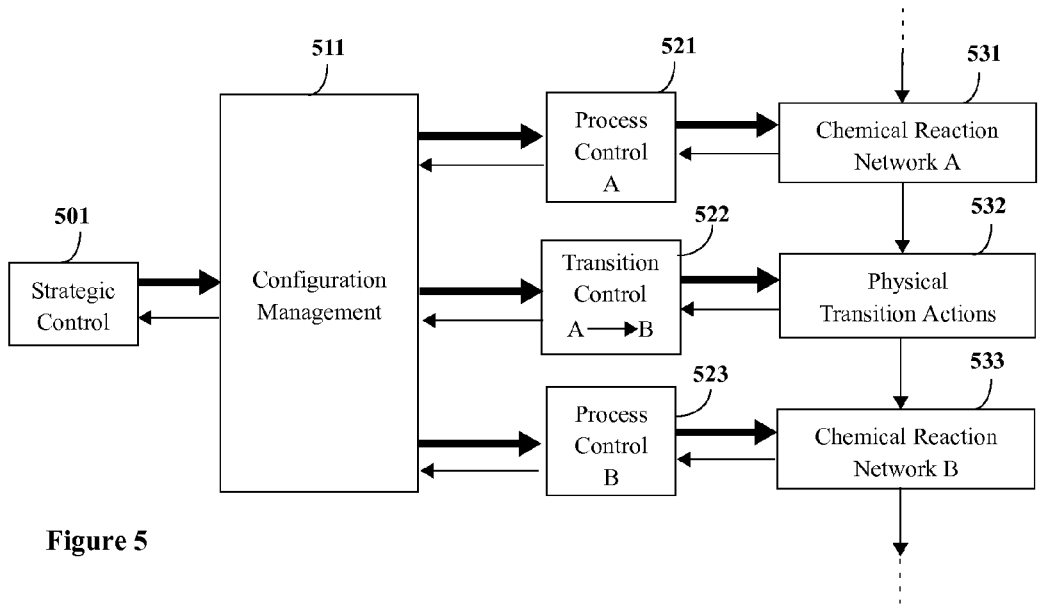
FIGS. 5 and 6 depict an exemplary implementation in which a strategic control element controls a single thread of process flow.

An implementation of one aspect of the invention is illustrated, via this framework, in FIG. 5. Here a strategic control element 501 directs a configuration management element 511 to implement chemical reaction networks 531 and 533. During an interval of time the configuration management element 511 will invoke process control elements 521 and 523 to operate various chemical reaction elements to realize the given chemical reaction networks A 531 and B 533. When instructed to cease operation of one chemical reaction network and/or begin another, one or more transition processes may be invoked. The actions here may include shut down routines associated with the currently active chemical reaction network, unused mid-transit reagent recovering, cleaning, and configuration for the next chemical reaction network to be implemented. This general form is illustrated in FIG. 6.

Controller and Resource Arrangements for Multiple-Thread Operation

Figure 6:
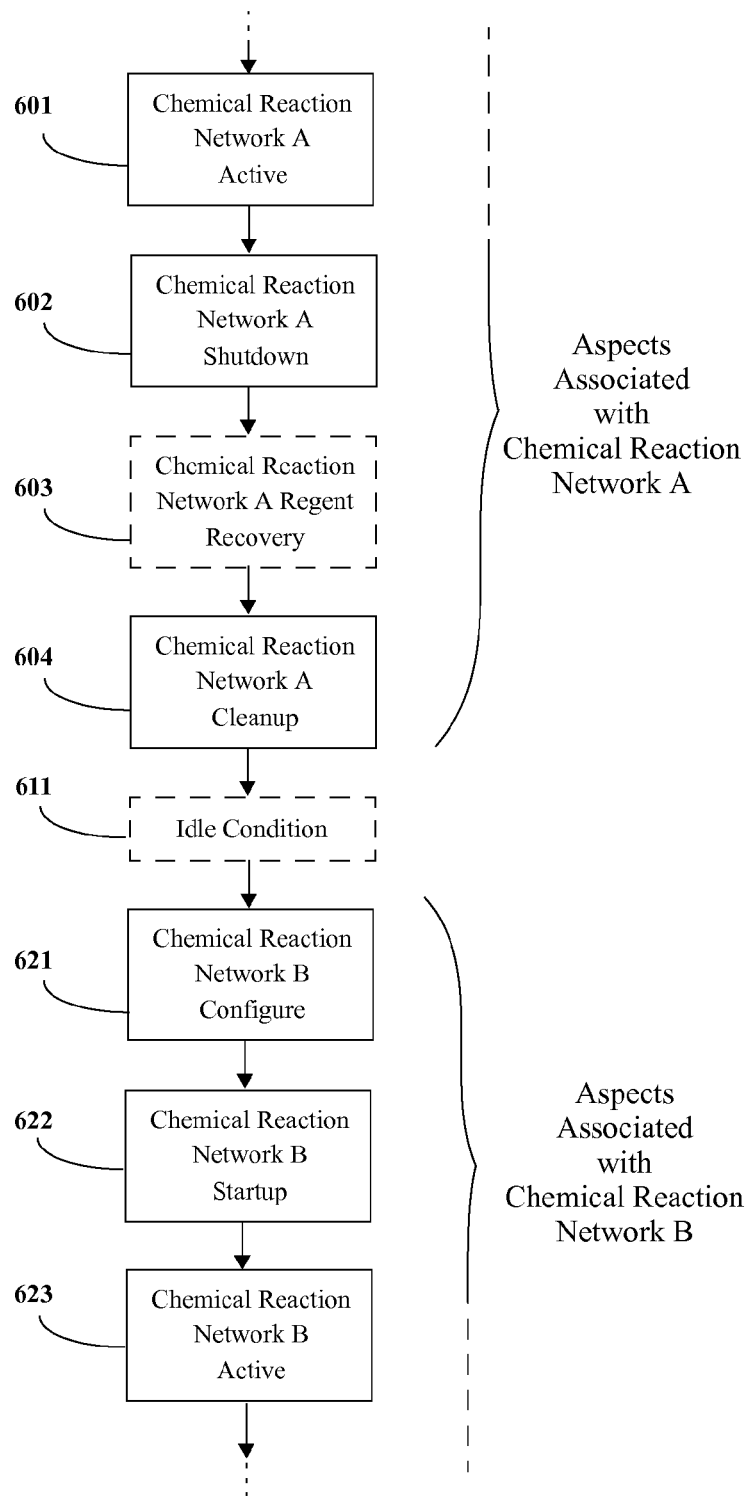

FIG. 5 and FIG. 6 depict an exemplary implementation in which a strategic control element (501 in FIG. 5) controls a single thread of process flow. In other implementations, such as the exemplary implementation depicted in FIG. 7a, a strategic control element 701 can control two or more configuration managers 702.1-702.n to permit several independent chemical reaction networks to operate and transition autonomously and concurrently, employing independent process control elements 703.1-703.n. and independent transitions independent transition control elements 704.1-704.n. Such an arrangement is naturally applicable to situations where groups of chemical reaction and transport elements 705.1-705.n are partitioned into fixed isolated groups.

In other situations, it may be desirable to support various numbers of independent, concurrent operational threads involving widely variable numbers of chemical reaction and transport elements. For example, at one time there may be one large operation involving most of the available chemical reaction and transport elements, while at another time there may be many smaller operations concurrently active, each using a small number of chemical reaction and transport elements. Such an overall arrangement is depicted in FIG. 7b. In such an arrangement, a strategic controller element 710 spawns and retires configuration-managed processes 721.1-721.n as needed.

Figure 7A:
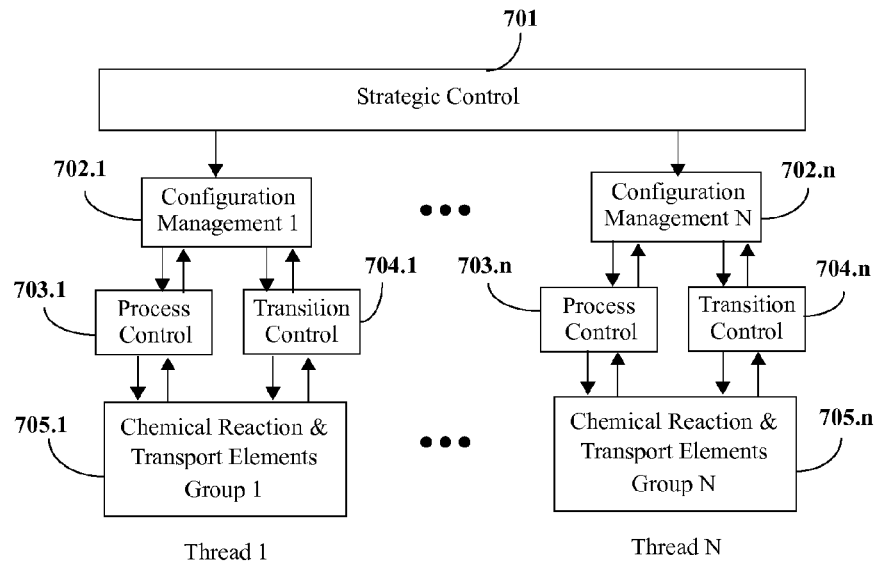
FIG. 7a depicts a strategic control element controlling two or more configuration managers.
Figure 7B:
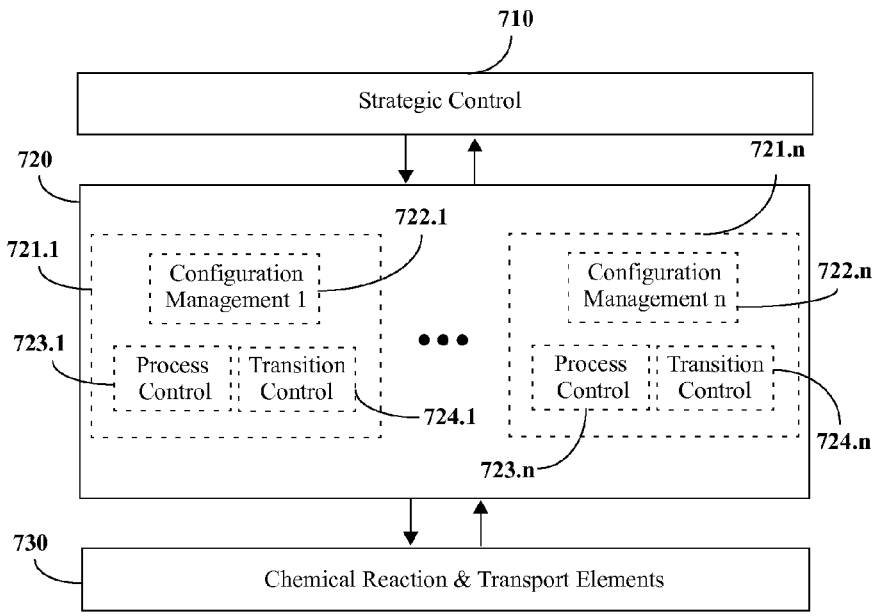
FIG. 7b depicts a strategic controller element that spawns and retires configuration-managed processes as needed.
Figure 7C:
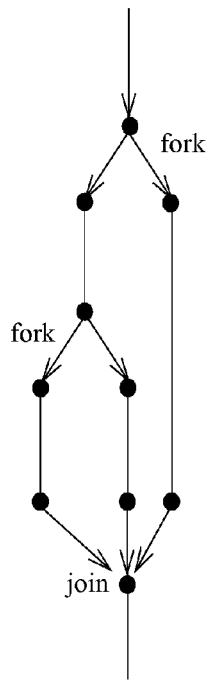
FIG. 7c illustrates an example of supporting fork-and-join operations.
Figure 7D:
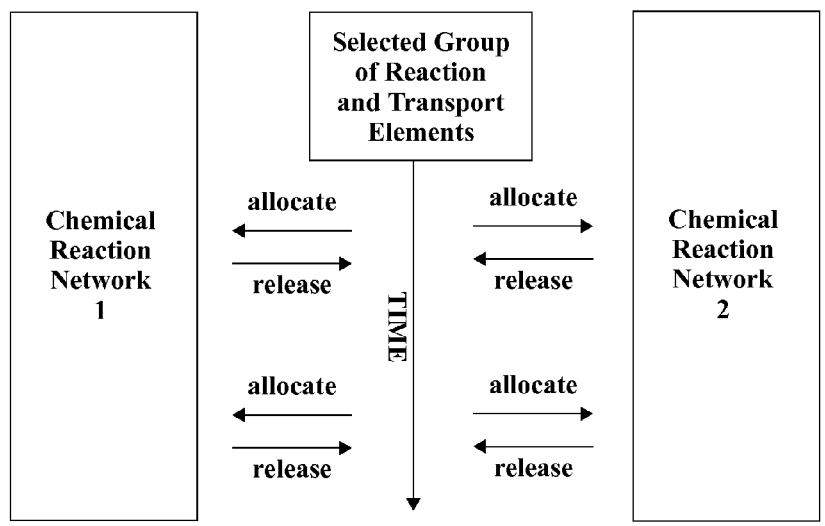
FIG. 7d depicts one or more chemical reaction elements serially shared between two or more concurrent chemical reaction networks.

The exemplary arrangement depicted in FIG. 7b can be readily adapted by those skilled in the art to be capable of supporting fork-and-join operations, depicted in FIG. 7c. Additionally, the exemplary arrangement depicted in FIG. 7c can be readily adapted by those skilled in the art to be capable of supporting operational modes wherein one or more chemical reaction elements are serially shared between two or more concurrent chemical reaction networks, as depicted in FIG. 7d.

In yet another implementation, the strategic controller element may internally provide all needed functions associated with configuration managed elements, or otherwise operate in such a manner that no configuration managed element is needed, instead itself directly spawning and retiring process control and transition control elements as needed.

Abstract Operational Element and its Internal Constituents

In some or all of these various fashions, the strategic controller and/or configuration management elements act much as a multitasking operating system in a computer, allocating hardware and processing resources over time for a variety of tasks, subject to physical resource and task-switching constraints.

Figure 8A:
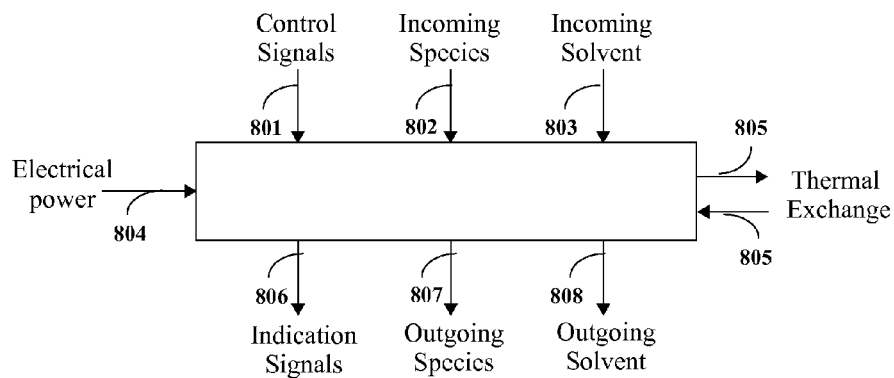
FIG. 8a illustrates an abstract operational element consuming various possible inputs and producing various possible outputs.

Abstracting the overall systems described thus far, FIG. 8a illustrates a very general view of some aspects of the invention, representing it as an abstract operational element consuming one or more of Electrical power 804,
Incoming chemical species 802 (reagents, samples, intermediate products, etc.),
Solvent(s) and/or cleaning gases 803,
Thermal exchange transfer 805, and, under the direction of incoming control signals, creating:

Outgoing species 807 (products, wastes),
Outgoing solvents 808 and/or cleaning gases, Indication signals 806 (from process controllers and/or sensors).

Figure 8B:
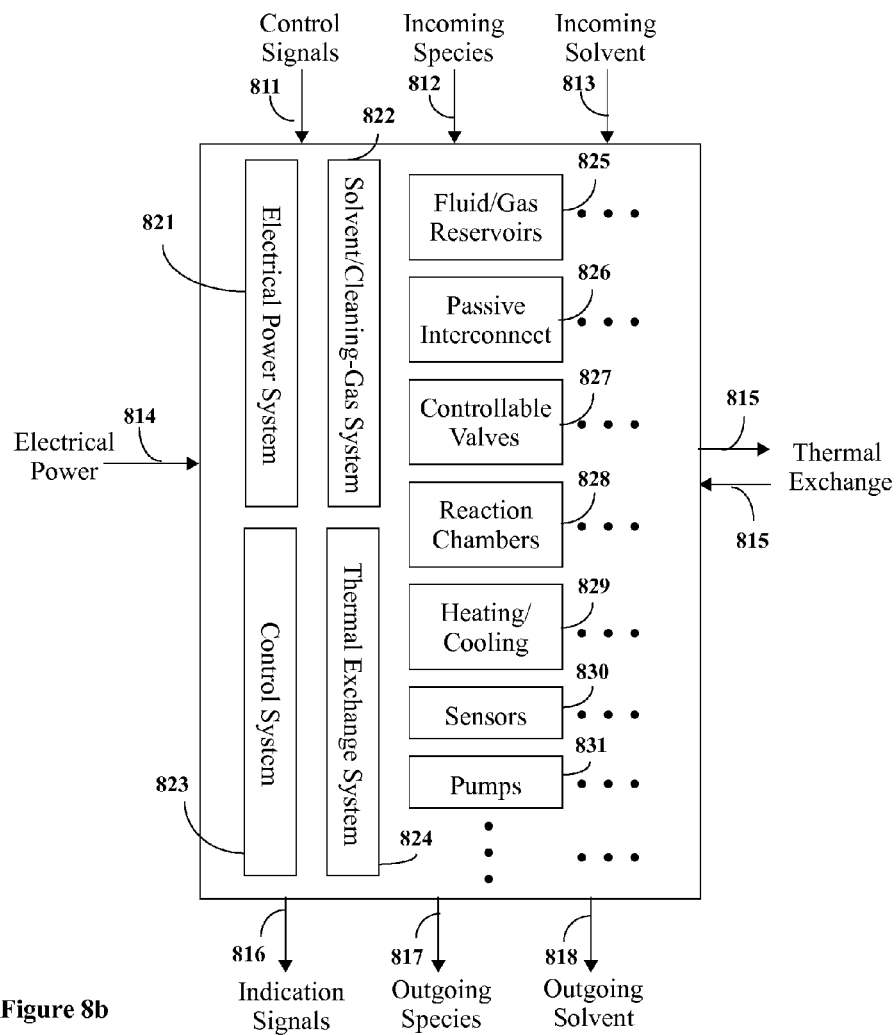
FIG. 8b illustrates an exemplary classification and organization, structured with exemplary environment and utility entities.

Within the abstract operational element of FIG. 8*a* would be a number of environment and utility entities as well as specific operational entities. These may be classified and organized in any number of ways. FIG. 8*b* illustrates an exemplary classification and organization, structured with exemplary environment and utility entities comprising:

Electrical power system 821,
Thermal exchange system 824,
Control system 823,
Solvent/cleaning-gas system 822, and exemplary operational entities comprising:

Fluid and/or gas reservoirs 825,
Passive interconnection pathways 826,
Controllable valves 827,
Reaction chambers 828,
Heating and cooling elements 829,
Sensors 830,
Pumps 831,
Other entities (evaporators, condensers, agitators, etc.).

The electrical power system 821 depicted in FIG. 8*b* distributes and/or adapts electrical power 814 to the various operational entities. It additionally may distribute and/or adapt electrical power 814 to other entities shown in the Figure, such as the control system 823 (to be discussed next). The electrical power system 821 may additionally internally comprise voltage regulation, current limiters, thermal shutdown capabilities, backup power provisions, noise isolation, high-frequency filtering, voltage-spike protection, power-reversal protection, and other relevant capabilities that may be useful for or required by various embodiments of the invention, as is clear to one skilled in the art. It additionally may distribute and/or adapt electrical power to other entities shown in the Figure, such as the aforementioned control system. The electrical power system 821 may additionally internally comprise voltage regulation, current limiters, thermal shutdown capabilities, backup power provisions, noise isolation, high-frequency filtering, voltage-spike protection, power-reversal protection, and other relevant capabilities that may be useful for or required by various embodiments of the invention, as is clear to one skilled in the art.

The control system 823 depicted in FIG. 8*b* may accept incoming control signals or operate autonomously, and creates, adapts, or directs control signals to the individual operational entities. The control system 823 additionally may collect indication signals from one or more of the plurality of operational entities, and may provide outgoing indication signals 816. The associated control and indication signals may be electrical, optical, pneumatic, fluid, chemical, or of other forms as may be advantageous for particular embodiments or applications of the invention. One skilled in the art will immediately recognize that many other control system arrangements are possible, such as a partitioned control system that may or may not include interconnections among the partitions.

The solvent/cleaning-gas system 822 depicted in FIG. 8*b* distributes and/or adapts incoming and outgoing solvent(s) and/or cleaning-gas(es) to the plurality of operational entities. In many embodiments, the shared incoming solvent/cleaning-gas system 822 may be advantageously merged into, or be part of, the interconnection network to be described below, as is clear to one skilled in the art and as may be advantageous for particular embodiments or applications of the invention.

The thermal exchange system 824 depicted in FIG. 8*b* collects, and/or distributes, and/or adapts heat flows to and from the plurality of operational entities as may be advantageous for particular embodiments or applications of the invention. Unwanted heat would typically be gathered by the shared thermal exchange system 824. In some embodiments the shared thermal exchange system 824 may provide all heat to operational entities, but in many implementations needed heat may be generated locally by conversions of electrical power, chemical processes, pressure modulation, or other localized processes. In advanced implementations, the shared thermal exchange system 824 may provide thermal redistribution flow (i.e., using waste heat or waste cooling, respectively, to provide needed heat and cooling elsewhere). The thermal exchange system 824 may incorporate thermal storage elements to accomplish this. More generally, the thermal exchange system 824 may comprise fluid-based, and/or gas-based, and/or passive or active (e.g., semiconductor, etc.) solid-based thermal transport elements, switchable thermal routing elements, heat generation elements, heat-to-electricity elements (such as thermal diodes; see for example E. A. Thompson, MIT news office, "Device could convert waste heat into electricity," available at http://web.mit.edu/newsoffice/2001/electricity-1205.html, ceramic thermoelectric modules; and National Institute of Advanced Industrial Science and Technology (AIST) "Electric Power Generated from Waste Heat," available at http://www.aist.go.jp/aist_e/latest_research/2005/20050617/20050617.html), electromagnetic turbines, or other processes (such as electrochemical), etc. To the extent that the thermal exchange system 824 uses or generates electricity, it may be in some implementations interconnected with the shared electrical power system 821 described above.

The fluid and/or gas reservoirs 825 depicted in FIG. 8*b* may be chambers for the temporary storage of fluids and/or gasses involved in process-internal operations of the invention. The reservoirs 825 comprise a storage volume and one or more (typically a plurality) ports which may be directly or indirectly connected with the passive interconnect conduits 826. In most situations it is advantageous to provide controllable valves 827 localized to these ports, close to the reservoirs themselves 825. The reservoirs 825 may further include additional pressure or capillary-action induced evacuation capabilities, cleaning capabilities involving shared or dedicated paths for solvent flows, or other attributes and elements as may be advantageous for particular embodiments or applications of the invention.

The passive interconnect 826 depicted in FIG. 8*b* comprises fixed routes between operational entities and controllable valves 827. The passive interconnect 826 and controllable valves 827 work together to provide routing of reagents, products, and wastes among the plurality of operational entities. The passive interconnect 826 may also include sensors for the measurement of flow-rate, temperature, ion concentration, particulate turbidity, optical properties, etc. The passive interconnect 826 may further incorporate heating and cooling capabilities, condensation handling, precipitate handling, stand-alone cleaning, etc.

In embodiments where the passive interconnect 826 comprises sensor elements 830, the interconnection network may additionally be linked with the electrical power and control systems 821 and 823 described earlier. In embodiments where the passive interconnect 826 comprises heating and cooling capabilities, the passive interconnect 826 may additionally connect with the thermal exchange system 824 described earlier. In embodiments where the passive interconnect 826 comprises precipitate handling and/or stand-alone cleaning the passive interconnect 826 may additionally connect with one or both of the incoming solvent/cleaning-gas system 813 and outgoing solvent/cleaning-gas system 818 described earlier.

The controllable valves 827 depicted in FIG. 8b may be used to control fluid and/or gas flow. The controllable valves 827 may be controlled directly by a modulated power source (mechanical, electrical, pneumatic, fluid, etc.) or indirectly by externally provided control signals (electrical, optical, mechanical, pneumatic, fluid, chemical, etc.) as may be advantageous for particular embodiments or applications of the invention. The technologies used to implement controllable valves 827 may include electromagnetic, thermal expansion, or other techniques as may be advantageous for particular embodiments or applications of the invention. The controllable valves 827 may be simple on/off valves, multiple-port selector valves, multiple-port distribution valves, or valves of other types, as may be advantageous for particular embodiments or applications of the invention. It is often valuable to implement controllable multiple-port selector valves, multiple-port distribution valves, and related structures which comprise provisions for in situ cleaning of at least some portions of their internal flow paths.

The reaction chambers 828 depicted in FIG. 8b provide structured reaction environments for chemical reactions to occur. In addition to inflow inlets, outflow outlets, and associated valves, the reaction chambers 828 may further comprise heaters, stirrers, agitators, aerators, sensors, structured internal surfaces (such as perforated plates, gratings, filaments, textured walls, porous filters, selective membranes, etc.), acoustic transducers, lasers, light sources, electrodes, and other additional structures and/or sub-elements as may be advantageous for particular embodiments or applications of the invention. Reaction chambers 828 may be multifunction, or may be optimized for specific individual functions such as heating, mixing, chemical reaction control, etc., as may be advantageous for particular embodiments or applications of the invention.

The heating and/or cooling elements 829 depicted in FIG. 8b may comprise heat generation elements, fluid-based, and/or gas-based, and/or passive or active (e.g., semiconductor, etc.) solid-based thermal transport elements, switchable thermal routing elements, heat-to-electricity elements, electromagnetic turbines, or other processes (such as electrochemical, laser, etc.) as may be advantageous for particular embodiments or applications of the invention.

The sensors 830 depicted in FIG. 8b may sense temperature, pressure, fluid level, ion concentration, pH, turbidity, flow rate, optical properties, electrical potential, connectivity, light emission, vibration, or other attributes as may be advantageous for particular embodiments or applications of the invention. The sensors 830 may be attached to, or integrated into, other elements such as the reservoirs 825, passive interconnect conduits 826, controllable valves 827, and reaction chambers 828 described above as well as the elements described below as may be advantageous for particular embodiments or applications of the invention. The sensors 830 typically produce outgoing indication signals which may be electrical, optical, mechanical, pneumatic, fluid, chemical, or of other forms as may be advantageous for particular embodiments or applications of the invention The pumps 831 depicted in FIG. 8b may comprise any number of pump technologies including turbine, peristaltic, piston, vane, centrifugal impeller, meshed-gear, annular gear, etc. The pumps 831 are typically controlled, and may be directly controlled by external modulation of applied power, or indirectly controlled via control signals (electrical, optical, pneumatic, fluid, etc.) as may be advantageous for particular embodiments or applications of the invention.

If desired, the elements of FIG. 8b may include additional other specialized elements such as mixers, heating chambers, evaporators, condensers, agitators, absorbers, filters, sublimers, driers, selective membranes, sonic vibrators, optical or laser stimulators, and other elements as may be advantageous for particular embodiments or applications of the invention.

Larger Systems Built from Pluralities of Abstract Operational Elements

Figure 8C:
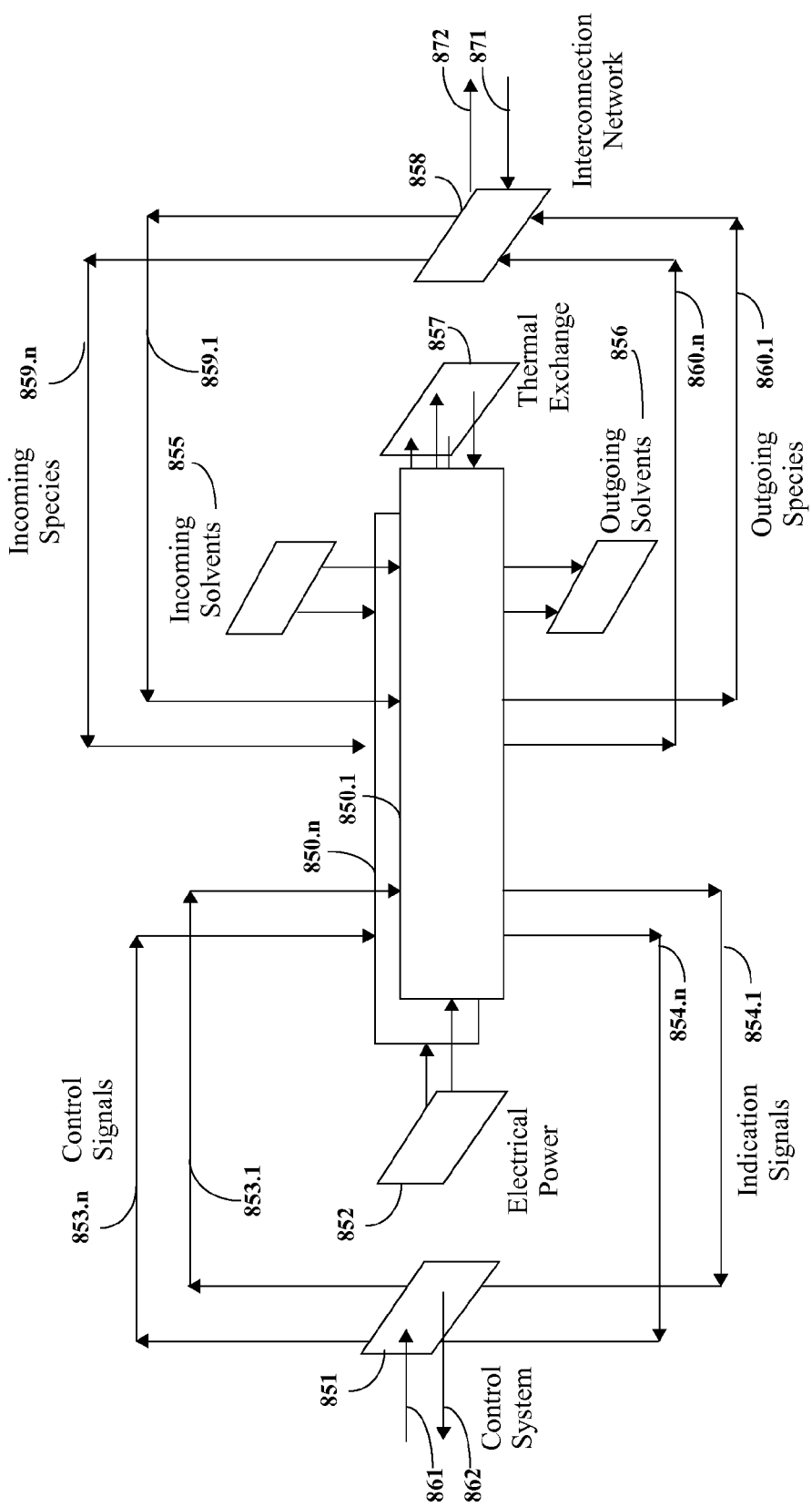
FIG. 8c depicts an interconnected version of FIG. 8a to form a larger system.

Pluralities of the abstract operational elements of FIG. 8a may be, in turn, interconnected to form a larger system of various types. FIG. 8c depicts an exemplary illustration of this. In the center of the Figure are shown a plurality of instances of systems 850.1-850.n of the type depicted in FIG. 8a. These operate as functionally or operationally partitioned chemical reaction (or chemical handling) subsystems of the larger system depicted in FIG. 8c. Although one skilled in the art will immediately recognize that many other arrangements are possible, the embodiment shown in FIG. 8c comprises a global control system 851, a global electrical power system 852, a global incoming solvent (and cleaning-gas) system 855, a global outgoing solvent (and cleaning-gas) system 856, and an interconnection network 858 with associated species inflows 871 into the system and associated species outflows 872 out from the system.

The global control system 851 depicted in FIG. 8c may accept incoming control signals 861 or operate autonomously, and creates, adapts, or directs control signals 853.1-853.n to the individual chemical reaction/handling subsystems 850.1-850.n. The global control system 851 additionally may collect indication signals 854.1-854.n from one or more of the plurality of chemical reaction/handling subsystems 850.1-850.n, and may provide outgoing indication signals 862. One skilled in the art will immediately recognize that many other control system arrangements are possible, such as a partitioned control system which many or may not include interconnections among the partitions.

The global electrical power system 852 depicted in FIG. 8c distributes and/or adapts electrical power to the plurality of chemical reaction/handling subsystems 850.1-850.n. The global electrical power system 852 additionally may distribute and/or adapt electrical power to other entities shown in the Figure, such as the aforementioned global or partitioned control system(s) 851. The global electrical power system 852 may additionally internally comprise voltage regulation, current limiters, thermal shutdown capabilities, backup power provisions, noise isolation, high-frequency filtering, voltage-spike protection, power-reversal protection, and other relevant capabilities that may be useful for or required by various embodiments of the invention, as is clear to one skilled in the art. It additionally may distribute and/or adapt electrical power to other entities shown in the Figure, such as the aforementioned global or partitioned control system(s) 851. The global electrical power system 852 may additionally internally comprise voltage regulation, current limiters, thermal shutdown capabilities, backup power provisions, noise isolation, high-frequency filtering, voltage-spike protection, power-reversal protection, and other relevant capabilities that may be useful for or required by various embodiments of the invention, as is clear to one skilled in the art.

The global incoming solvent/cleaning-gas system 855 depicted in FIG. 8c distributes and/or adapts incoming solvent(s) and/or cleaning-gas(es) to the plurality of chemical reaction/handling subsystems 850.1-850.n. In an alternate embodiment, the global incoming solvent/cleaning-gas system 855 may be merged into, or be part of, the interconnection network 858 to be described below, as is clear to one skilled in the art.

Similarly, the global outgoing solvent/cleaning-gas system 856 depicted in FIG. 8c collects and/or adapts outgoing flows of solvent(s) and/or cleaning-gas(es) from the plurality of chemical reaction/handling subsystems 850.1-850.n. In an alternate embodiment, the global incoming solvent/cleaning-gas system 855 may be merged into, or be part of, the interconnection network 858 to be described below, as is clear to one skilled in the art.

The global thermal exchange system 857 depicted in FIG. 8c collects, and/or distributes, and/or adapts heat flows to and from the plurality of chemical reaction/handling subsystems 850.1-850.n. Unwanted heat would typically be gathered by the global thermal exchange system 857. In some embodiments the global thermal exchange system 857 may provide all heat to chemical reaction/handling subsystems 850.1-850.n, but in many implementations needed heat may be generated locally by conversions of electrical power, chemical processes, pressure modulation, or other localized processes. In advanced implementations, the global thermal exchange system 857 may provide thermal redistribution flow (i.e., using waste heat or waste cooling, respectively, to provide needed heat and cooling elsewhere). The global thermal exchange system 857 may incorporate thermal storage elements to accomplish this. More generally, the global thermal exchange system 857 may comprise fluid-based, and/or gas-based, and/or passive or active (e.g., semiconductor, etc.) solid-based thermal transport elements, switchable thermal routing elements, heat generation elements, heat-to-electricity elements, electromagnetic turbines, or other processes such as electrochemical), etc. To the extent that the global thermal exchange system 857 uses or generates electricity, it may be in some implementations interconnected with the global electrical power system 852 described above.

The interconnection network 858 depicted in FIG. 8c may comprise passive (fixed) or active (switched) routing of chemical species, products, and wastes among the plurality of chemical reaction/handling subsystems 850.1-850.n. It interconnects with input flows 859.1-859.n into the chemical reaction elements chemical reaction/handling subsystems 850.1-850.n as well as output flows 860.1-860.n out from the chemical reaction elements chemical reaction/handling subsystems 850.1-850.n.

The interconnection network 858 depicted in FIG. 8c may also include sensors for the measurement of flow-rate, temperature, ion concentration, particulate turbidity, optical properties, etc. The global interconnection network 858 may further comprise heating and cooling capabilities, condensation handling, precipitate handling, stand-alone cleaning, etc. In embodiments where the interconnection network 858 comprises controllable switching elements and/or sensing elements, the global interconnection network 858 may additionally connect with the electrical power and control systems 852 and 851 described earlier. In embodiments where the interconnection network comprises heating and cooling capabilities, the interconnection network 858 may additionally connect with the thermal exchange system 857 described earlier. In embodiments where the global interconnection network 858 comprises precipitate handling and/or stand-alone cleaning, the global interconnection network 858 may additionally connect with one or both of the incoming solvent/cleaning-gas system 855 and outgoing solvent/cleaning-gas system 856 described earlier.

Scale and Physical Classification of Systems Provided for by the Invention

Figure 9:
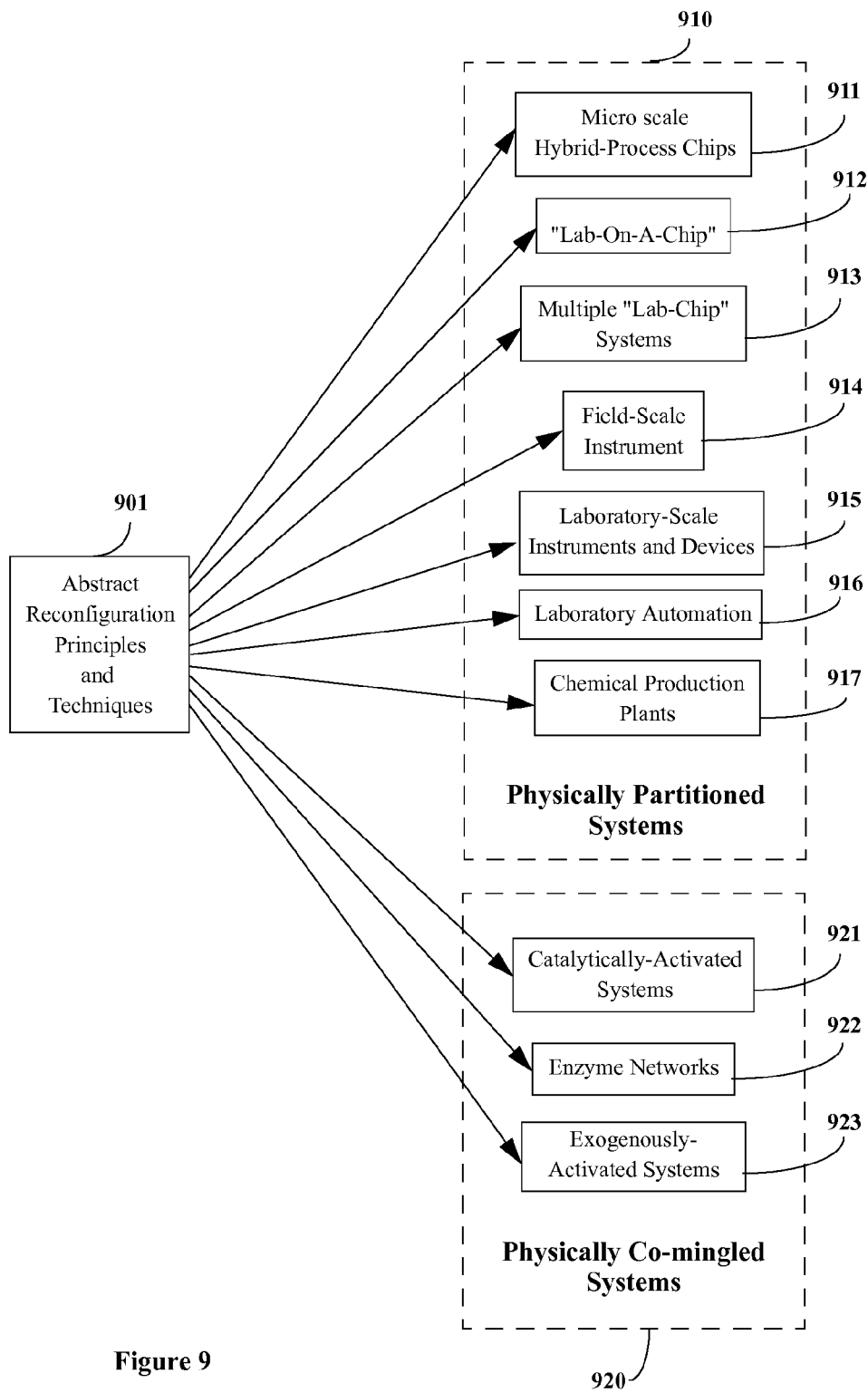
FIG. 9 shows a view of how the reconfigurable principles and techniques of the invention may be applied tow a wide range of applications.

With these general principles established, attention is now directed to further consideration of the many aforementioned application areas, depicted in FIG. 9, to which these principles may be advantageously incorporated. In particular, the abstract reconfiguration principles and techniques 901, as well as other aspects, may be incorporated into a wide range of larger systems and applications at a wide variety of physical scales, including:

Enzyme networks 922
Catalytically-activated systems 921
Exogenously-activated distributed chemical systems 923
Microscale hybrid-process chips 911
"Lab-On-A-Chip" 912
Multiple "Lab-Chip" systems 913
Field-scale instrument 914
Laboratory-scale instrument and devices 915
Laboratory automation 916
Chemical production plants 917

Additional consideration of this extensively wide range, particularly with respect to enabling economic considerations, will be provided in the later discussion provided in conjunction with then-to-be-discussed FIG. 26.

FIG. 9 shows an organization of these as partitioned into two classes, distinguished as to whether the chemical reactions and related aspects (mass transport, energy distribution, thermal regulation, etc.) occur in discretely physically partitioned manners or in distributed physically comingled manners:

Physically Partitioned Chemical Reaction Systems 910:
Microscale hybrid-process chips 911
"Lab-On-A-Chip" 912
Multiple "Lab-Chip" systems 913
Field-scale instrument 914
Laboratory-scale Instrument and devices 915
Chemical production plants 917
Physically Commingled Chemical Reaction Systems 920:
Catalytically-activated systems 921
Enzyme networks 922
Exogenously activated systems 923

Physically Co-mingled Chemical Reaction Systems 920 are more readily understood after detailed treatment of Physically Partitioned Chemical Reaction Systems 910. The next immediately subsequent portions of the description will thus be directed towards Physically Partitioned Chemical Reaction Systems 910, with Physically Co-mingled Chemical Reaction Systems 920 considered later.

Physically Partitioned Chemical Reaction System Embodiments

Of first concern in the application to Physically Partitioned Chemical Reaction Systems 910 are:

Multiple-port selection and distribution valves
Chemical storage elements and their transport operation
Chemical transport elements and their transport operation
Chemical reaction elements and their reaction operation
Cleaning of multi-port valves, chemical reaction, and
  transport elements
  solvent strategies
  gas strategies
  unused reagent recovery.

A notable aspect of the invention relates to the multiple-port selection and distribution valves. In the context of these, relevant introductory aspects of transport elements, reaction elements, and cleaning are considered. After the conclusion of the discussion of multiple-port selection and distribution valves, aspects of other elements in the list above are considered.

Overview of Multiple-Port Valves, Matrix Valves, and Valve Complexes

Figure 10A:
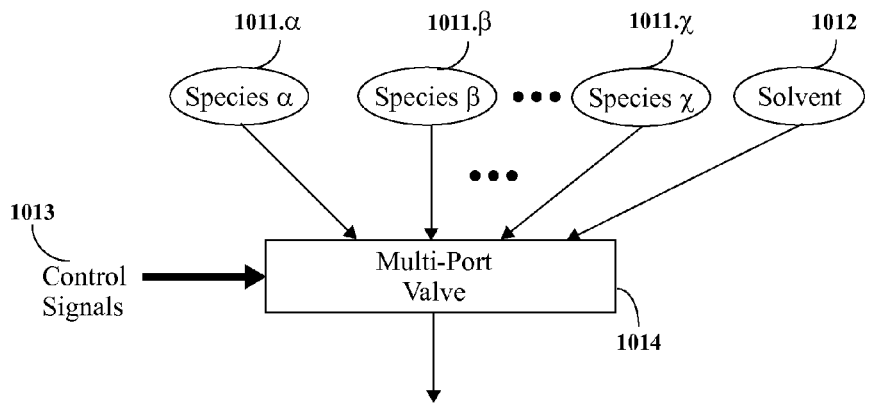
FIG. 10a depicts a general concept of a multiple-port selection valve that is operated responsively to control signals so as to select from a plurality of species flows and a solvent flow.

FIG. 10a depicts the general concept of a multiple-port valve 1014, also often termed "switching valve," which for brevity hereto follow may be termed "multi-port valve."

Figure 10B:
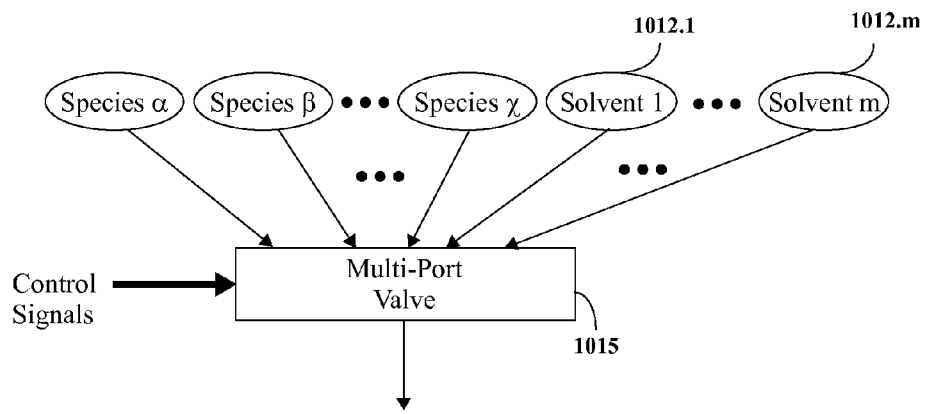
FIG. 10b depicts a variation of the arrangement of FIG. 10a wherein two or more solvents are additionally supported.
Figure 10C:
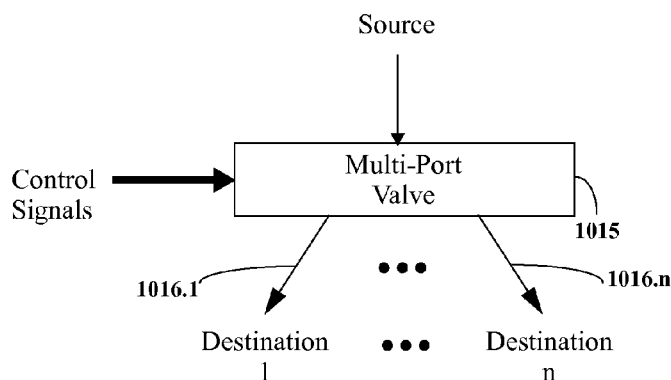
FIG. 10c depicts a multi-port distribution valve implementation.

Under the direction of one or more control signals 1013 (electrical, pneumatic, fluidic, optical, mechanical, etc.), in one modality the multi-port valve selects from among two or more possible flows, here depicted as chemical species (which may be in the form of liquids, gases, or even granulated powders) $1011.\alpha$-$1011.\chi$ and solvents (liquid and/or gas) 1012. A multi-port valve may also include a "closed" position where no flow is allowed. FIG. 10b illustrates a variation 1015 of this arrangement wherein two or more solvents 1012.1-1012.m are supported (for example, water, neutral gas, aromatic compounds, alcohols, etc). Many multi-port valve implementations can be used in the reverse configuration, as depicted in FIG. 10c, where a source flow (liquid, gas, powder, etc.) may (in mutually exclusive fashion) be directed to two or more destinations 1016.1-1016.n.

Multi-port valves of various types are made by a number of manufacturers (where they are often called "switching valves," "selection valves," "stream selectors," "flow injection valves," etc.) in a variety of physical sizes. Some examples include the Cheminert series of products [http://www.flowinjection.com/valves.html] by FIAlab Instruments (14450 N.E. 29$^{th}$ Pl., Bellevue, Wash., 98007, 800-963-1101), the 1200 Series [http://www.chem.agilent.com/Scripts/PDS.asp?1Page=6269] by Agilent Technologies, Inc. (395 Page Mill Rd., Palo Alto, Calif. 94306, 877-424-4536), the Series 080T [http://www.bio-chemvalve.com/spec.asp?id:=15] and Series 105T Flow Selection Valves [http://www.bio-chemvalve.com/spec.asp?id=16] manufactured by Bio-Chem Valve Inc. (85 Fulton Street, Boonton, N.J. 07005, 973-263-3001), as well as other manufacturers for various industrial and laboratory applications. These embodiments employ various techniques, such as rotating notched balls, tunneled cylinders, etc. Most of these products are directed towards air and gas flow. Those directed to the control of fluids typically provide little in the way of preventing interspecies contamination when employed in the configurations of FIG. 10a and FIG. 10b. A related case is that of controllable "valve manifolds" or "serial valves" commonly employed in pneumatic and hydraulic systems, which are typically used as single-input multiple-output mode. Such commercial products are manufactured by Festo (395 Moreland Road, Hauppauge, N.Y. 11788, 314-770-1684) [see for example http://a1989.g.akamai.net/f/1989/7101/3d/www.festo.com/INetDomino/files_01/Info207_FastSwitchingV.pdf], MAC (30569 Beck Road, Wixom, Mich. 48393-7011, 248-624-7700) [see for example http://www.macvalves.com/serial.htm], and SMC Corporation of America (3011 North Franklin Road, Indianapolis, Ind. 46266, 317-899-4440) [see for example http://eu10600038.eu.verio.net/SMC_Europe/SMC_Europe_qa/SMC_Europe/NEW_EBP/Level1EU.jsp?ctry=1&id=9406&pos=Solenoid%20Valve]. In these embodiments, however, the (typically single-input multiple-output) manifold arrangement of controllable on/off valves is effectively used as control signal transducers, transforming incoming electrical or mechanical signals into outgoing pneumatic and hydraulic signals. Solenoid-controlled fluidic valve manifolds are offered by Precision Dynamics, Inc. (60 Production Court, New Britain, Conn. 06051 Phone: 888-840-1230) [see for example http://www.predyne.comr/valves.asp] and Peter Paul Electronics (480 John Downey Dr., New Britain, Conn. 06050 Phone: 860-229-4884) [see for example http://www.peterpaul.com/whats_new_display2.php4?cat_id=6], among others.

Because there are typically no flow-direction restriction structures in these, the open path created through connected ports in a multiple port valve freely permits bidirectional flow. As a result, traditional multiple port valves may be equally well-employed for the distribution of a single flow-source to multiple flow-destinations (i.e., a multiple-port distribution valve) as well as for the selection of one of multiple possible flow-sources for direction to a single flow-destination (i.e., a multiple port selection valve).

A multi-port valve may well be implemented as a system of more primitive forms of valves. A group of valves that are configured to operate as a distinct subsystem will be termed a "valve complex." A multiple-port valve implemented as a valve complex will be termed a "multiple-port valve complex" or "multi-port valve complex." Such multiple-port valve complexes are an important realization consideration in some application settings (such as "lab-on-a-chip" and laboratory automation overlays).

Figure 11D:
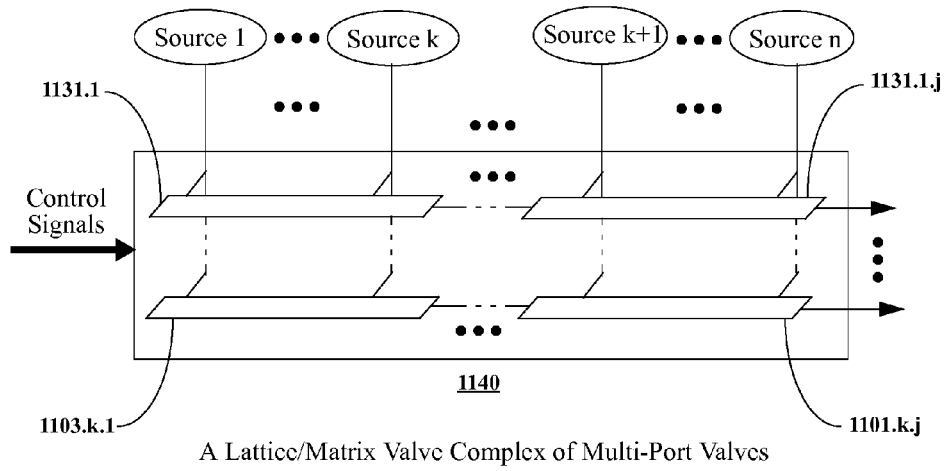
Figure 11E:
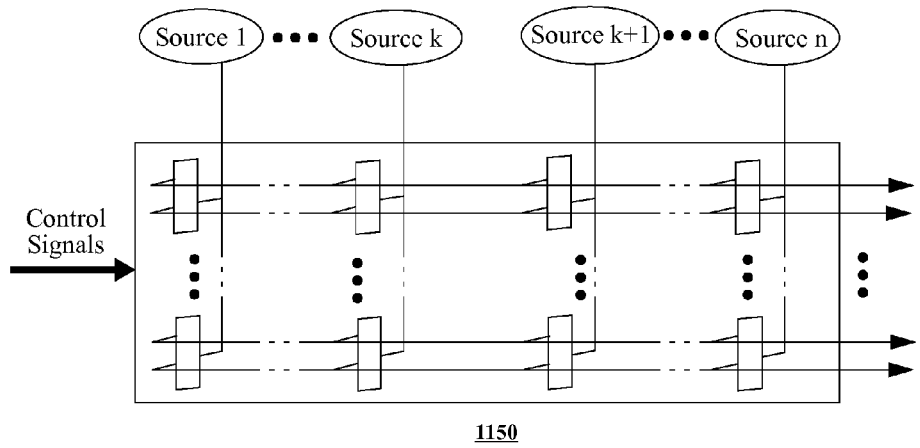

For some embodiments, a "matrix-valve" configuration (which also may be termed "valve lattice" or "valve array") may be advantageous. A depiction of an exemplary matrix-valve configuration made from simple on/off valves is provided in FIG. 11a. Other implementations are also possible, for example those comprising pluralities of various multi-port valves; four possible examples are shown in FIGS. 11b-11e. In the case depicted in FIG. 11b, the matrix valve comprises a number of multi-port valves 1101.1-1101.m, this number equal to the number m of destination ports of the overall matrix-valve, and wherein the number of ports on each multi-port valve 1101.1-1101.m equal to the number n of source ports of the overall matrix valve. In the case depicted in FIG. 11c, the matrix valve comprises a number of multi-port valves 1102.1-1102.n, this number equal to the number of source ports n, wherein the number of ports on each multi-port valve 1102.1-1102.n is equal to the number k of destination ports. The case depicted in FIG. 11d is an adaptation of the case depicted in FIG. 11b wherein each of the k multi-port valves 1101.1-1101.m, is implemented as a cascade of two or more multiport valves. The case depicted in FIG. 11e is an adaptation of the case depicted in FIG. 11c wherein each of its multi-port valves 1102.1-1102.n is implemented as a plurality of smaller multiport valves with fewer ports.

Existing commercial examples include matrix-valves which are nearly always implemented as valve complexes. An example of a commercial product implementation of matrix-valves is the R-Max™ Stream Switching Valve series (http://www.parker.com/ipd/cat/english/4140-R.pdf) manufactured by Parker Hannifin Corporation (Instrumentation Valve Division, 2651 Alabama Highway 21 North, Jacksonville, Ala. 36265, 256-435-2130). Most of these products are directed towards air and gas flow. Those directed to the control of fluids provide little at best in the way of preventing interspecies contamination.

Multiple-port valves and matrix valve systems can readily be fabricated as micro-scale structures readily incorporated into lab-on-a-chip structures. Some examples may be found in the following articles and the references therein:

Nelsimar Vandelli, Donald Wroblewski, Margo Velonis, and Thomas Bifano, "Development of a MEMS Microvalve Array for Fluid Flow Control," *Journal Of Microelectromechanical Systems*, Vol. 7, No. 4, December 1998, pp. 395-403.

John Collier, Donald Wroblewski, and Thomas Bifano, "Development of a Rapid-Response Flow-Control System Using MEMS Microvalve Arrays," *Journal Of Microelectromechanical Systems*, Vol. 13, No. 6, December 2004, pp. 912-922.

Jermaine White, "Fabrication of Polysilicon Micro Valve Array," 22nd Annual Microelectronic Engineering Conference, May 2004, pp. 90-93.

J. M. Quero, A. Luque, L. G. Franquelo, "A Novel Pressure Balanced Microfluidic Valve," *Proc. ISCAS* 2002, May 26-29, Phoenix, Ariz.

Because of the reciprocal (two-way) properties of constituent general single-port and multi-port valves, contemporary matrix valves typically permit bidirectional flow.

Reconfigurable Chemical Reaction Systems Utilizing Multiple-Port Selection, Distribution, Vector, and Matrix Valve Complexes with Clearing and Cleaning Provisions In contrast to the aforementioned commercially available controllable "valve manifolds" and matrix valves, some embodiments of the present invention employ multi-port valve structures, matrix valve structures, and related subsystems for the controllable routing chemical species, solvents, and cleaning gasses. It is therefore valuable for these multi-port valves, matrix valves, and related structures and subsystems to:

prevent interspecies contamination; and be arranged in such a way, or internally comprise capabilities for in situ cleaning of at least some portions of their internal flow paths.

Figure 12D:
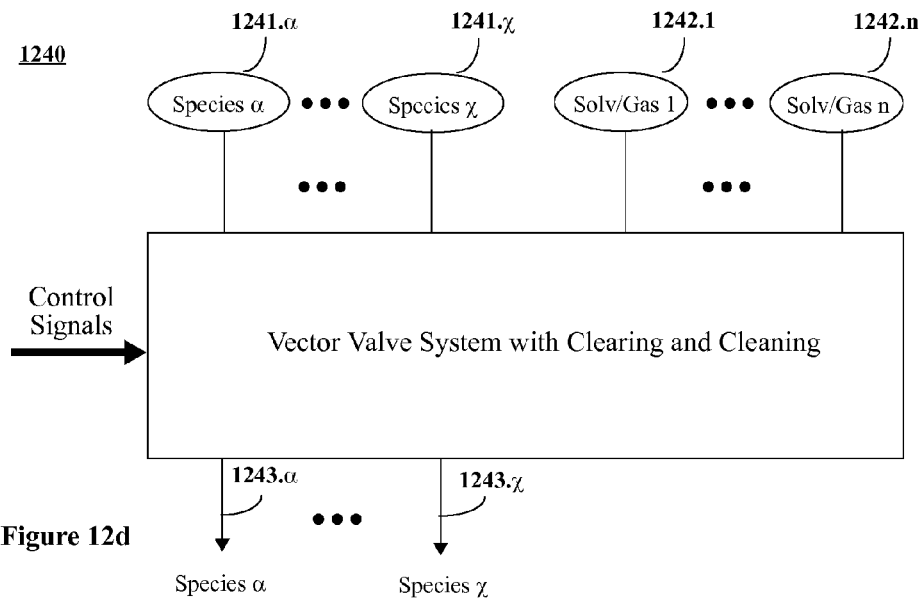

In many implementations, these added requirements (non-contamination and capabilities for in situ cleaning of at least some portions of their internal flow paths) introduce additional complexity into valve complexes. Among other things, this often results in multi-port valve and matrix valve structures that are non-reciprocal, i.e., the roles of inputs and outputs are not interchangeable. Thus, specialized valve structures often fall into several categories of non-reciprocal fluid and gas flow systems:

Selection multiple port valve structures or complexes 1210 where a number of chemical species 1211.α-1211.χ (and/or solvent and cleaning gas 1212.1-1212.n) inflow will need to be mutually exclusively directed to one outflow 1213, as depicted in FIG. 12a;

Distribution multiple port valve structures or complexes 1220 where one chemical species inflow 1221 (and/or solvent and cleaning gas inflows 1222.1-1222.n) will need to be individually or simultaneously directed to multiple outflows 1223.1-1223.n, as depicted in FIG. 12b;

Matrix valve structures or complexes 1230 where a number of chemical species 1231.α-1231.χ (and/or solvent and cleaning gas 1232.1-1232.n) inflows will need to be individually or simultaneously directed to multiple outflows 1233.1-1233.m, as depicted in FIG. 12c;

Vector multiple port valve structures or complexes 1240 where each of a number of chemical species inflows 1241.α-1241.χ (and/or solvent and cleaning gas 1242.1-1242.n) will each need to be individually or simultaneously directed to a respective outflow 1243.α-1243.χ that is uniquely associated with a corresponding inflow, as depicted in FIG. 12d.

These are then combined with other elements, such as those depicted in FIG. 8b, to create the basis for a reconfigurable chemical processing system.

Figure 12E:
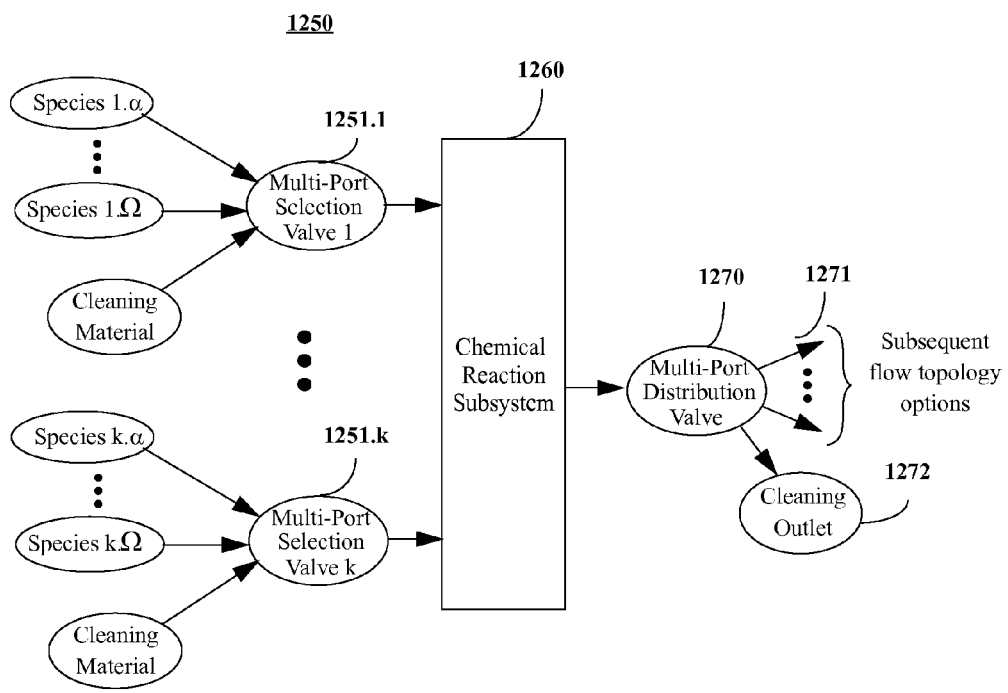

As an example of such a system, FIG. 12e depicts an arrangement 1250 involving a number of multi-port selection valves 1251.1-1251.k that are used to direct selected chemical species and cleaning materials into a chemical reaction subsystem 1260. Also included in this exemplary arrangement is a multi-port distribution valve 1270 providing a plurality of output paths 1271 as well as a cleaning outlet 1272. An exemplary application of this system 1250 is to sequentially produce chemical reaction products from various selected combinations of chemical species, directing these to respective subsequent flow destinations, and between each of the chemical reaction productions perform a cleaning cycle that may include the use of solvents and cleaning gases. One exemplary application of this is mixing a selected one of a number of acids with selected dilution agents (water, alcohols, etc.) and possibly other agents such as pH indicators or pH buffering solutions; multi-port valve 1 selects the chosen acid, multi-port valve 2 selects the dilution agent, etc.

Figure 13A:
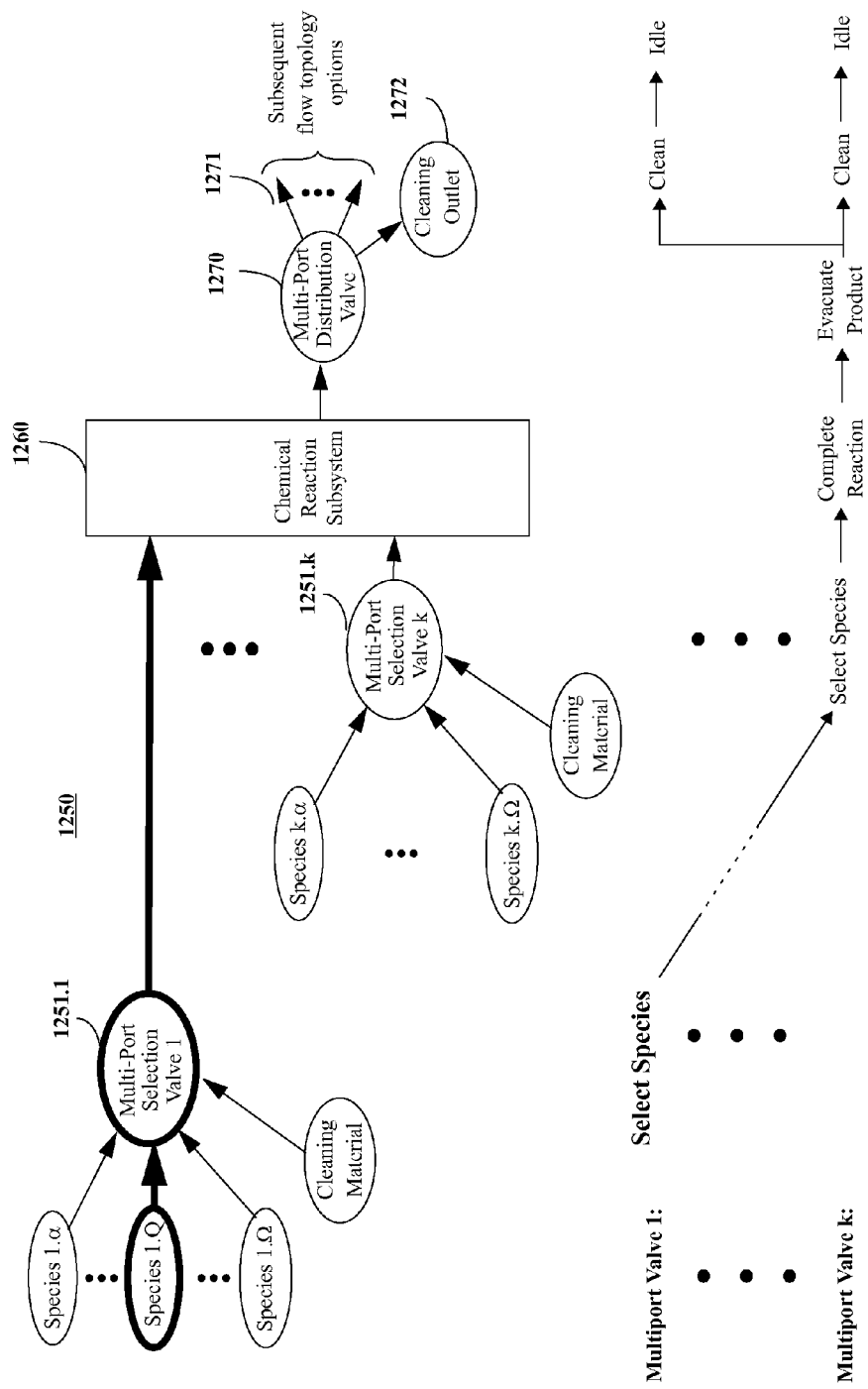
FIGS. 13a-13f highlight various uses of a multi-port selection valve.
Figure 13B:
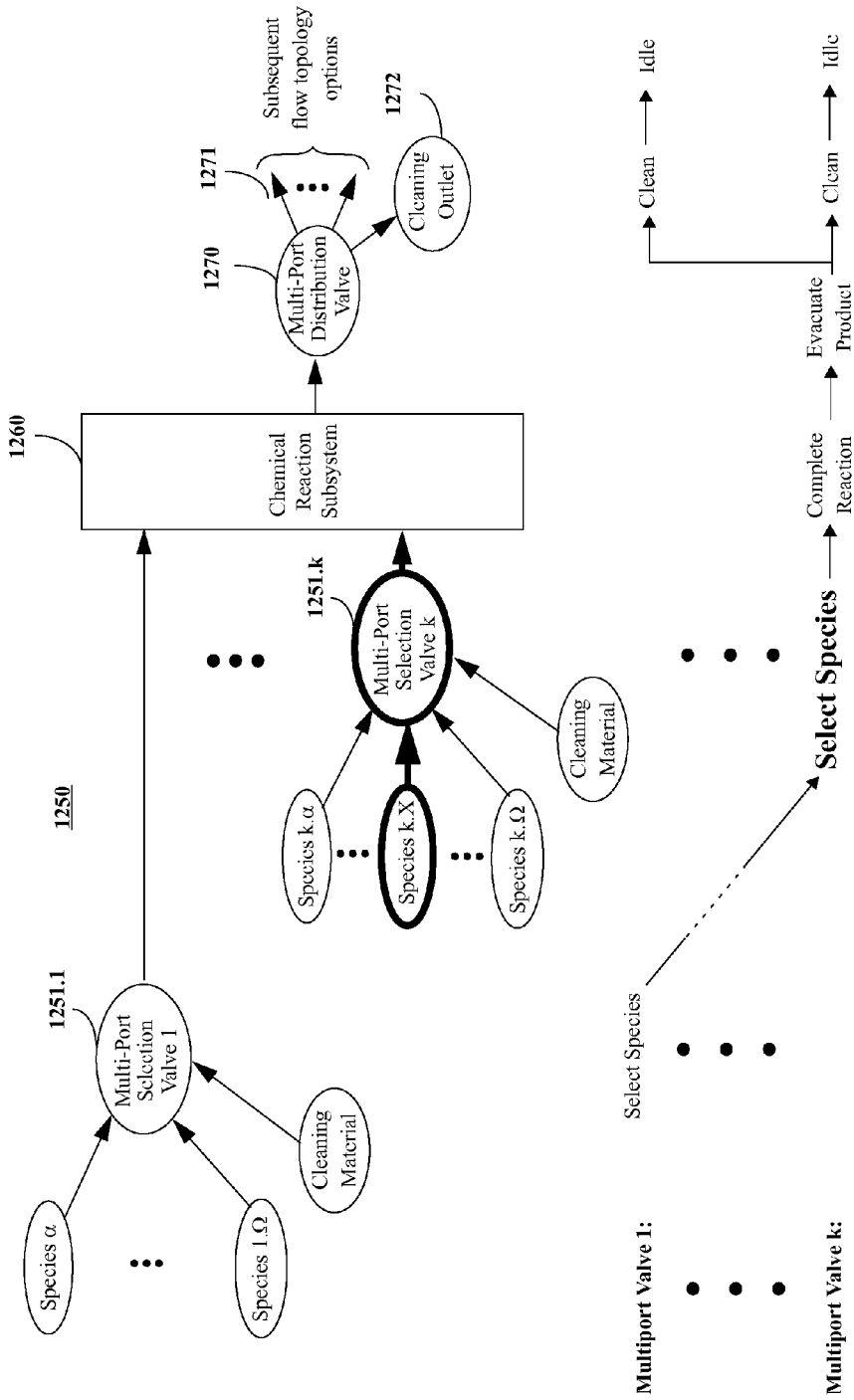
Figure 13C:
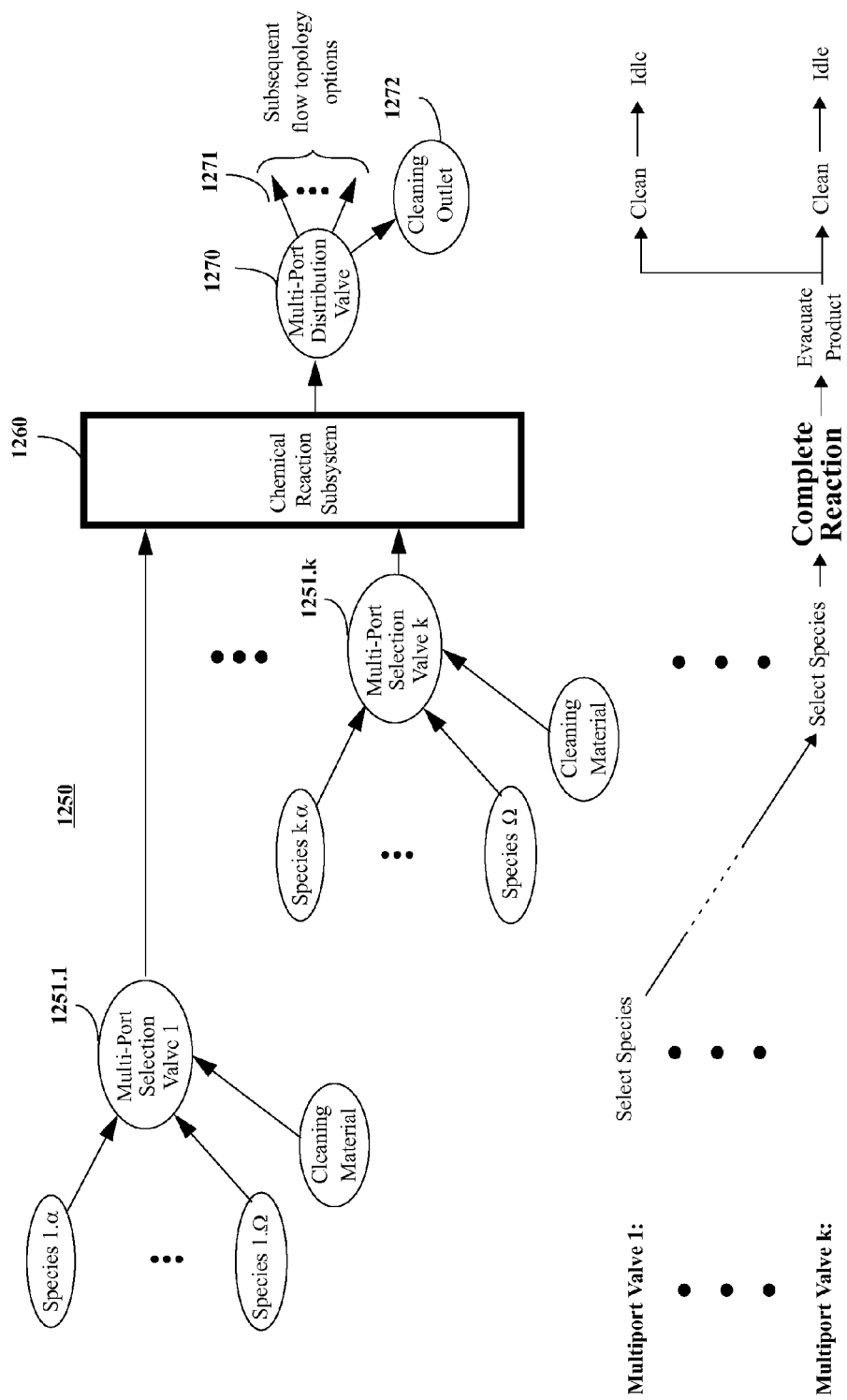
Figure 13D:
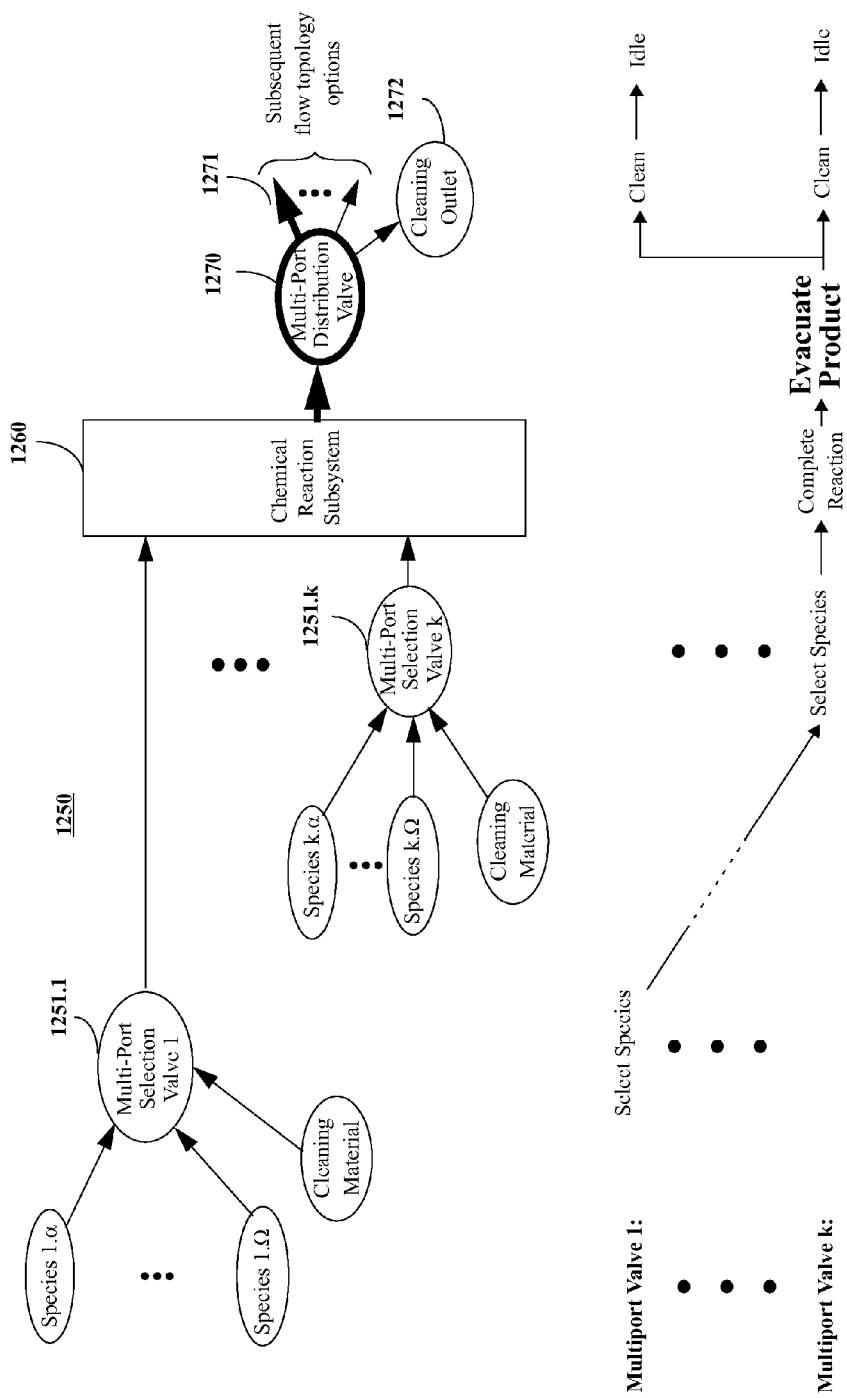

Utilizing the exemplary system of FIG. 12e, FIG. 13a highlights the use of multi-port selection valve 1 1251.1 to select a first chemical species from the group of species to the chemical reaction subsystem 1260. A similar action is performed by each of the other multi-port selection valves; for example FIG. 13b highlights the use of multi-port selection valve k 1251.k to select a first chemical species from the group of species to the chemical reaction subsystem 1260. The aforementioned operations of multi-port valve 1 1251.1 through multi-port valve k 1251.k may occur simultaneously, in a sequence of mutually exclusive actions, in a sequence of overlapping actions, or in combinations of these which further may comprise pauses, cycles, repetitive pulses, etc., as may be appropriate for the application. In FIG. 13c, the chemical reaction is shown to progress and settle with no additional inflow of chemical species. Subsequently, the resulting reaction product is evacuated from the chemical reaction system via outflow through the multi-port distribution valve 1270 to a first subsequent outflow destination 1271, as depicted in FIG. 13d.

With the product thus delivered, in situ clearing and cleaning can begin. A large number of possibilities exist for how this can be accomplished. In one example, each of the multi-port selection valves are cleared and cleaned in a manner such as that described shortly with their respective outflows flowing through the chemical reaction subsystem so as to clear and clean it as well, ultimately flowing to a cleaning outlet 1271 as enabled by the multi-port distribution valve 1270. In some implementations, the multi-port distribution valve 1270 may be open throughout so as to permit clearing (through the cleaning outlet 1271). In other implementations, multi-port distribution valve 1270 may close, at least momentarily, in order to accumulate solvents for interior rinsing. In some implementations, the multi-port distribution valve 1270 may periodically open and close.

The clearing and rinsing actions, by extension, can be used or further sequenced to clear and clean the multi-port distribution valve 1270 (in a manner such as that to be described shortly).

Figure 13E:
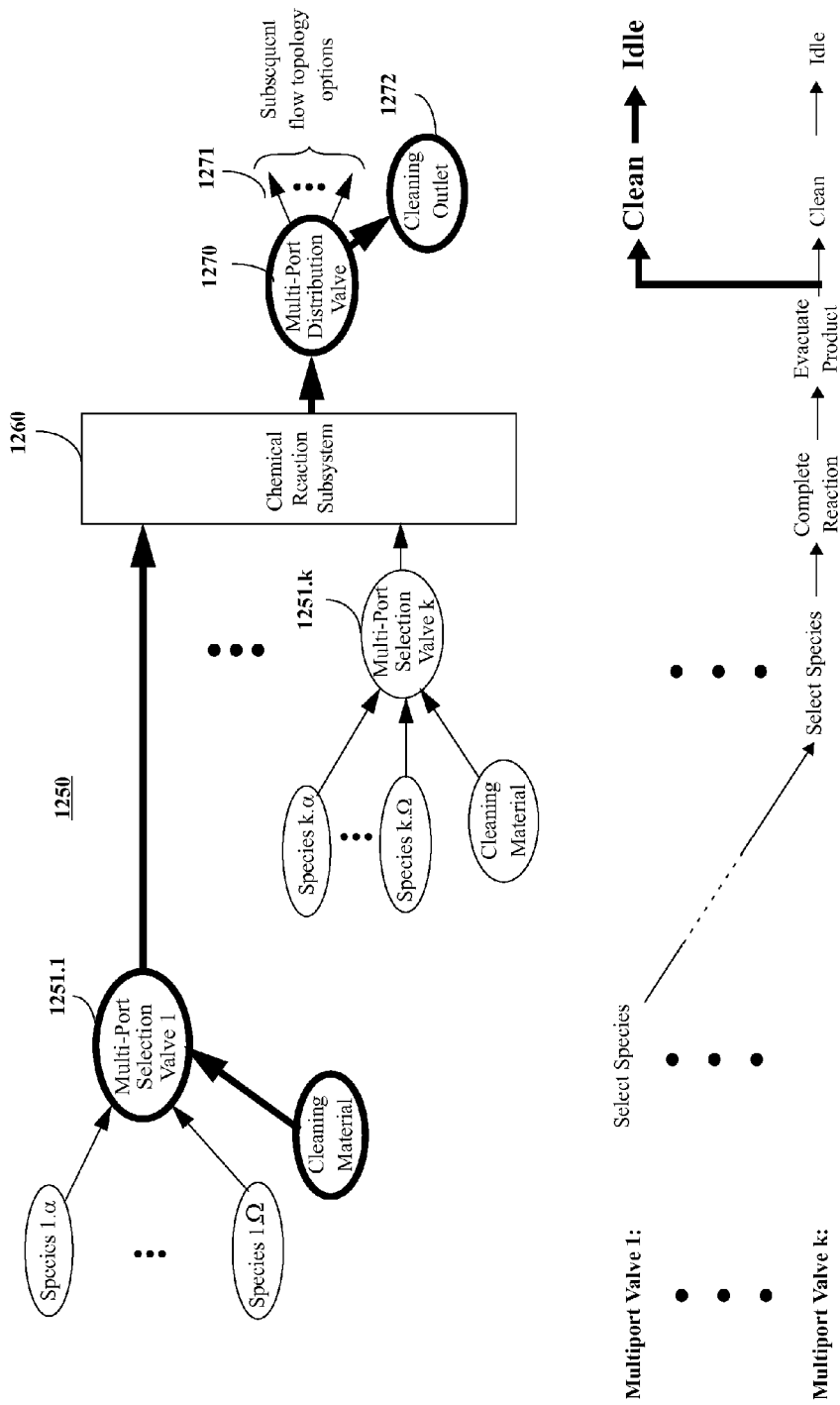
Figure 13F:
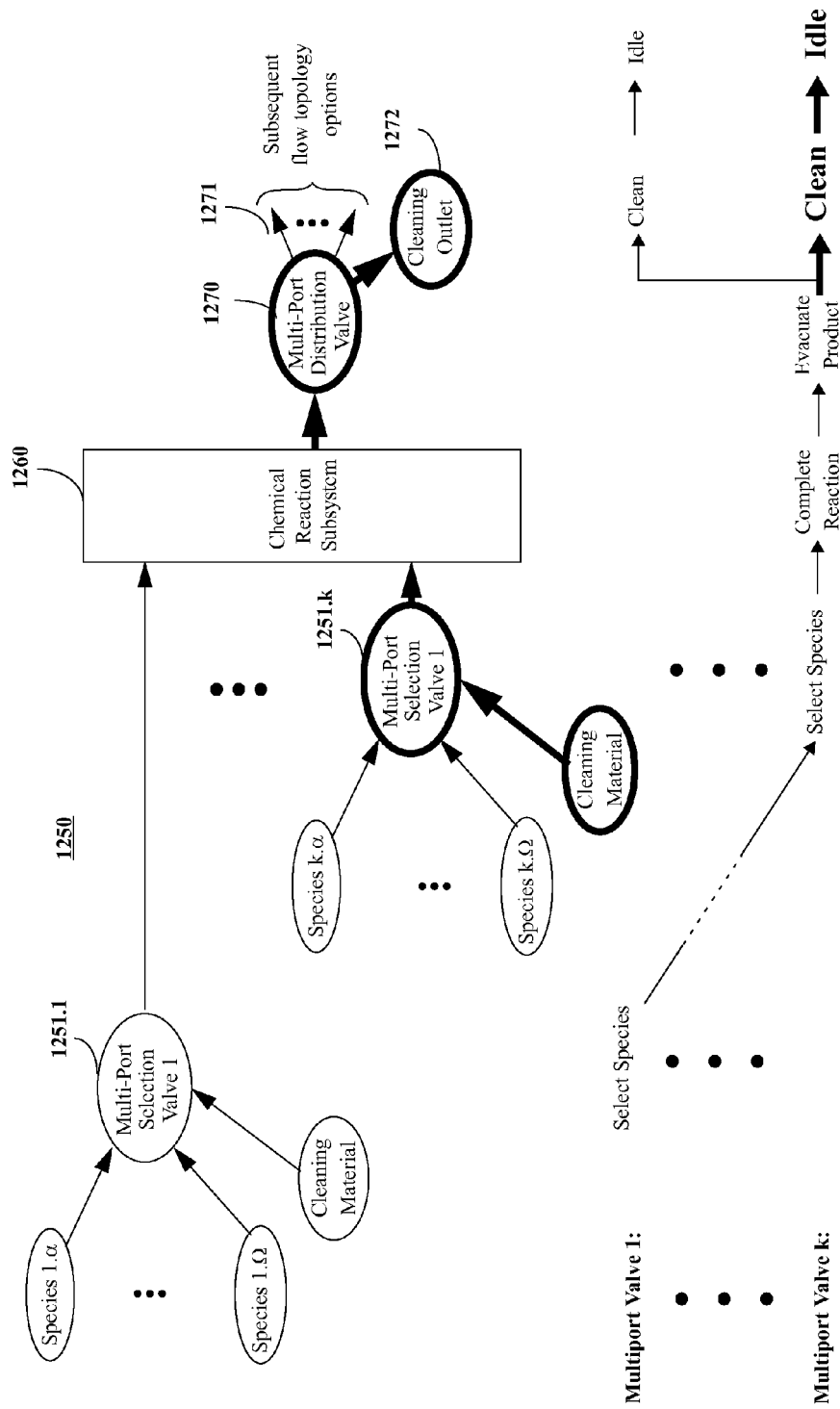

FIG. 13e shows a focus of such affairs with respect to multi-port selection value 1251.1, while FIG. 13f shows a similar focus with respect to multi-port selection value 1252.k.

As is clear to one skilled in the art, the arrangement depicted in FIG. 12e can be operated in any number of ways. The manner of operation just explained in conjunction with FIG. 13a-13f is only one possibility, and the cited selection of particular chemical species is arbitrary. Further, subsequent multi-port selection valves, multi-port distribution valves, and chemical reaction elements extend the controllable possibilities and create an overall reconfigurable chemical reaction system capable of implementing a wide range of chemical reaction networks.

Figure 14A:
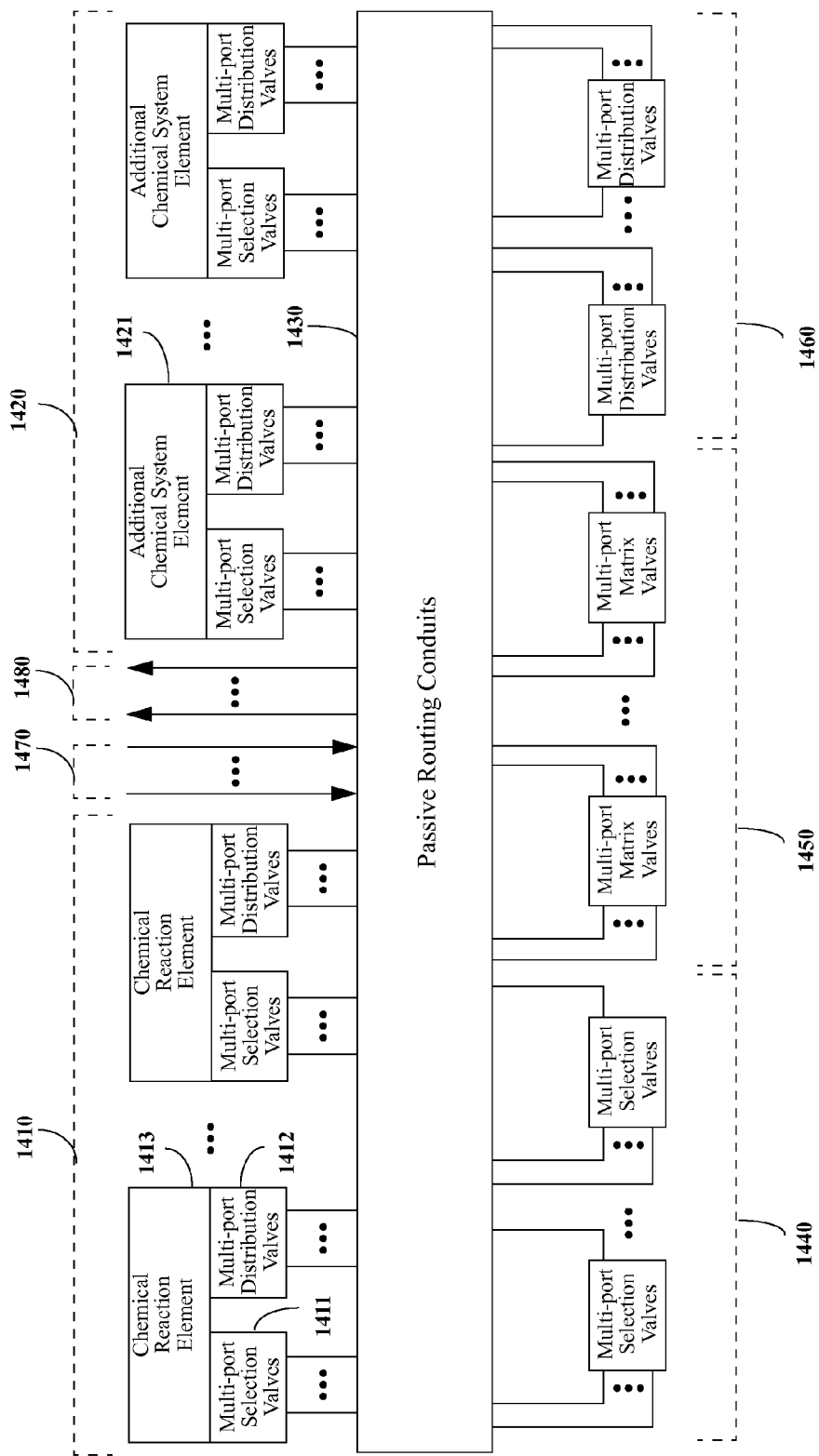
FIGS. 14a-14d depict exemplary larger-scale systems of arbitrary complexity and physical scale.

As to this, FIG. 14a depicts an exemplary larger-scale system of arbitrary complexity and physical scale as provided for by the invention. In this exemplary arrangement, a plurality of chemical reaction elements 1413 and associated multi-port selection and distribution valves 1410, together with a plurality of additional chemical system elements 1421 and associated multi-port selection and distribution valves 1420, are connected to a network of passive routing conduits 1430 which in turn connect with a plurality of multi-port selection valves 1440, multi-port matrix valves 1450, and multi-port distribution valves 1460. In this exemplary embodiment, input flows 1470 and output flows 1480 are also connected to the passive routing conduits 1430. As described earlier in conjunction with FIG. 8b, the additional chemical system elements 1421 may comprise one or more of the following:

Fluid and/or gas reservoirs 825,
Passive interconnection conduits 826,
Controllable valves 827,
Reaction chambers 828,
Heating and cooling elements 829,
Sensors 830,
Pumps 831,
Other (evaporators, condensers, mixers, agitators, bubblers, filters, flow constrictors, chromatography columns, electrophoresis elements, etc.)

as well as other types of elements.

Figure 14B:
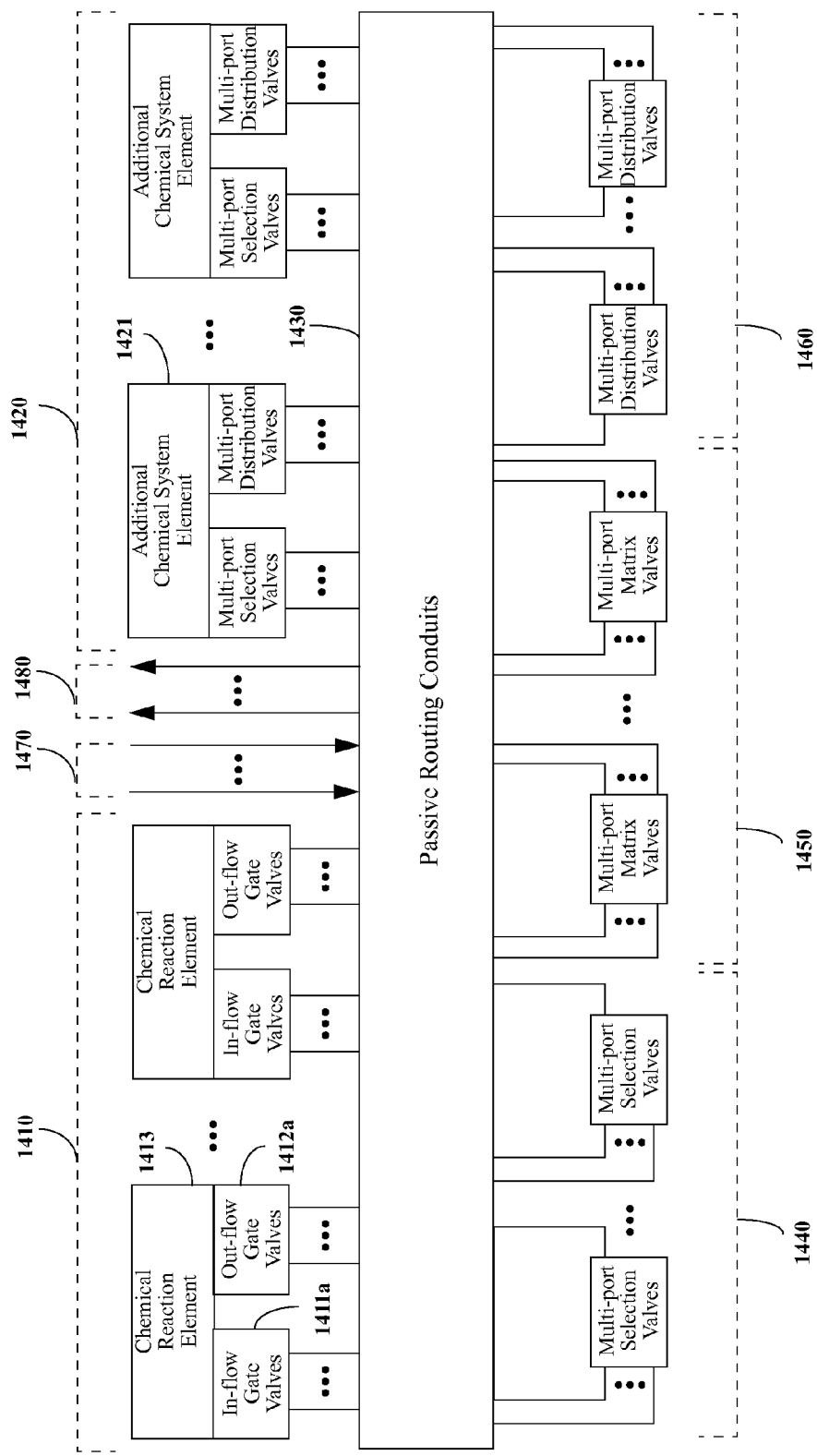
Figure 14C:
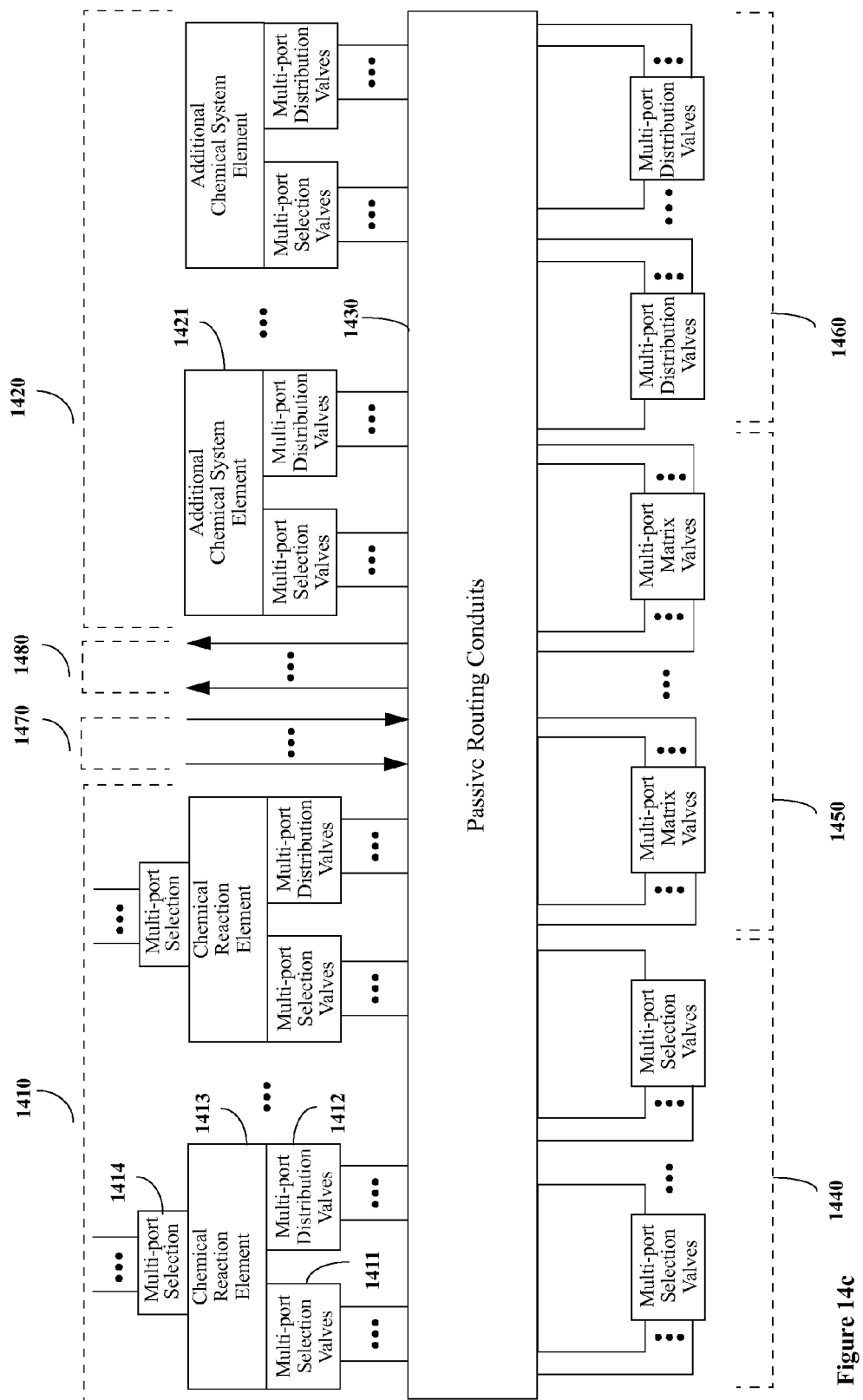

Further to the exemplary arrangement depicted in FIG. 14a, the multi-port selection valves 1411 and distribution valves 1412 associated with chemical reaction elements 1413 provide a first level of interfacing to the chemical reaction elements 1413. Other arrangements are possible as would be clear to one skilled in the art. In one example variation, shown in FIG. 14b, the chemical reaction elements 1413 could be provided only with inflow gate valves 1411a and outflow gate valves 1412a (to localize and contain chemical reactions and processes) and interface directly with the passive routing conduits 1430, and rely entirely on the plurality of multi-port selection valves 1440, multi-port matrix valves 1450, and multi-port distribution valves 1460 for all fan-out, fan-in, and routing. Many other variations are of course possible, for example feeding some species inflows directly into the chemical reaction elements 1413 by introducing associated multi-port selection valves 1414 as depicted in FIG. 14c. FIG. 14c suggests introduction of associated multi-port selection valves 1414 is applied to only and all of the chemical reaction elements 1413, but the could clearly be applied to only some of the chemical reaction elements 1413 and one or more of the additional chemical system elements 1421 as may prove advantageous in a particular implementation.

Not explicitly shown are provisions for clearing gas and cleaning solvent flows as were discussed earlier. As with the valve structures 1251.1-1251.k depicted in FIG. 12e, similar provisions for clearing gas and cleaning solvent flows may be integrated into at least the associated multi-port selection valves 1414. As in the example associated with FIG. 12e and its exemplary operation depicted in FIGS. 13a-13f, subsequent chemical reaction elements and distribution valves in a particular configuration may be cleaned from the resultant clearing gas and cleaning solvent flows originated at and controlled by these multi-port selection valves 1414.

Figure 14D:
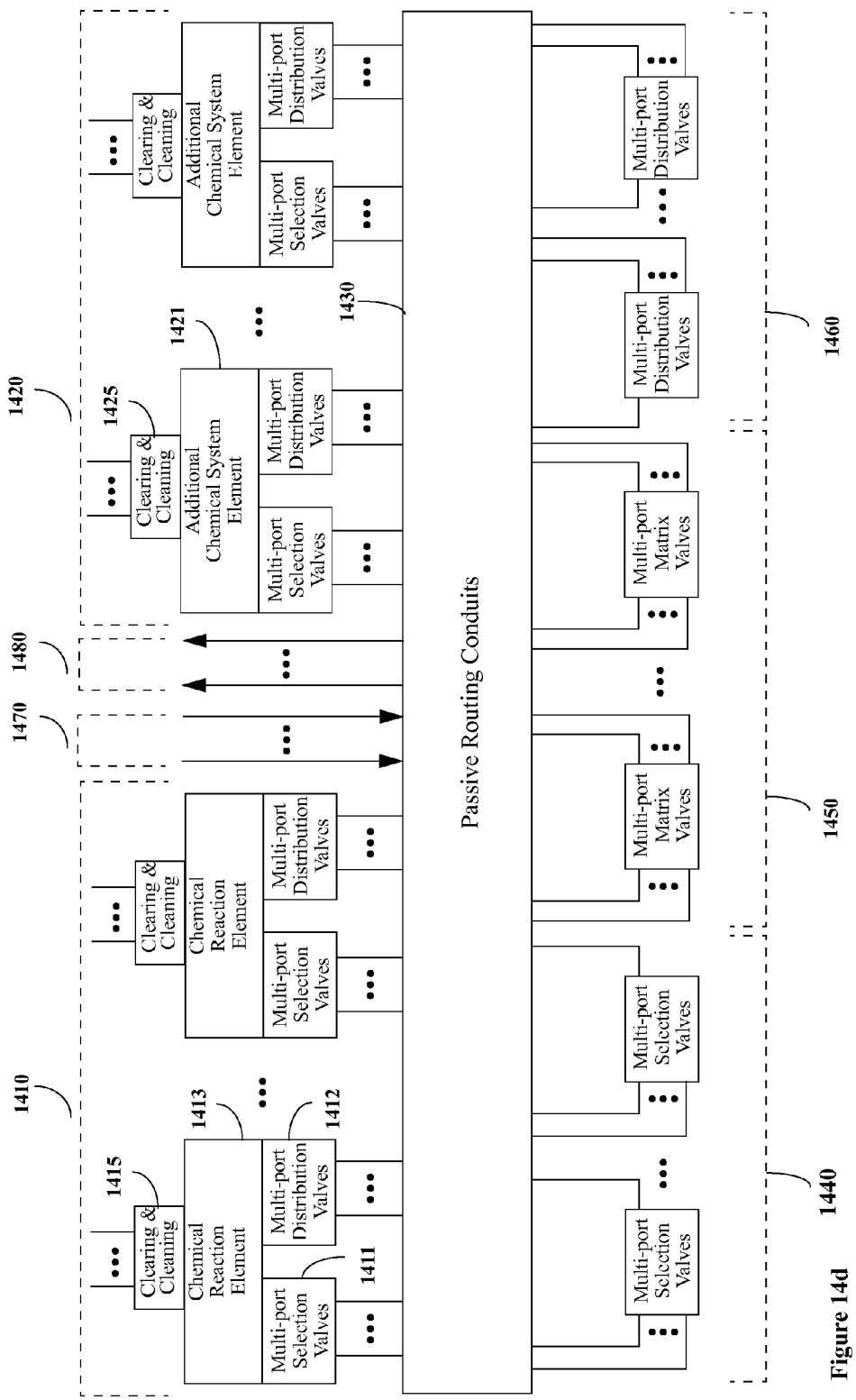

Alternatively, in another exemplary embodiment, chemical reaction elements 1413 and/or additional chemical system elements 1421 could be provided with separately implemented dedicated cleaning infrastructure, including separate valve systems 1415 and 1425 for clearing and cleaning material inflows and/or outflows as depicted in FIG. 14d.

General Control System Structures for Reconfigurable Chemical Reaction Systems

The control of such larger scale systems involves a significant number of localized operations that are coordinated at a higher level. As a result, overall systems control may be implemented in several ways, as is clear to one skilled in the art.

Figure 15A:
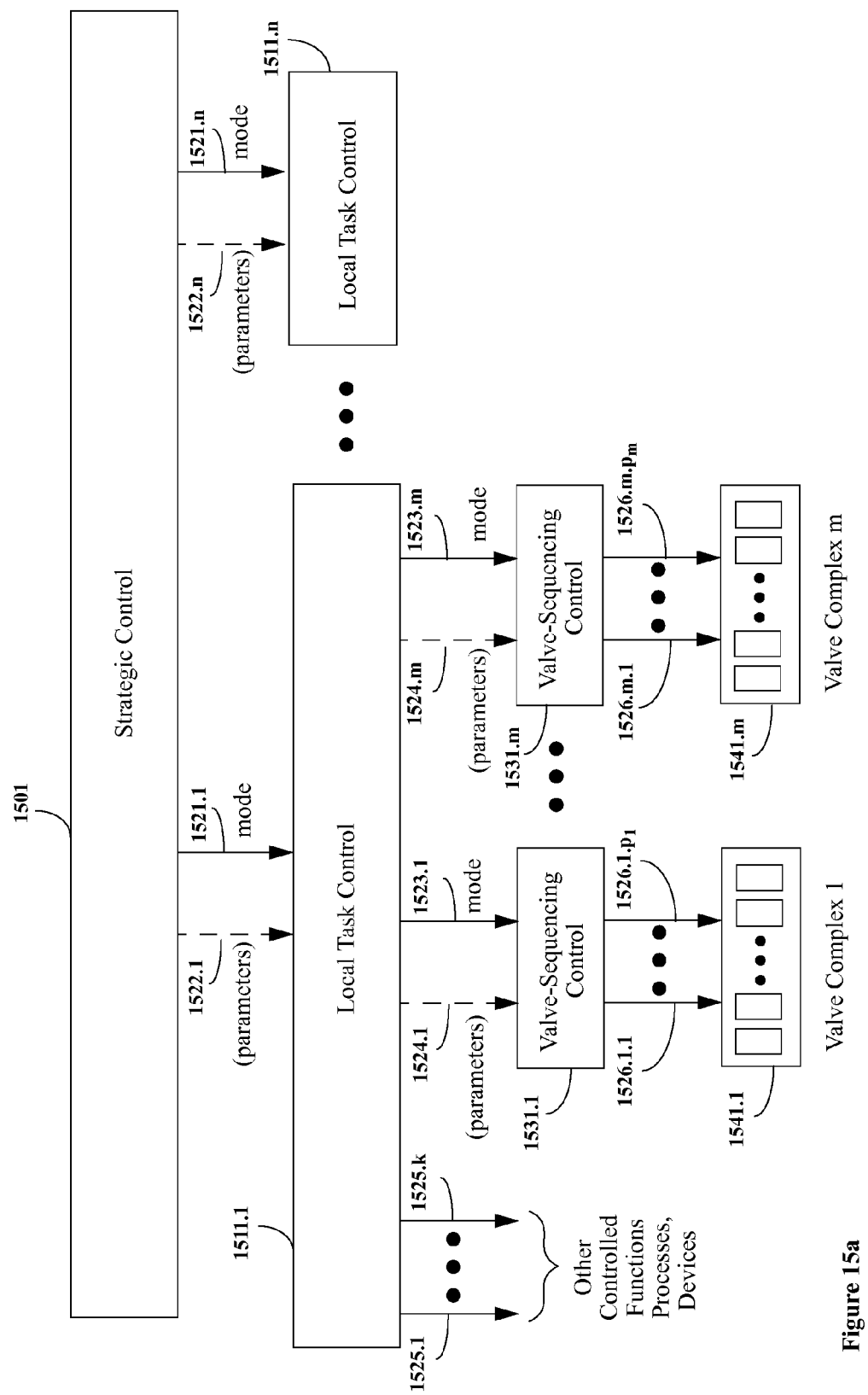
FIGS. 15a-15c illustrate exemplary control systems employing distributed computational task control.

FIG. 15a illustrates an exemplary control system embodiment employing distributed computational processing. This embodiment is structured to take advantage of the large number of localized tasks that would be typical of such a system as well as associated higher-level control and coordination. In this example, a strategic control entity 1502 provides high-level directions to one or more local task control entities. In the figure, a plurality of local control entities 1511.1-1511.$n$ are depicted. These control entities 1502 and 1511.1-1511.$n$ may comprise (software-executing computing) processors running software algorithms, (software-executing computing) processors running firmware algorithms, dedicated hardware, subroutines running on a multipurpose (software-executing computing) processor, or some combination of these. In this exemplary embodiment, the strategic control entity 1502 directs the Local Task Control entities 1511.1-1511.$n$ by communications that may include mode change commands 1521.1-1521.$n$, parameters 1522.1-1522.$n$, or other types of content. The Local Task Control entities 1511.1-1511.$n$ may additionally provide return communications to the Strategic Control entity 1502 which may comprise message acknowledgements, status indications, parameter returns, measurement values, etc.

The Local Task Control entities 1511.1-1511.$n$ in turn may, directly or indirectly, control valve complexes, heater elements, mixer elements, pumps, etc. For example, FIG. 15a shows a particular Local Task Control entity 1511.1 controlling a plurality of valve complexes 1541.1-1541.$m$ as well as providing control signals 1525.1-1525.$k$ to other controlled functions, processors, and devices. The valve complexes may be directly controlled by intervening Valve-Sequencing Control entity 1511.1 passing messages comprising mode control 1523.1-1523.$m$ and possibly parameter 1524.1-1524.$m$ These Valve Sequencing Control entities 1531.1-1531.$m$ may in turn send messages comprising acknowledgments, status, parameter, measurement and other information back to Local Task Control 1511.1. The Valve Sequencing Control entities 1531.1-1531.$m$ are shown providing control signals 1526.1.1-1526.1.$p_1$ through 1526.$m$.1-1526.$m.p_m$ to Valve Complexes 1541.1-1541.$m$. The Valve Complexes may in turn send message back to the Valve-Sequencing Control entities, or directly to Local Task Control entities or the Strategic Control entity 1501.

Figure 15B:
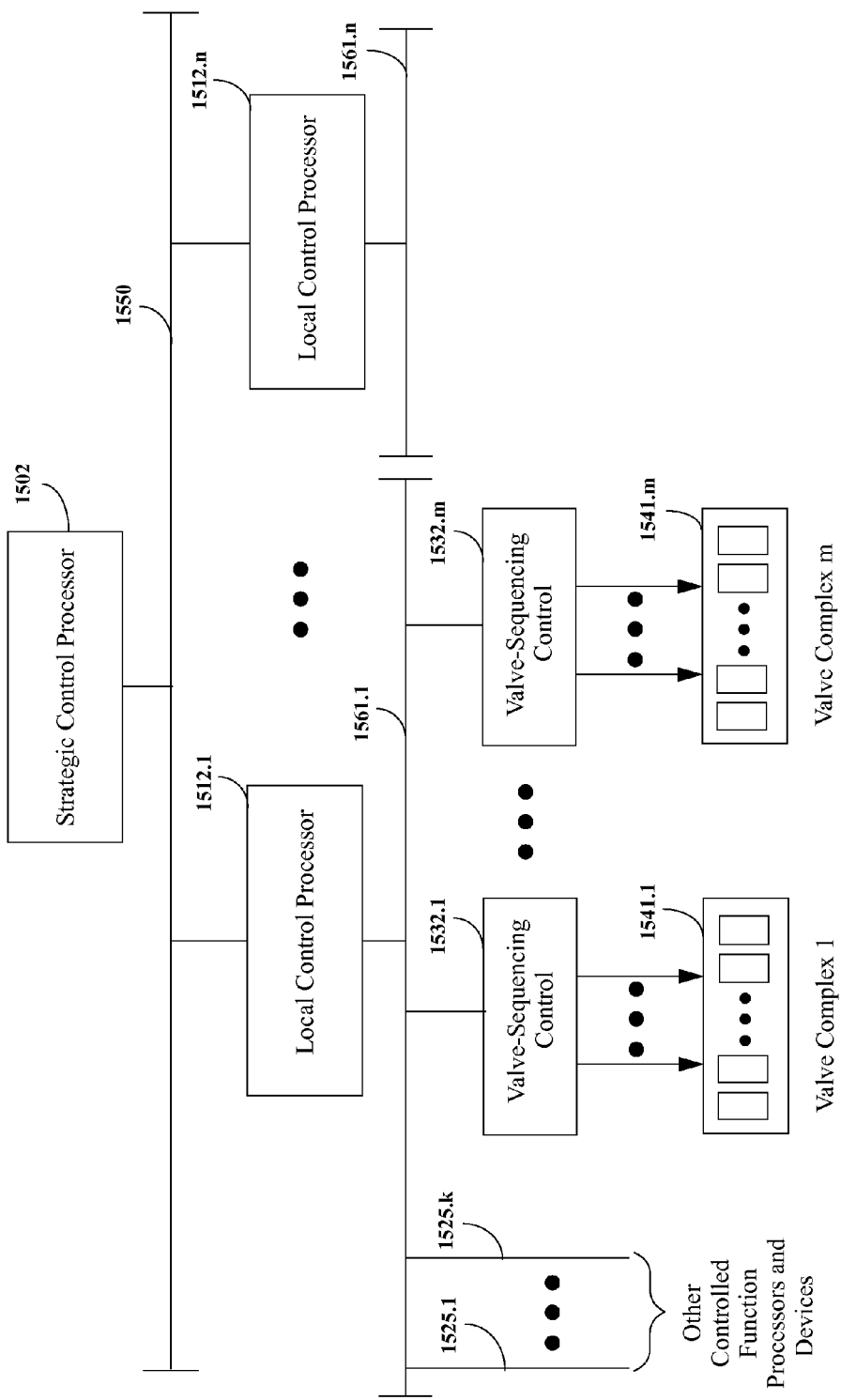

As mentioned, the exemplary Strategic Control entity 1501, Local Task Control entities 1511.1-1511.$n$, Valve-Sequencing Control entities such as 1531.1-1531.$m$, as well as other control entities responsive to additional control signals 1525.1-1525.$m$, may be implemented as software, subroutines, firmware, dedicated hardware, or combinations of these. FIG. 15b shows an exemplary embodiment where the various control entities are realized as or via corresponding (software-executing computing) processor elements 1502, 1512.1-1512.$n$, 1532.1-1532.$m$, etc. In this exemplary implementation, these (software-executing computing) processor elements may be interconnected with direct point-to-point paths, each uniquely corresponding to message paths, depicted in FIG. 15c, 1521.1-1521.$n$, 1522.1-1522.$n$, 1523.1-1523.$m$, and 1524.1-1524.$m$.

Figure 15C:
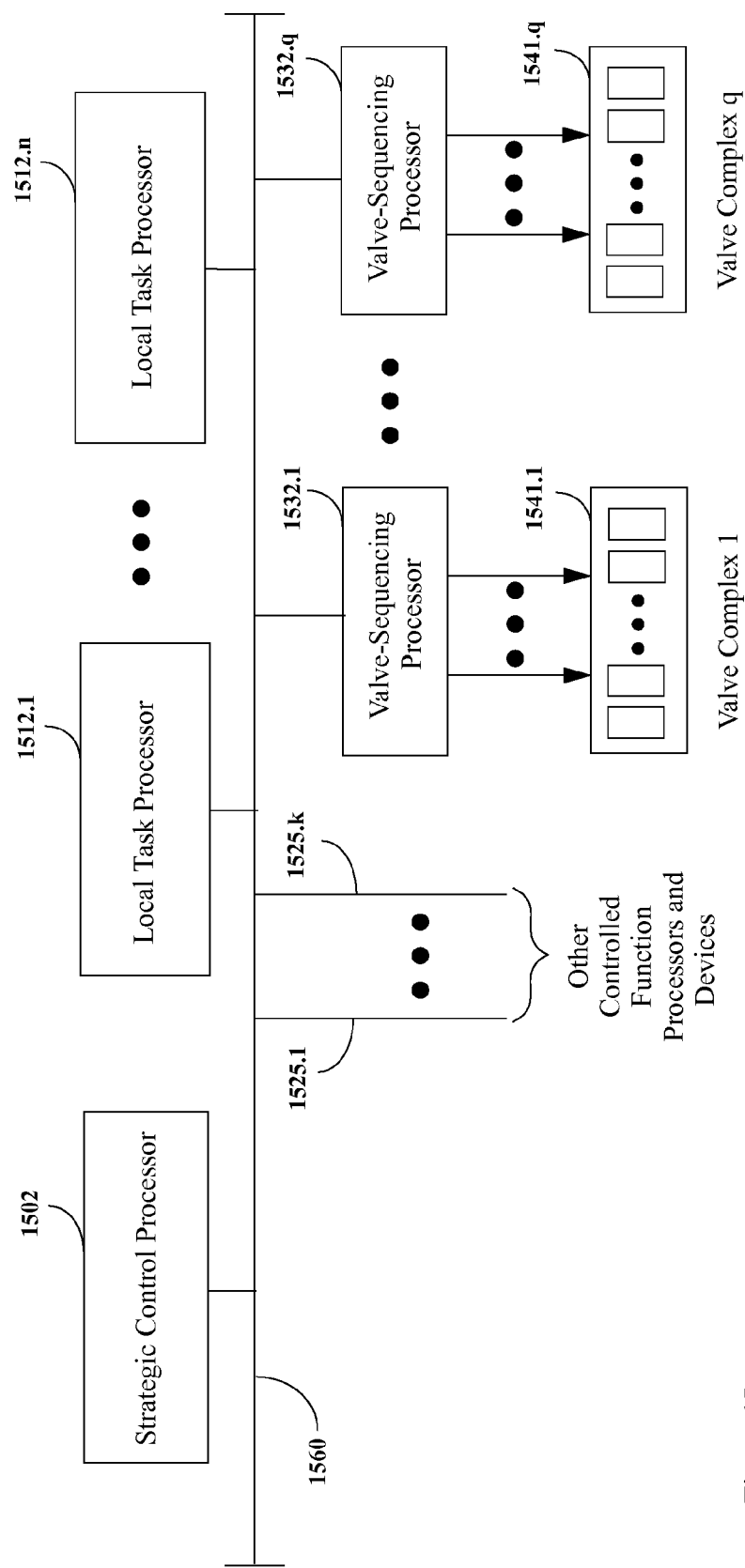

Alternatively, the (software-executing computing) processor elements (1502, 1512.1-1512.*n*, 1532.1-1532.*m*, etc. in FIGS. 15*b* and 15*c*) may be interconnected by various multipoint control signal interconnection schemes involving busses, rings, etc. This control signal interconnection may be electrical, optical, pneumatic, mechanical, chemical, or via other media. FIG. 15*b* illustrates an exemplary embodiment utilizing a bus 1550 interconnecting the Strategic Control Processor 1502 with the plurality of Local Task Control entities 1511.1-1511.*n*, and additional busses 1561.1-1561.*n* link to various elements controlled by and/or communicating with the respectively associated Local Control Processor 1512.1-1512.*n*. For example, FIG. 15*c* depicts Valve-Sequencing Processors 1532.1-1532.*q* in communication with Local Task Processor 1512.1 via a dedicated shared bus 1560. As one skilled in the art will understand, there are many possible variations and alternate implementation. For example, FIG. 15*c* depicts a case where various processors 1502, 1521.1-1521.*n*, 1532.1-1532.*q* in the control processor hierarchy communicate as needed on a global shared bus 1560. The example of FIG. 15*c* also shows the global shared bus 1560 providing additional control signals 1525.1-1525.*k*. In a similar manner, some or all of Valve Complexes 1541.1-1541.*q* may also communicate with associated processors 1532.1-1532.*q* over busses, including for example the local buses 1561.1-1561.*n* of FIG. 15*b* or the global shared control bus 1560 of FIG. 15*c*.

Exemplary Binary-Valve Multi-Port Selection Valve Complex and its Operation

Multi-port selection and distribution valves with in situ cleaning and clearing provisions may be implemented in various ways as will become apparent to one skilled in the art. For the sake of illustration, a number of examples are given constructed from simple two-state valves—in particular, simple binary (i.e., on-off) valves and simple two-way flow-redirection valves. These examples are relevant to lab-on-a-chip embodiments of the invention wherein considerable attention has been directed to the in-site fabrication of these simple micro-valve structures, particularly on-off valves. In addition to relatively straightforward photolithographic-based fabrication and a variety of schemes, two-state valves lend themselves well to binary control with digital signals. In some two-state valve implementations, energy is used to put a valve mechanism in a non-equilibrium state while no energy is used to operate the valve in the other (equilibrium) state. In other two-state valve implementations, the valve is mechanically bistable (i.e., possessing two equilibrium conditions) and energy is used only to change the valve state from one equilibrium condition to another.

Figure 16A:
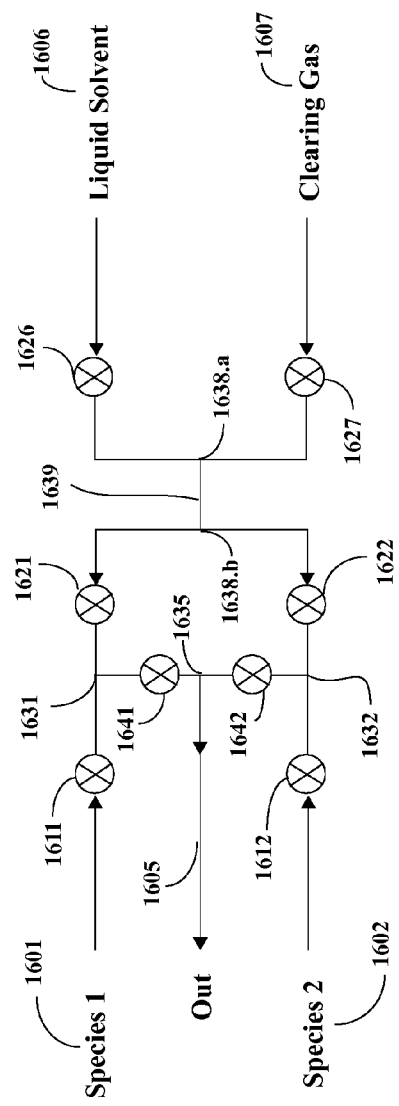
FIGS. 16a-16f depict exemplary valve complex arrangements.

As a first example, FIG. 16*a* depicts an exemplary valve complex comprising on-off valves providing a single outflow path from one of two source species 1601 and 1602 and providing exemplary in situ clearing, cleaning, and drying capabilities. The specific contamination behavior and liabilities of this configuration are examined. Clearing, cleaning, and drying modalities are developed for this and more general cases. FIGS. 18*a-g* depict a second exemplary valve complex configuration, also employing on-off valves, providing a single outflow path 1805 with a selection of one from among n source species and depicting slightly expanded exemplary in situ clearing, cleaning, and drying capabilities. The specific contamination behavior and liabilities of this second configuration will be considered in more detail below.

To begin, FIG. 16*a* illustrates a valve structure comprising eight simple on/off valves 1611, 1612, 1621, 1622, 1626, 1627, 1641, 1642 configured as an exemplary two-species multi-port selection valve with exemplary clearing, cleaning, and drying capabilities. In this exemplary implementation, the roles of the eight on-off valves 1611, 1612, 1621, 1622, 1626, 1627, 1641, 1642 may be grouped according to three general classes of functions: flow valves 1611, 1612, cleaning valves 1621, 1622, 1626, 1627, and gate valves 1641, 1642. The general and specific usage and operation of these will be described in detail in the discussion that follows for the selection and delivery of a particular species followed by subsequent clearing, cleaning, and drying.

Figure 16B:
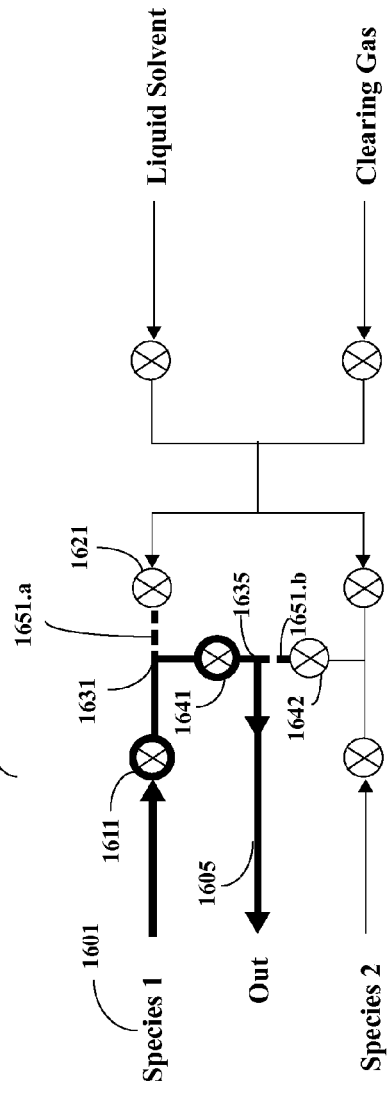

FIG. 16*b* illustrates the particular routine for the delivery of Species 1 from its source 1601 to the single outlet port 1605. Because of valve system symmetries, the case for the delivery of Species 2 is analogous. Note that this exemplary configuration requires both the Species 1 flow valve 1611 and Species 1 gate valve 1641 to be open for Species 1 to flow. Note that while the largest portion of Species 1 travels through these valves 1611 and 1641 and the associated paths in respective order to the outlet 1605, at least some degree of contamination 1651.*a* will typically occur between the joint 1631 into the region leading to the Species 1 clean valve 1621. Similar contamination liability is present in the region between the out path joint 1635 and the Species 2 gate valve 1642. The regions at risk for contamination are indicated with broken heavy line segments. Contamination events in these regions would typically occur due to splashing, turbulent-flow eddies, capillary action, and other effects. These contamination events typically result in at least a relatively minor loss of species, which can have an effect—albeit typically small—on the delivered volumes of species in a somewhat randomly-varying way. The first contamination region 1651.*a* may be addressed by a subsequent clearing and cleaning procedure, noting however that the in situ cleaning procedures themselves typically also introduce their own associated contamination effects. The second contamination region 1651.*b* can be more complicated to address with clearing and cleaning procedures as will be discussed.

With the delivery of a species complete, the valve system can pause for a period of time in an idle state. If the reaction is over and the valve system is to potentially be used to deliver a species other than the last species delivered, the previously used and related contaminated portions of a recently employed valve system are usually advantageously cleared, cleaned, and dried. Clearing, cleaning, and drying operations are described further as follows:

Clearing involves use of a gas, to be referred to as a "clearing gas," to blow through relevant valves and paths as well as either through or into contaminated areas. The bulk of the residual species or reaction products are in this way removed. In some implementations, clearing operations may be adapted to recover unused species for reuse that would otherwise be wasted. In some cases the clearing gas would be chosen so as to be non-reactive to residual species and reaction products. In other cases, any reaction that may occur between residues and the clearing gas (such as oxidation, should air be used) are of no concern as the results will subsequently be rinsed away.

Cleaning, in its simplest form, involves the flow of a volatile (i.e., readily evaporative) liquid solvent to rinse through relevant valves and paths as well as either through or into contaminated areas. The remaining residual species or reaction products are in this way removed. The residue-laden rinsing solvent may be treated as waste or, in some implementations, be directed to solvent recovery systems and procedures. In more complex implementations, cleaning may involve multiple liquids used in a more complex cleaning sequence, including operations involving chemically neutralizing agents, emulsifiers, etc.

Drying involves use of a gas, to be referred to as a "drying gas," to blow through relevant valves and paths as well as either through or into contaminated areas. In many cases the drying gas would be chosen so as to be non-reactive and/or relatively non-absorptive to future species and reaction products that will be later exposed to it. Drying gas may also be involved in transport processes for fluid species. In some implementations, the drying gas may be identical to the clearing gas (for example, both may be filtered air) and share the same source. In some versions of those implementations, the drying gas may be first subjected to additional operations, such as desiccant processing and/or heating.

Figure 16C:
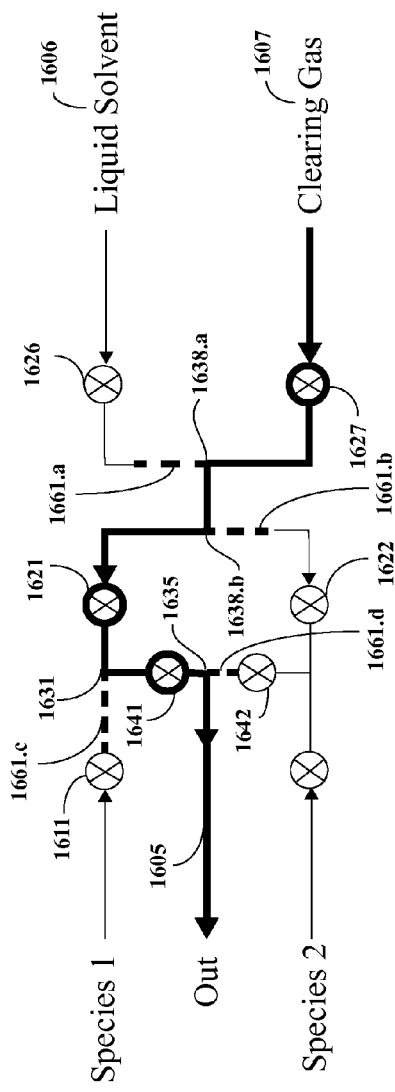

FIG. 16c illustrates the Species 1 clearing gas operation. Because of valve system symmetries, the case for the delivery of Species 2 is analogous. Clearing gas valve 1627, Species 1 clean valve 1621, and Species 1 gate valve 1641 are opened and the clearing gas flows through the associated valves and transport paths and by the associated path joints. The clearing gas flows for an interval sufficient to clear the bulk of remaining species or reaction product content and residue. The clearing process can be improved in some implementations by invoking turbulence in the flow of the clearing gas. This could be done by temporally and/or spatially modulating the pressure of the clearing gas, by introducing turbulence-provoking structures in the paths and channels, or by other means.

Note the clearing gas operation depicted in FIG. 16c is ineffective in Region 1661.b between the Species 2 clean valve 1622 and the joint 1638.b. In this valve complex design this ineffectiveness is acceptable as in fact the Species 1 gate valve 1635 localizes the Species 1 content away from the outlet path 1605.

Also note that the clearing gas operation depicted in FIG. 16c can, depending on the detailed embodiment of the valve complex, be a source of additional contamination. For example, in the presently discussed valve complex, clearing gas travel through the valves and associated paths mentioned can easily blow adjacent residue into region 1661.d between the joint 1635 and the Species 2 gate valve 1642. This would cause at least some degree of contamination, as indicated with broken heavy line segments. Additionally, note that the clearing gas can propagate, with far less consequence, into the following regions, indicated with broken heavy line segments:

Region 1661.a between the joint 1638.a and the solvent valve 1626;

Region 1661.c between the joint 1631 and the Species 1 flow valve 1611.

Figure 16D:
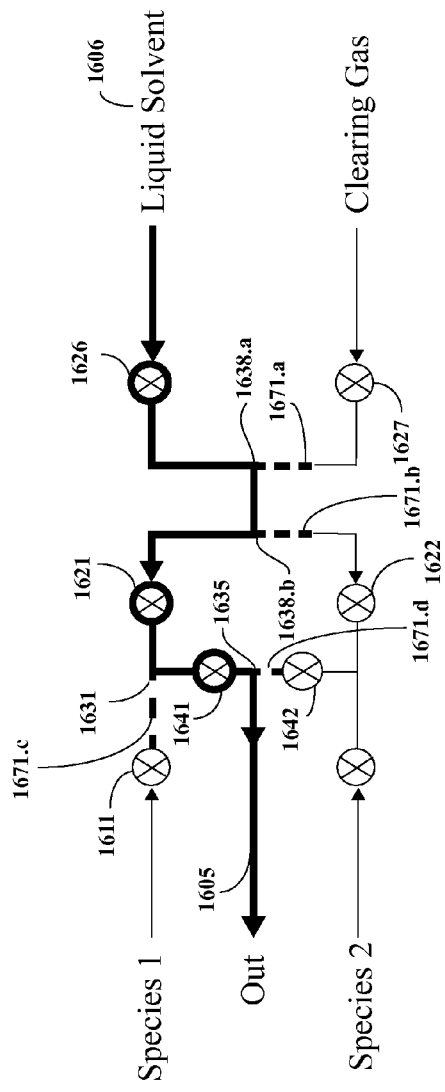

Next, FIG. 16d illustrates an embodiment of a Species 1 solvent cleaning operation. Because of valve system symmetries, the case for the delivery of Species 2 is analogous. This operation involves opening Solvent valve 1626, Species 1 clean valve 1621, and Species 1 gate valve 1641 so that rinsing of valves 1621 and 1635, along with associated paths, can occur. The resulting liquid solvent flows for an interval sufficient to remove the remaining residual species or reaction product content. The solvent cleaning process can be improved in some implementations by invoking turbulence in the flow of the liquid solvent. This could be done by temporally and/or spatially modulating the pressure of the clearing gas, by introducing turbulence-provoking structures in the paths and channels, or by other means. Additionally, more than one type of solvent may be made available, and these may be used as alternatives, in sequence, or in a mix as may be advantageous in various applications and embodiments.

Further, the available liquid solvents and the liquid solvent infrastructure in the valve complex may be supplemented with additional functional liquids such as chemically neutralizing agents, emulsifiers, etc.

While liquid solvent travels through the valves and associated paths in the operation depicted in FIG. 16d, at least some degree of additional contamination can occur in the following regions of concern, indicated with broken heavy line segments:

Region 1671.c between the joint 1631 and the Species 1 flow valve 1611;

Region 1671.d between the joint 1635 and the Species 2 gate valve 1642.

Note liquid solvent contamination into region 1671.c can dilute or corrupt the leading Species 1 material that may be delivered in a subsequent Species 1 flow operation. Similarly, liquid solvent contamination into region 1671.d can dilute or corrupt the leading Species 2 material that may be delivered in a subsequent Species 2 flow operation.

Additionally, with far less consequence, note the clearing gas can propagate into the following regions, indicated with broken heavy line segments:

Region 1671.a between the joint 1638.a and the clearing gas valve 1627;

Region 1671.b between the joint 1638.b and the Species 2 cleaning valve 1622.

These may cause sputtering of residual solvent in the onset of later clearing gas flow.

Figure 16E:
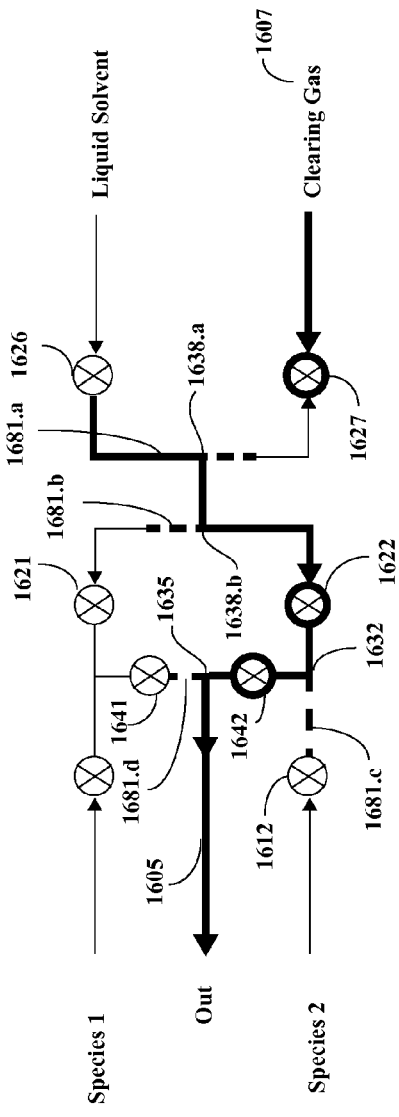

As an illustration of how some of the contamination concerns raised above could be addressed, FIG. 16e illustrates a clearing gas operation that is the Species 2 version of the clearing gas operation depicted for Species 1 in FIG. 16c. It is brought forward here to demonstrate its utility in reducing some of the contamination induced by the solvent cleaning operation of FIG. 16d. In contrast to FIG. 16c, Species 2 clean valve 1622 and Species 2 gate valve 1642 operate. The flow of clearing gas blows out the bulk of the contamination introduced into regions 1671.b and 1671.d depicted in FIG. 16d. However, this operation introduces its own associated contamination effects by blowing adjacent residue into the following regions, indicated with broken heavy line segments:

Region 1681.c between the joint 1632 and the species 2 flow valve 1612;

Region 1681.d between the joint 1635 and the Species 1 gate valve 1641.

Additionally, note that the clearing gas can propagate—again with far less consequence—into the following regions, indicated with broken heavy line segments:

Region 1681.a between the joint 1638.a and the solvent valve 1626;

Region 1681.b between the joint 1638.b and the species 1 clean valve 1621.

Figure 16F:
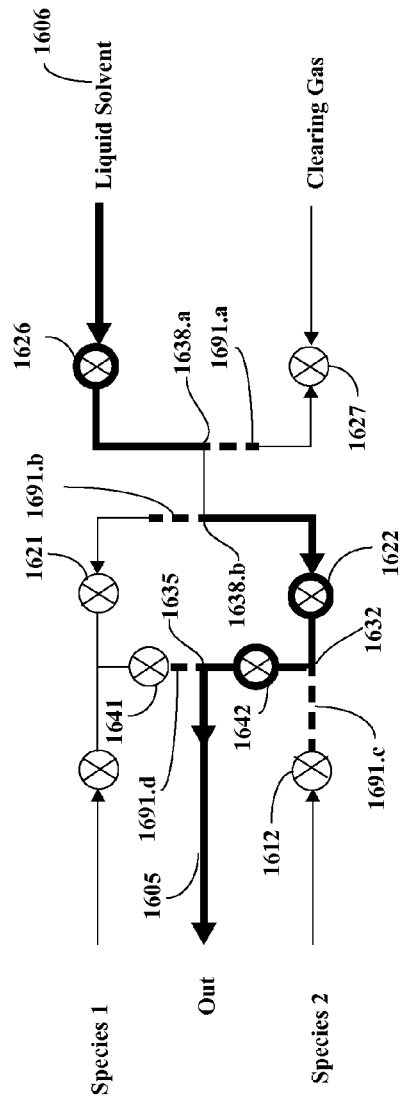

Similarly, FIG. 16f repeats the operation of FIG. 16e but for liquid solvent rather than clearing gas. FIG. 16f illustrates a solvent cleaning operation that is the Species 2 version of the clearing gas operation depicted for Species 1 in FIG. 16d, and is brought forth here to demonstrate its utility in reducing some of the contamination induced by the solvent cleaning operation of FIG. 16d. Here, Species 2 clean valve 1622 and Species 2 gate valve 1642 are opened. The flow of liquid solvent removes remaining contamination residue in regions 1671.b and 1671.d depicted in FIG. 16d. However, this operation introduces its own associated contamination effects by blowing residue into the following regions, indicated with broken heavy line segments:

Region 1691.c between the joint 1632 and the Species 2 flow valve 1612;

Region 1691.*d* between the joint 1635 and the Species 1 gate valve 1641.

Additionally, note that the clearing gas can propagate—yet again with far less consequence—into the following regions, indicated with broken heavy line segments:

Region 1691.*a* between the joint 1638.*a* and the clearing gas valve 1627;

Region 1691.*b* between the joint 1638.*b* and the Species 1 clean valve 1621.

After clearing gas and cleaning solvent operations are performed in a given portion of the valve complex, a drying gas operation is used to dry out the remaining volatile solvent. In many cases, the clearing gas chosen can also act as drying gas. In this situation, the drying gas operation would be like that depicted in FIGS. 16*c* and 16*e*. In other embodiments an alternate type of drying gas, differing in some way from the clearing gas, may be employed. This would require either a gas selection operation prior to gas valve 1627, an additional valve-controlled gas flow into (or into the vicinity of) joints 1638.*a* or 1638.*b*, or other provisions.

General State-Transition Model for Multiple Primitive-Valve Complex Operation

The exemplary operations depicted in FIGS. 16*a*-16*f* can be abstracted into a general state-transition operational model for multi-port selection valves with such in situ clearing, cleaning, and drying capabilities.

Figure 17A:
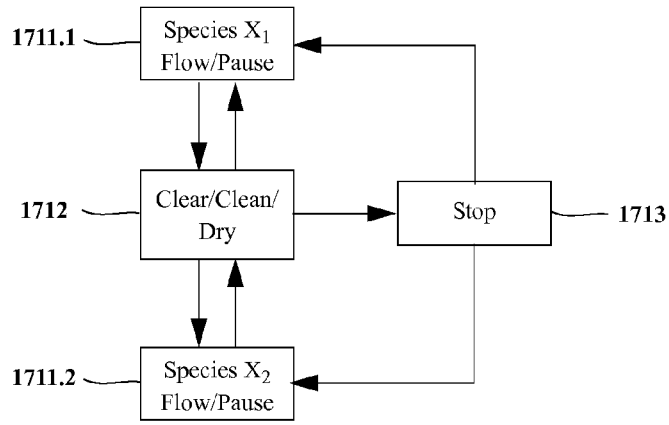
FIGS. 17a-17d depict exemplary abstracted views of an exemplary operation of a multiple-species system such as that depicted in FIGS. 16a-16f.

To begin, FIG. 17*a* depicts an exemplary highly simplified view of the two-species example depicted in FIGS. 16*a*-16*f*. Such a highly simplified view would be one seen by an operator or higher-level operational software: choose a species, letting it flow and pause as needed (for measurement, mixing, production operation repetition, etc.), cleaning, and stopping. In this exemplary simplified view, four "high-level state-clusters" are depicted:

Species 1 Delivery (flow and pause) 1711.1;
Species 2 Delivery (flow and pause) 1711.2;
Clear/Clean/Dry 1712;
Stop 1713.

However, as seen in the example depicted in FIGS. 16*a*-16*f*, details of Clear/Clean/Dry operations 1712 advantageously depend upon the specific species previously selected for delivery. This suggests that in a more general model, the Clear/Clean/Dry high-level state-cluster 1712 would need to be partitioned. Further, within three of the four high-level state-clusters there is additional state-transition structure.

Figure 17B:
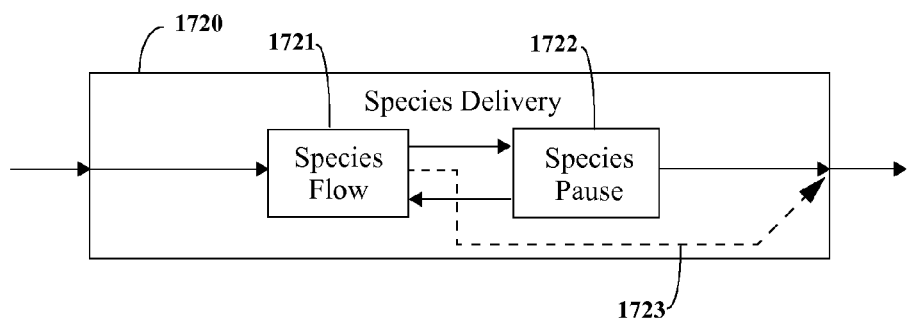

FIG. 17*b* shows an exemplary decomposition of a general Species Delivery high-level state-cluster and the additional state-transition structure within. Upon entering the general Species Delivery high-level state-cluster 1720, the associated species is allowed to flow 1721. After the allotted time, the species flow is interrupted and the valve complex is put into a pause state 1722. From the pause state 1722, flow of the same species can restart, or delivery of that species can be ended, corresponding to leaving the Species Delivery high-level state-cluster 1720. In some implementations it may be advantageous to have a transition from the species flow state 1721 directly out of the Species Delivery high-level state cluster 1720 with no intervening pause state 1722. This is depicted by the dashed state-transition path 1723.

Figure 17C:
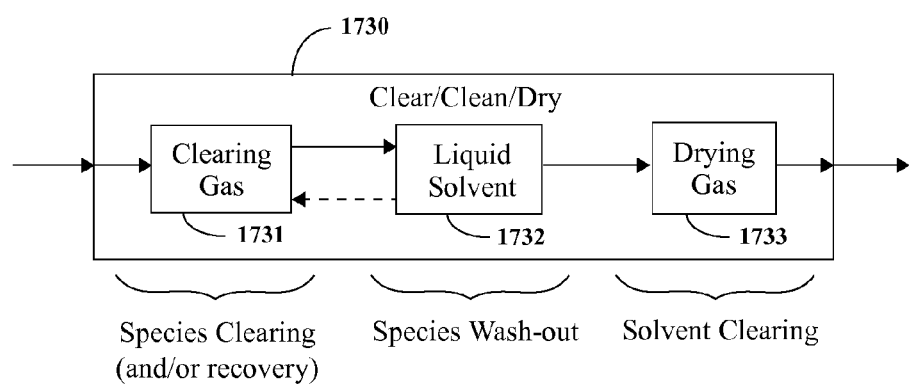

FIG. 17*c* shows a simple exemplary decomposition of the Clear/Clean/Dry high-level state-cluster. Upon entering the Clear/Clean/Dry high-level state-cluster 1730, a clearing gas 1731 is applied to clear out any residual species that may remain in valves and interconnecting transport paths. Next at least one (typically volatile) liquid solvent 1732 is sent through the valves and interconnecting transport paths that were just cleared. The solvent provides wash and rinse to the valves and interconnecting transport paths that were just cleared. As in the exemplary phases of additional contamination clearing and cleaning operations associated with FIGS. 16*e* and 16*f*, there may be subsequent iterations of transitions between cleaning gas flow 1731 and liquid cleaning solvent flow 1732. There also may be a sequence of solvents, chemically neutralizing agents, emulsifiers, etc., and these may or may not have intervening episodes of clearing gas (and/or even drying gas). For liquid solvents that are sufficiently volatile, a drying gas 1733 (which in some implementations may be the same gas used for clearing) is next used to dry away the residual solvent remaining in the valves and interconnecting transport paths. Should a liquid solvent not be volatile enough to be dried by a gas, it may instead be cleared with a subsequent clearing gas action, or cleaned with a second solvent, emulsifier, etc. Further, the flows of clearing gas(es) 1731, liquid solvent(s) 1732, and drying gases 1733 may be modulated in time (for example, rapidly pulsed at one or more appropriate pressure-varying frequencies) or otherwise agitated so as to more effectively cause the removal of residue left in the associated valves and transport paths. Other alternate and more complex behavior and capabilities as would be clear to one skilled in the art are also provided for by the invention.

Additionally, as seen in the example of FIGS. 16*a*-16*f*, the Clear/Clean/Dry high-level state cluster typically may advantageously leverage knowledge as to which of the two species most recently flowed so only the relevant portions of the valve complex are cleared, cleaned, and dried. This suggests associations between pairs of Species Delivery 1720 and Clear/Clean/Dry high-level state clusters, one pair for each species.

Figure 17D:
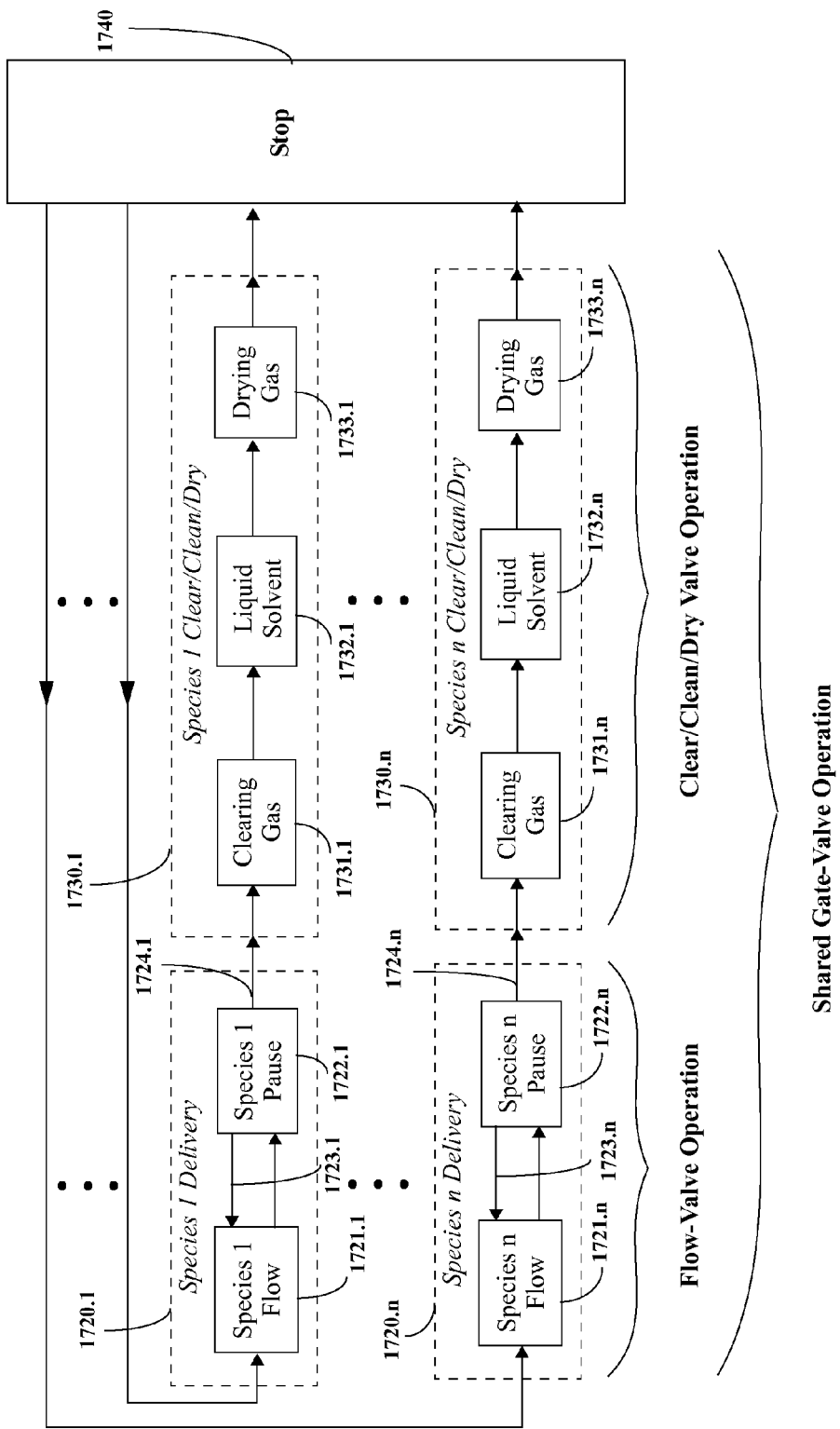

Applying the remarks and observations above, an exemplary generalized operating model, depicted in FIG. 17*d*, is now provided. This model supports an arbitrary number (n) of species. After flow of selected species is initiated 1721.1-1721.*n*, operation can then be directed to a pause state 1722.1-1722.*n* whose duration may be as short or as long as desired or required, or (not shown here) skipped altogether. In some embodiments, a pause state may not be implemented. From the pause state associated with a particular species, operation may either return to flow of the same species 1723.1-1723.*n*, or be directed to the associated (species-specific) instance 1724.1-1724.*n* of a Clear/Clean/Dry mode. After this Clear/Clean/Dry phase is complete, the operation will stop until another delivery phase 1720.1-1720.*n* of any species (same or different) is subsequently initiated.

Flow of the same species may be repeated as many times as required by iterating with an associated pause state (without clearing/cleaning/drying 1730.1-1730.*n*) and/or the stop state 1740 (after clearing/cleaning/drying). Also, from the beginning of species delivery 1720.1-1720.*n* to the end of the associated species clearing/cleaning/drying phase 1730.1-1730.*n*, if any path, valves, or other resources are uniquely assigned to specific species, then those of only the specific species will be used until the stop mode is attained. In some implementations, provisions may be included for skipping the stop state 1740 if another species delivery request is queued up.

Figure 18A:
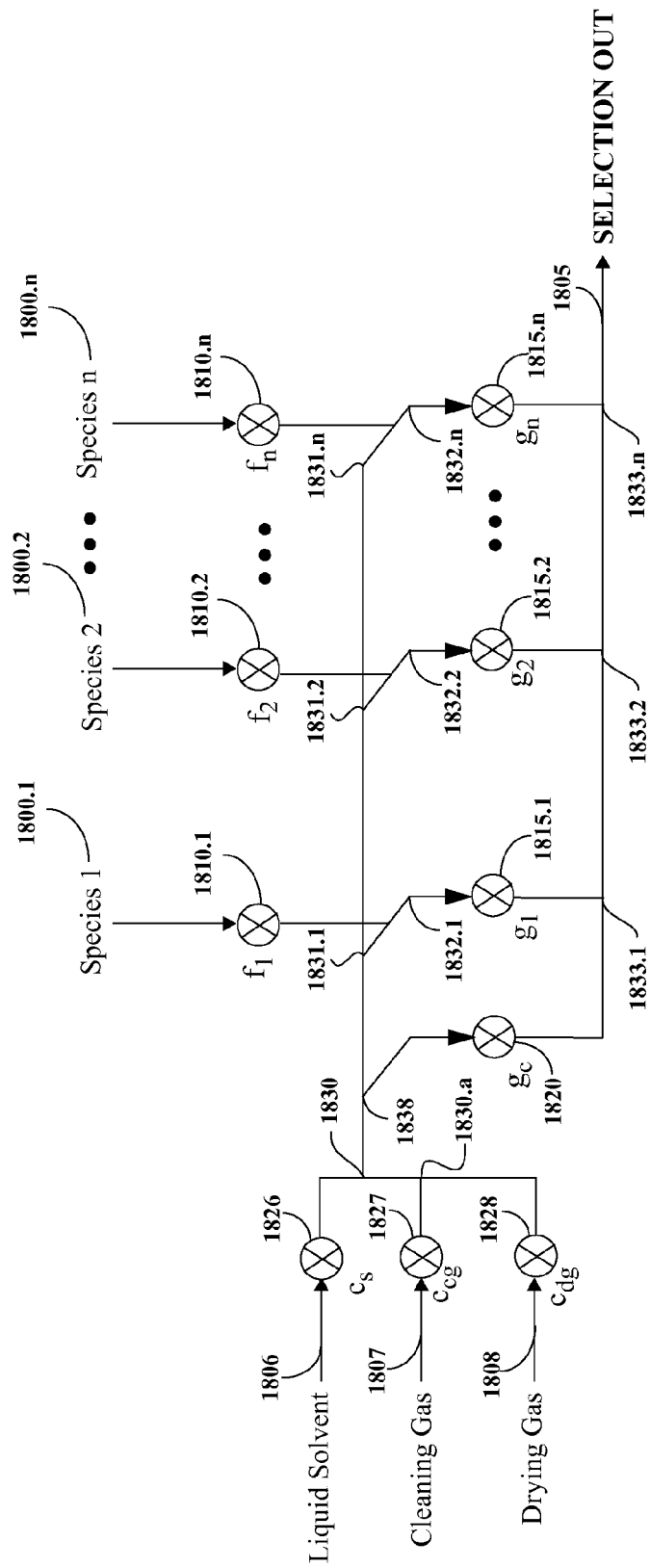
FIGS. 18a-18g depict the exemplary operation of another exemplary valve complex configuration employing on-off valves and providing a single outflow path.

A Second Exemplary Binary-Valve Multi-Port Selection Valve Complex and its Operation FIG. 18*a* illustrates a second exemplary valve complex structure providing n distinct species inflow choices 1800.1-1800.*n* that may be directed to one output outflow 1805, and which also includes in situ clearing, cleaning, and drying provisions. As shown in FIG. 18*a*, this exemplary implementation is composed of n pairs of valves 1810.1-1810.*n* and 1815.1-1815.*n* dedicated for each of n species and four additional valves 1826, 1827, 1828, and 1820 that perform clearing, cleaning, and drying procedures. As a result of its alternate structure, clearing gas, liquid solvents, and drying gas can be routed in three or more different ways through the valve complex as will be described in FIGS. 18c-18g. This will be seen to be advantageous for limiting and cleaning up of contamination. Further, this exemplary implementation includes exemplary provisions for handling a drying gas differing from the provisions employed for handling clearing gas.

Figure 18B:
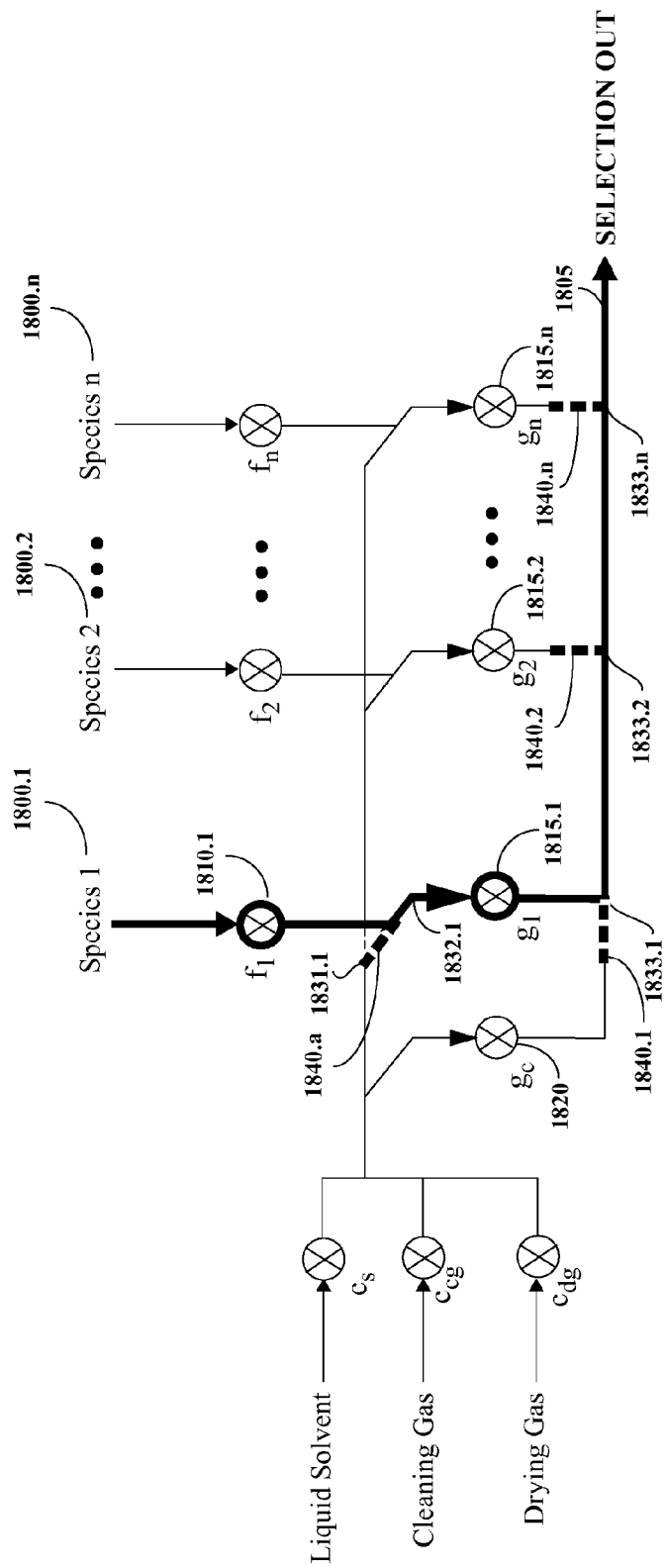

FIG. 18b illustrates the operation for the delivery of Species 1 from its source 1800.1 to the selection outlet port 1805. Note that this exemplary configuration requires the Species 1 flow valve 1810.1 and the Species 1 gate valve 1815.1 to be open for Species 1 to flow.

FIG. 18b shows the resulting flow highlighted with the solid bold line and bold valve outline. The operations for the cases of the other n−1 possible species are similar. While the largest portion of Species 1 travels to the outlet 1805, some degree of contamination will typically occur in the following n+1 different regions:

Region 1840.*a* between joint 1831.1 and joint 1832.1;
Region 1840.1 between joint 1833.1 and clean gate valve 1820;
Region 1840.2 between joint 1833.2 and Species 2 gate valve 1815.2;
. . .
Region 1840.*n* between joint 1833.*n* and Species n gate valve 1815.*n*.

The relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures. Similar contamination exposures, contamination limiting arrangements, and contamination clearing and cleaning strategies apply in the cases of the other n−1 possible species.

Figure 18C:
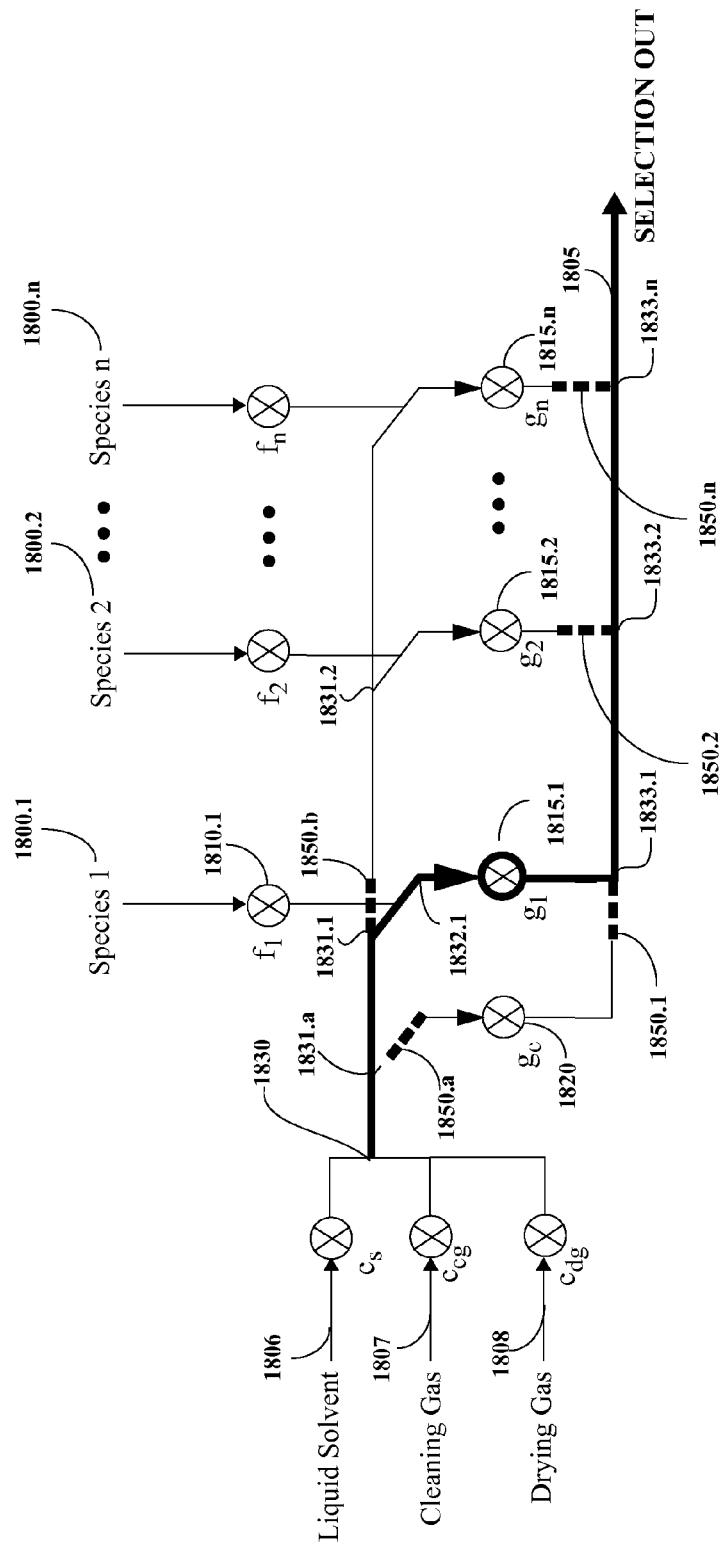

FIG. 18c illustrates the route shared by clearing/cleaning/drying material flows and procedures for the flow channel associated with Species 1. Clearing gas, liquid solvent, and/or drying gas will travel through the juncture 1830 towards the selection outlet 1805, past the flow path for the specific species (here, Species 1 1800.1) towards the selection outlet 1805. The resulting flow is highlighted in the figure via the solid bold line and bold valve outline. This clearing/cleaning/drying operation may be used to clear, clean, and dry the flow path of FIG. 18b. However, this operation will likely cause at least some degree of contamination in the following n+2 regions:

Region 1850.*a* between joint 1831.*a* and the clean gate valve 1820;
Region 1850.*b* between joints 1831.1 and joint 1831.2;
Region 1850.1 between joint 1833.1 and the clean gate valve 1820;
Region 1850.2 between joint 1833.2 and the Species 2 gate valve 1815.2;
. . .
Region 1850.*n* between joint 1833.*n* and the Species n gate valve 1815.*n*.

As with the earlier potential contamination situations described above, the relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures.

Similar contamination exposures, contamination limiting arrangements, and contamination clearing and cleaning strategies apply in the cases of the other n−1 possible species.

Figure 18D:
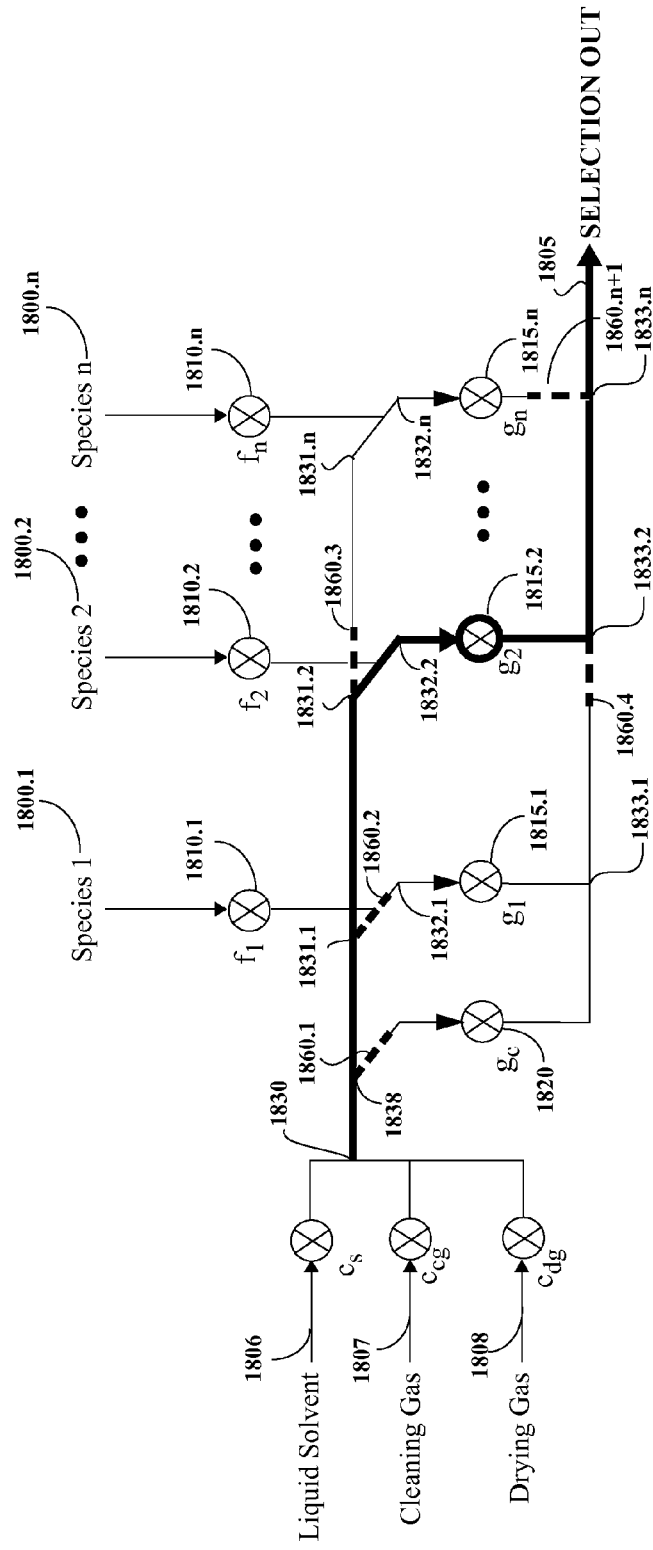

Following on with additional clearing/cleaning/drying operations, FIG. 18d illustrates the route shared by clearing/cleaning/drying material flows and procedures for the flow channel associated with Species 2. This flow is highlighted in the figure via the solid bolded line and bolded valve outline. This clearing/cleaning/drying operation may also be used here to clear, clean, and dry region 1850.*b*. However, this operation will likely cause at least some degree of contamination in the following n+2 regions:

Region 1860.1 between joint 1838 and the clean gate valve 1820;
Region 1860.2 between joint 1831.1 and the Species 1 gate valve 1815.1;
Region 1860.3 between joint 1831.2 and joint 1831.*n;*
Region 1860.4 between joint 1833.2 and joint 1833.1;
. . .
Region 1860.*n*+1 between joint 1833.*n* and the Species n gate valve 1815.*n*.

The relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures. Similar contamination exposures, contamination limiting arrangements, and contamination clearing and cleaning strategies apply in the cases of the other n−1 possible species.

Figure 18E:
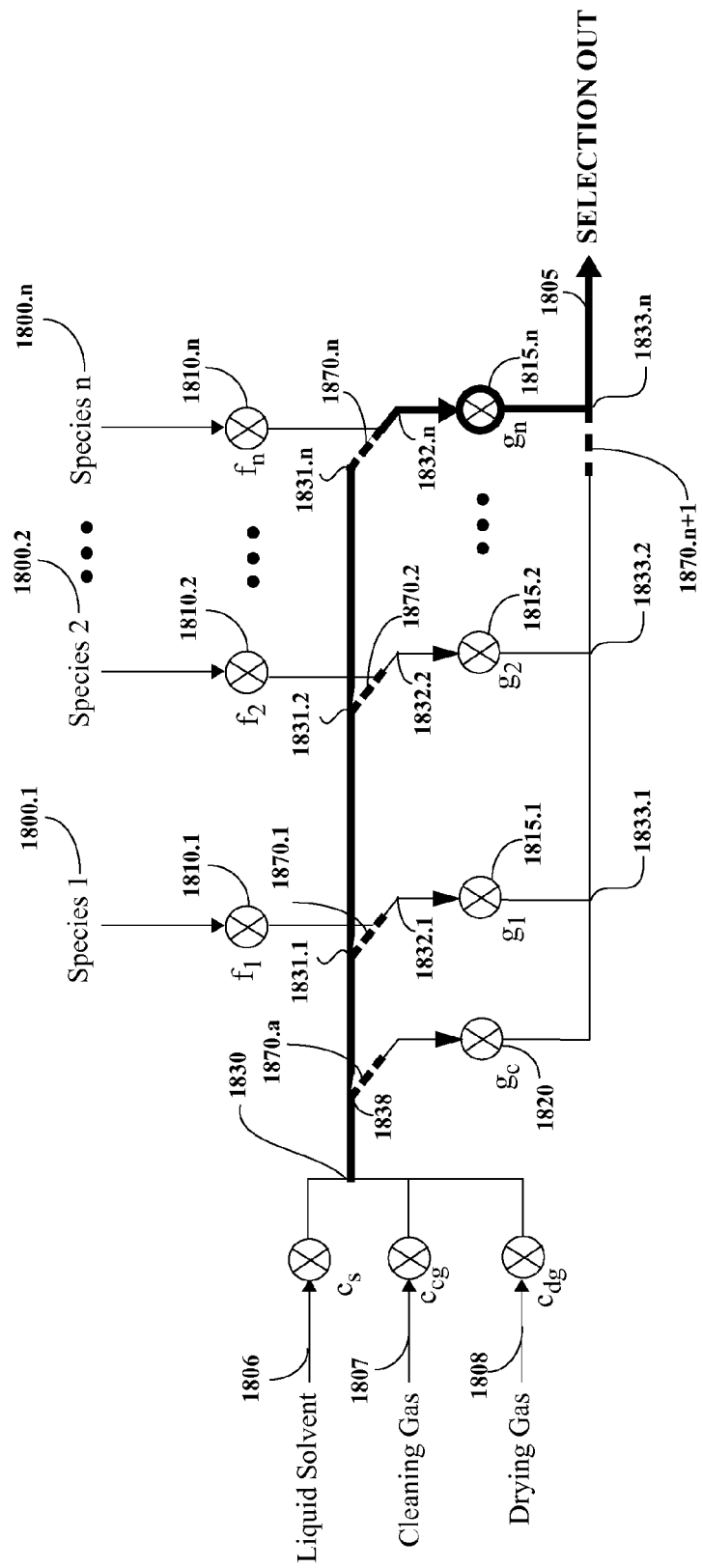

Similarly, FIG. 18e illustrates (via the solid bold line and bold valve outline) the route shared by clearing/cleaning/drying material flows and procedures for the flow channel associated with Species n. This flow is highlighted in the figure via the solid bold line and bold valve outline. This operation may also be used here to clear, clean, and dry region 1860.3. However, this operation will likely cause at least some degree of contamination in the following n+2 regions:

Region 1870.*a* between joint 1838 and the clean gate valve 1820;
Region 1870.1 between joint 1831.1 and the Species 1 gate valve 1815.1;
Region 1870.2 between joint 1831.2 and the Species 2 gate valve 1815.2;
. . .
Region 1870.*n* between joint 1831.*n* and the Species n gate valve 1815.*n;*
Region 1870.*n*+1 between joint 1833.*n* and joint 1833.2.

The relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures. Similar contamination exposures, contamination limiting arrangements, and contamination clearing and cleaning strategies apply in the cases of the other n−1 possible species.

Figure 18F:
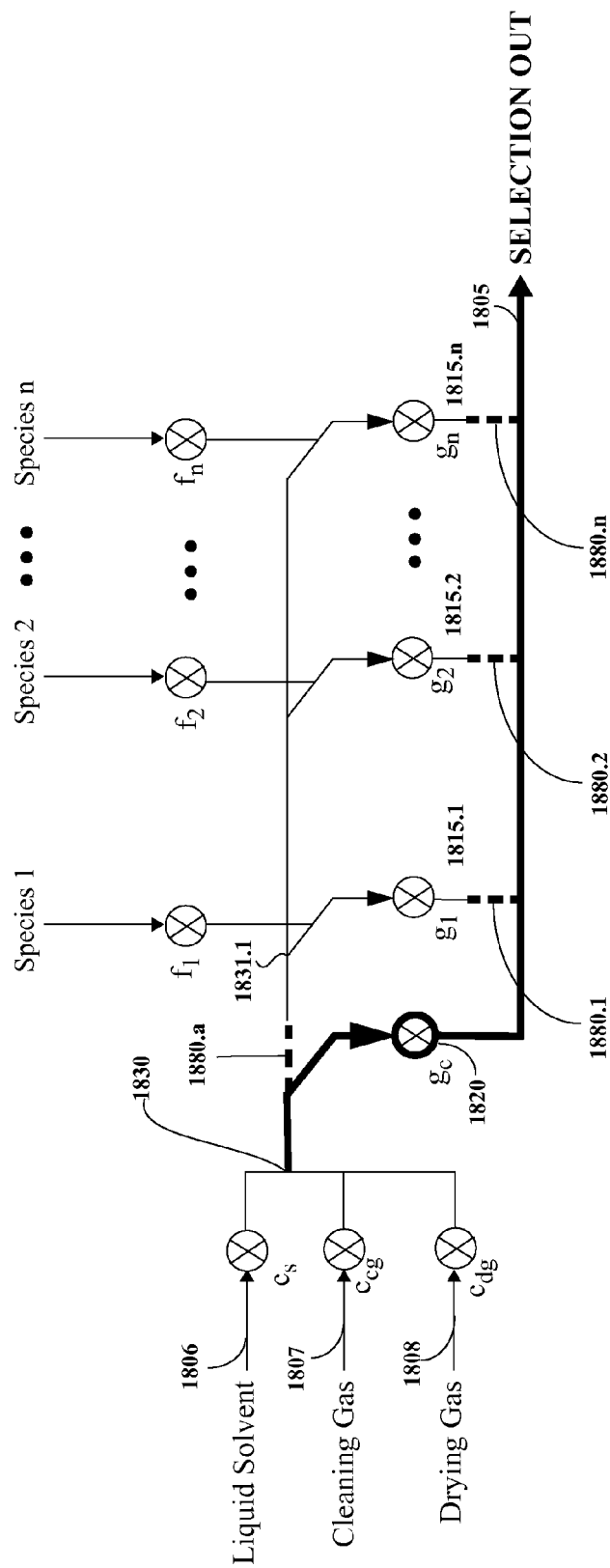

In contrast to each of the sequences above, FIG. 18f shows the usage of a second alternative clearing/cleaning/drying path involving cleaning gate valve 1820. This flow is highlighted in the figure via the solid bold line and bold valve outline. Note that while the solvent or selected gas travels towards the selection outlet 1805, contamination potential will occur in the following n+1 regions:

Region 1880.*a* between joint 1838 and joint 1831.1;
Region 1880.1 between joint 1833.1 and the Species 1 gate valve 1815.1;

Region 1880.2 between joint 1833.2 and the Species 2 gate valve 1815.2;

...

Region 1880.*n* between joint 1833.*n* and the Species n gate valve 1815.*n*.

The relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures. Similar contamination exposures, contamination limiting arrangements, and contamination clearing and cleaning strategies apply in the cases of the other n−1 possible species.

In some implementations, it may be advantageous to interleave the operation depicted in FIG. 18*f* within the sequence of species flow procedures described earlier in association with FIGS. 18*b*-18*e* so as to clear, clean, and dry subsequent new contaminations as well as original channel backflow contaminations. If there is sufficient clear, clean, and dry material flow pressure, it may be advantageous in some implementations to perform a plurality or indeed all of these channel clearing/cleaning/drying operations simultaneously.

Figure 18G:
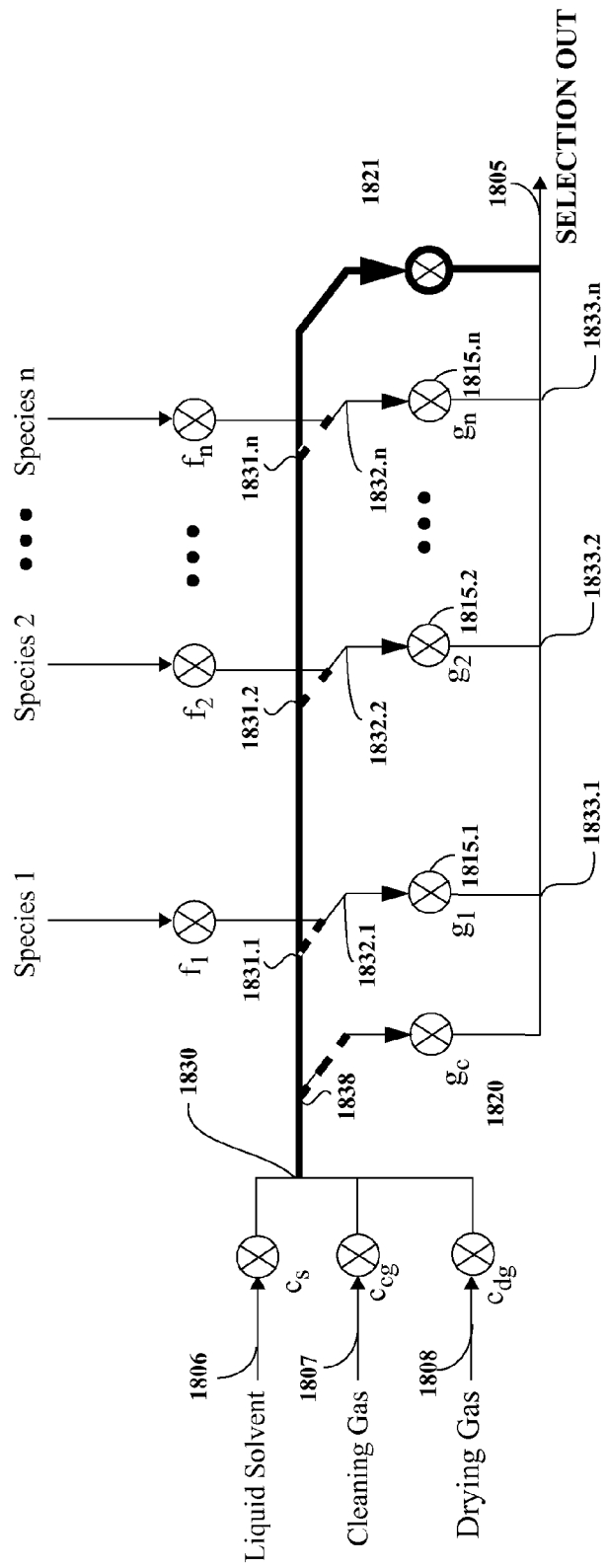

In yet another consideration, FIG. 18*g* illustrates a modification of the arrangement described in association with FIGS. 18*a*-18*f* so as to include an additional valve 1821 dedicated to clearing, cleaning, and drying the final segment near the end of the selection outlet 1805. This path passes through the region where the flows from flow valves 1810.1-1810.*n* for all the species meet but bypasses the region where the flows from gate valves 1815.1-1815.*n* for all the species meet. This alternate path has the potential for contamination in the following n+1 regions:

Region 1890.*a* between joint 1838 and the clean gate valve 1820;

Region 1890.1 between joint 1831.1 and joint 1832.1;

Region 1890.2 between joint 1831.2 and joint 1832.2;

...

Region 1890.*n* between joint 1831.*n* and joint 1832.*n*.

The relative degree and overall volume of contamination in one or more of these areas may vary considerably depending upon details of the implementation, layout, preventative aspects, etc. Resultant contamination in one or more of these regions may be cleared and cleaned by various additional structures and/or subsequent procedures. Similar contamination exposures, contamination limiting arrangements, and contamination clearing and cleaning strategies apply in the cases of the other n−1 possible species. Usage of this path may be interleaved with the ones described above in association with FIGS. 18*b*-18*f* so as to clear, clean, and dry subsequent new contaminations as well as original channel backflow contaminations. If there is sufficient clear, clean, and dry material flow pressure, it may be advantageous in some implementations to perform a plurality or indeed all of these channel clearing/cleaning/drying operations simultaneously.

An Exemplary Binary-Valve Multi-Port Vector Valve Complex and its Operation

Figure 19:
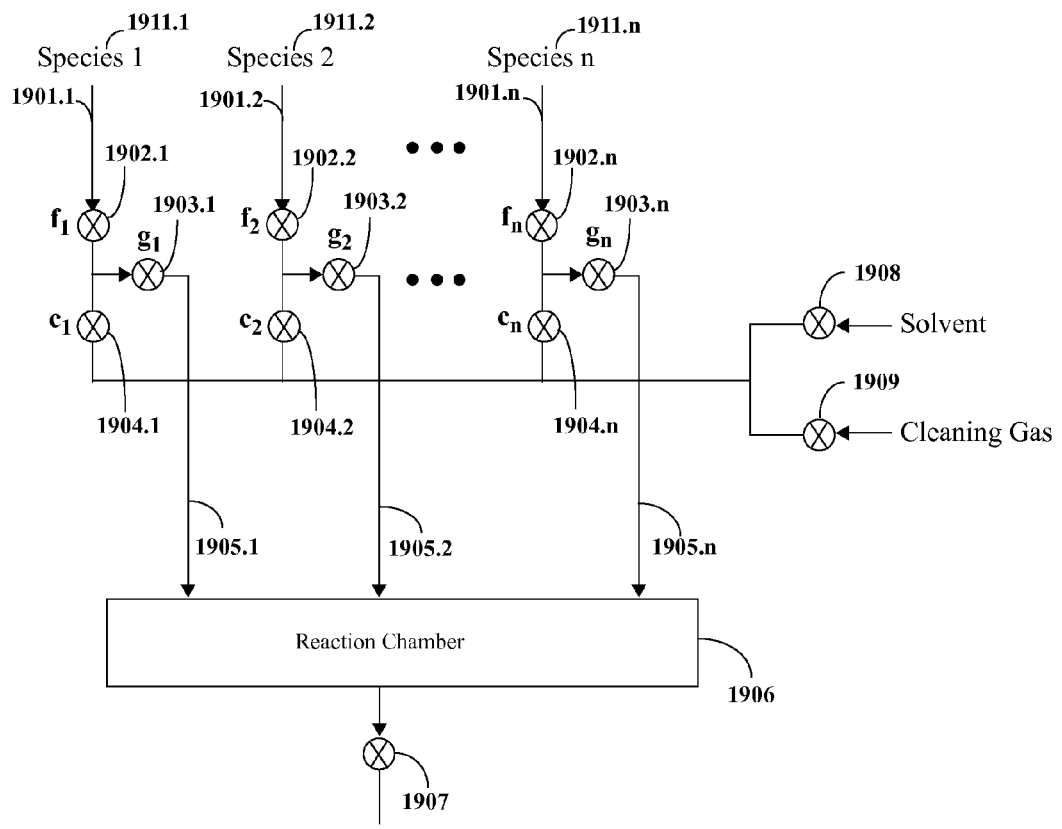
FIG. 19 illustrates an exemplary vector structure comprising n species inputs for n distinct species each directed to a separate port of a common reaction chamber.

The valve arrangements described thus far in association with FIGS. 18*a*-18*g* have a single outflow port which directs fluids and/or gases to subsequent stages. In many situations it is permissible, useful, or even advantageous to have a dedicated port output for each species. FIG. 19 illustrates an exemplary vector structure comprising n species inputs 1901.1-1901.*n* for n distinct species 1911.1-1911.*n* and n species outputs 1905.1-1905.*n*. Unlike the single-output valve complexes described in association with FIGS. 18*a*-18*g*, this arrangement features n clearing/cleaning valves 1904.1-1904.*n* each dedicated to a corresponding one of the species 1911.1-1911.*n*. Such a vector valve could be used, for example, in conjunction with a multiple-inflow reaction chamber 1906.

In order for a selected species from 1911.1-1911.*n* to be delivered, the corresponding flow valve from 1902.1-1902.*n* and corresponding gate valve from 1903.1-1903.*n* associated with the selected species are opened. For example, in a Species 1 delivery mode, Species 1 1911.1 will travel through the Species 1 flow valve 1902.1 and the Species 1 gate valve 1903.1 to the associated output port 1905.1 and thus delivered directly to the reaction chamber 1906. Measured amounts of selected species can be sequentially or simultaneously delivered to reaction chamber 1906 where they are held by means of a closed outlet valve 1907. This would typically require pressure equalization ("venting") provisions to be provided by other means, or by the valve complex itself. When the reaction is complete, the outlet valve 1907 is opened and the reaction chamber 1906 is emptied. After the product is delivered, the outlet valve 1907 may be again closed and opened to allow for clearing, cleaning, and drying operations.

SPDT Valves

The selection valve arrangement depicted in FIGS. 18*a*-18*f* and FIG. 19 all typically realized using simple on-off valve elements, often referred to in the field by the potentially confusing terminology of "two-way" valves. A more accurately descriptive name for the purposes of this discussion is the term "two-port valve elements." These simple two-port valve elements are often the easiest and least-costly valve elements to fabricate. In some situations, however, it can be cost effective enough to consider the use of more complex valve elements. Of these the next level of complexity are those commonly referred to as "three-port valves." A variety of three-port valves are known, including types with internally rotating flow-routing members that permit all possible interconnections of the three ports. In the discussions to follow, a simple version with flow routing analogous to an electrical single-pole double-throw (SPDT) switch, or more precisely, a SPDT relay, is utilized. Such "SPDT" valve elements comprise a shared "common" port that in a first mode of operation is connected to a first of the two other ports and in a second mode of operation is connected to a second of the two other ports. Flow between the common port and one of the two other ports is possible at all times.

In SPDT valves, flow is directed among the ports responsive to signals or energy provided to the valve. In some implementations, pulses are used to change which port the flow is directed to from an existing state to the opposite state. In other valve implementations, one port (designated as "normally open") is configured to normally be connected to the common port with the other port (designated "normally closed") is shut closed, and the flow conditions of the normally open and normally closed ports are reversed when energy is applied. Such valves may be realized by rocking or rotating flow-routing members, or by other means.

Reorganization of a Previous Valve Complex Using SPDT Valves

Figure 20:
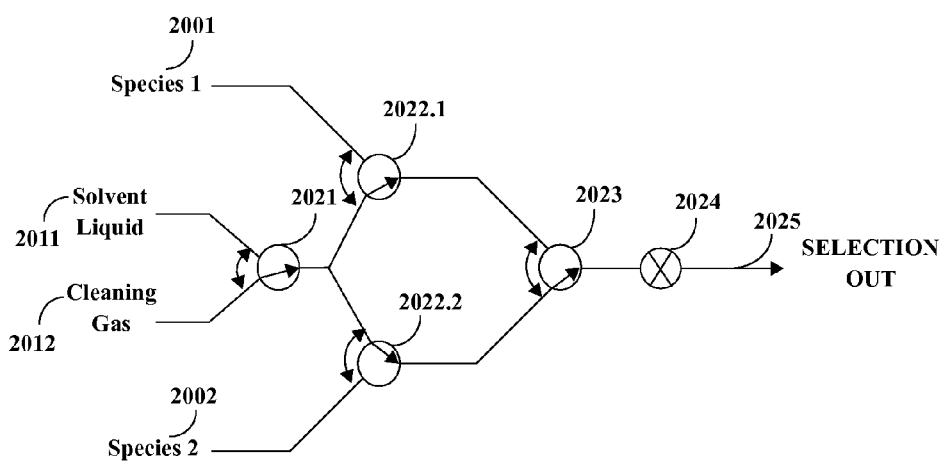

FIG. 20 depicts an alternate implementation of the general arrangement of the valve complex depicted in FIG. 16*a* but here using SPDT valve elements. As in FIG. 16*a*, two species 2001, 2002 are externally provided, as are solvent liquid 2011 and cleaning gas 2012, and a series of valves select among these and produce an outgoing flow 2025. In this realization, an SPDT valve element 2021 selects between solvent liquid 2011 and cleaning gas 2012, routing the result to both of two additional SPDT valve elements 2022.1 and 2022.2. These each respectively select between the outflow of solvent/clearing valve element 2021 and Species 1 2001 and 2 2002. The outflows of each of 2022.1 and 2022.2 are then directed to another SPDT valve element 2023 that selects between these resulting potential flows, and directs its selection to an on/off gate valve 2024 at the final outflow exit path 2025. Note that the arrangement naturally provides for clearing and cleaning. The arrangement is arguably simpler than that of FIG. 16a from a routing and valve-count view, or comparable to that of FIG. 16a when the added cost and complexity of the four SPDT valves are taken into consideration. However, there can be additional considerations of ambient species, solvent, and gas occupation in the interlinkages among the four SPDT valves. This results since, with no species, solvent, or gas gating valves in the flow, the interlinkages among the four SPDT valves will be occupied with remnants of at least one of the species, solvent or gas at full source pressure at all times. The advantage of using the SPDT valves rather than the simpler on/off valves for this arrangement is thus not universally clear.

Chain Structures SPDT Valve Complexes for Selection and Distribution

There are, however, arrangements where SPDT valve elements have a natural advantage. One such arrangement is a chain structure, such as that depicted in FIG. 21a. The chain structure is of particular interest since it can be used as the central routing element of either a selection valve complex or a distribution valve complex. The example shown in FIG. 21a comprises four SPDT valves 2103.1-2103.4, each directed to the port on the left, resulting in a flow path between 2101 and 2105. The flow along this path can be in either direction, and can be interrupted and redirected by reconfiguring at least one of the four SPDT valves 2103.1-2103.4 to its alternate position. For example, directing SPDT valve 2103.1 to its right-most port interrupts the flow path between 2101 and 2105, and redirects the flow path to one between 2101 and 2104.1. Again, flow through this new flow path may be in either direction. Similarly, reconfiguring SPDT valve 2103.2 to open to the right creates a path from 2101 to 2104.2 as long as the previously mentioned SPDT valve 2103.1 is directed to its left-most port. Similarly, the flow path between 2101 and 2105 can be interrupted and redirected to the flow path between 2101 and 2104.3 as long as both SPDT valves 2103.1 and 2103.2 are directed to their respective left-most ports. This general pattern continues for additional SPDT valves and associated alternative paths (such as SPDT valve 2103.4 and path 2104.4, respectively) introduced in the chain. This approach can be readily extended to smaller or larger numbers of two-way valves. Multiple instances of such chains 2100 may be nested, connecting inputs to outputs, to form tree topologies.

Figure 21A:
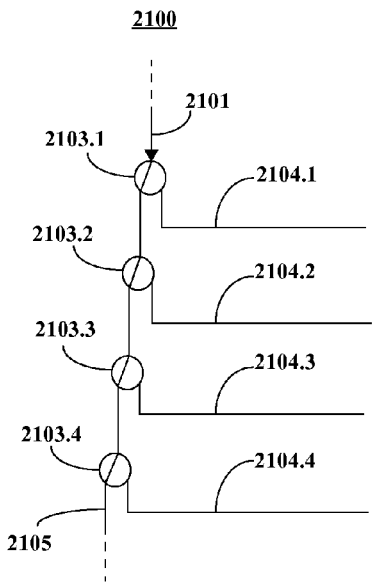
FIG. 21a-21b depict various valve complexes comprising a cascade of SPDT valves.
Figure 21B:
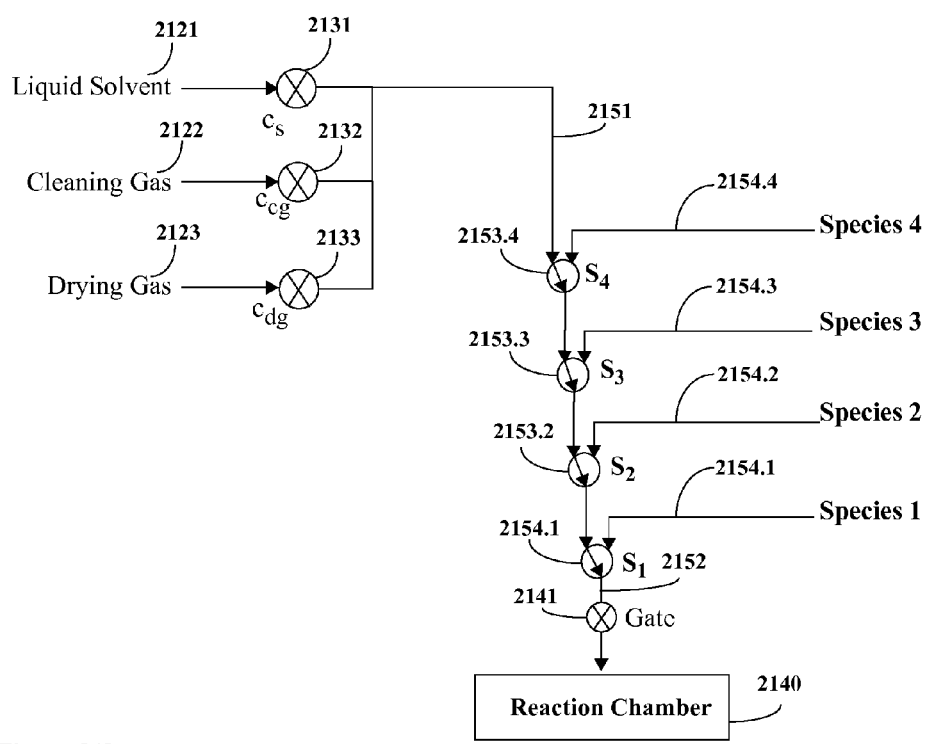

FIG. 21b shows the chain of SPDT valves depicted in FIG. 21a applied to an exemplary embodiment of a multiport selection valve with clearing and cleaning provisions. Here the chain of FIG. 21a is depicted upside-down, adapting flow path 2101 as an outflow path 2152 directed to a gate valve 2141 preceding a reaction chamber 2140. The application of the chain of FIG. 21a further involves adapting flow path 2105 to serve as a common clearing/cleaning flow path 2151 and adapting flow paths 2104.1-2104.4 as inlets 2154.1-2154.4 for incoming species. In this configuration, SPDT valve $S_1$ 2154.1 selects between the Species 1 inflow 2154.1 (right-most port) or other options (left-most port) which may comprise any of Species 2-4, liquid solvent, clearing gas or drying gas, the latter choices determined by the modes of one or more of SPDT valves $S_2$ 2153.2, $S_3$ 2153.3, $S_4$ 2153.4 and on/off valves $C_s$ 2131, $C_{cg}$ 2132, and $C_{dg}$ 2133. For example, if SPDT valves $S_1$ 2153.1 and $S_2$ 2153.2 are directed to their left-most ports while SPDT valve $S_3$ 2153.3 is directed to its right most port, then Species 3 inflow 2154.3 can directed into the reaction chamber 2140 when on-off gate valve 2141 is opened. As another example, when all of the SPDT $S_1$-$S_4$ valves 2153.1-2153.4 are directed to their left-most port and gate valve 2141 is opened, then any of on-off valves $C_s$ 2131, $C_{cg}$ 2132, and $C_{dg}$ 2133 may be individually opened so as to direct, respectively, liquid solvent 2121, clearing gas 2122 or drying gas 2123 to the reaction chamber 2140. It will be clear to one skilled in the art that reaction chamber 2140 and associated gate valve 2141 are only exemplary destinations and that other configurations could be employed here or in other parts of the exemplary multi-port selection valve configuration of FIG. 21b. In a similar fashion, the on-off valve configuration 2131-2133 may itself be replaced with a chain of three SPDT valves.

Figure 21C:
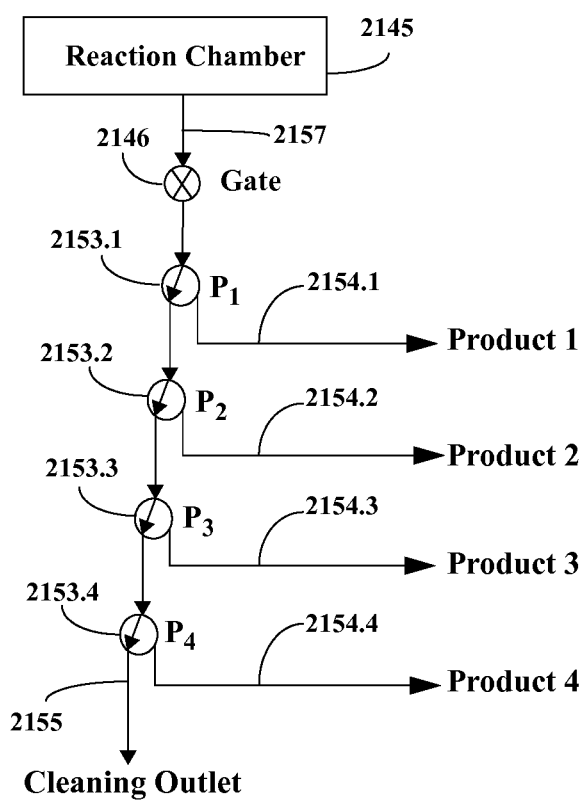
FIGS. 21c and 22a illustrate exemplary multi-port distribution valve complexes comprising a cascade of SPDT valves.

The chain of SPDT valves like that depicted in FIG. 21a may also be incorporated into embodiments of multi-port distribution valve complexes with in-situ clearing, cleaning, and drying provisions, as illustrated in the exemplary arrangement of FIG. 21c. In contrast to FIG. 21b (where species and clearing/cleaning/drying agents outflow to the reaction chamber 2140), this valve complex embodiment accepts as its inflow the outflow from a reaction chamber 2145, and the plurality of SPDT valves 2153.1-2153.4 subsequently direct the flow to any of the product outlets 2154.1-2154.4 or the cleaning outlet.

More specifically in the adaptation of FIG. 21a into the embodiment depicted in FIG. 21c, a reaction chamber 2145 and an associated gate valve 2146 are used as a source feeding into a flow path 2157 equivalent to the flow path 2101 of FIG. 21a, while a flow path equivalent to the flow path 2105 of FIG. 21a is employed as a common cleaning outlet 2155. The flow paths 2104.1-2104.4 of FIG. 21a are employed as outflow paths 2154.1-2154.4, respectively, for Product 1-Product 4.

As an example of operation, a first reaction result may be directed to the Product 1 outflow path 2154.1 when on-off gate valve 2146 is opened and $P_1$ SPDT valve 2153.1 is directed towards its right-most port. After the transfer of this reaction product, the gate valve 2146 may then close and the $P_1$ SPDT valve 2153.1 is then directed towards its left-most port. Clearing and cleaning of the reaction chamber 2145 may occur with the gate valve open and closed in various sequences. During this interval clearing gas and liquid solvent can traverse the path through all SPDT valves 2153.1-2153.4 to the common cleaning outlet 2155. Later, drying gas may be applied to the reaction chamber 2145 to dry residual solvent remaining in the path traversing through the SPDT valves 2153.1-2153.4 to the common cleaning port 2155. Then the reaction chamber 2145 may be used to create a new reaction product that can be directed to Product 2 out flow path 2154.2 with $P_1$ SPDT valve 2153.1 directed to its left-most port and $P_2$ SPDT valve 2153.2 directed to is right-most port. Additional clearing, cleaning, and product outflow cycles may proceed in a similar fashion to those just described: when all of the valves 2153.1-2153.4 are in their inactivated state, the outflow from the reaction chamber 2145 will flow through all the valves and be directed to the cleaning outlet 2155.

Figure 22A:
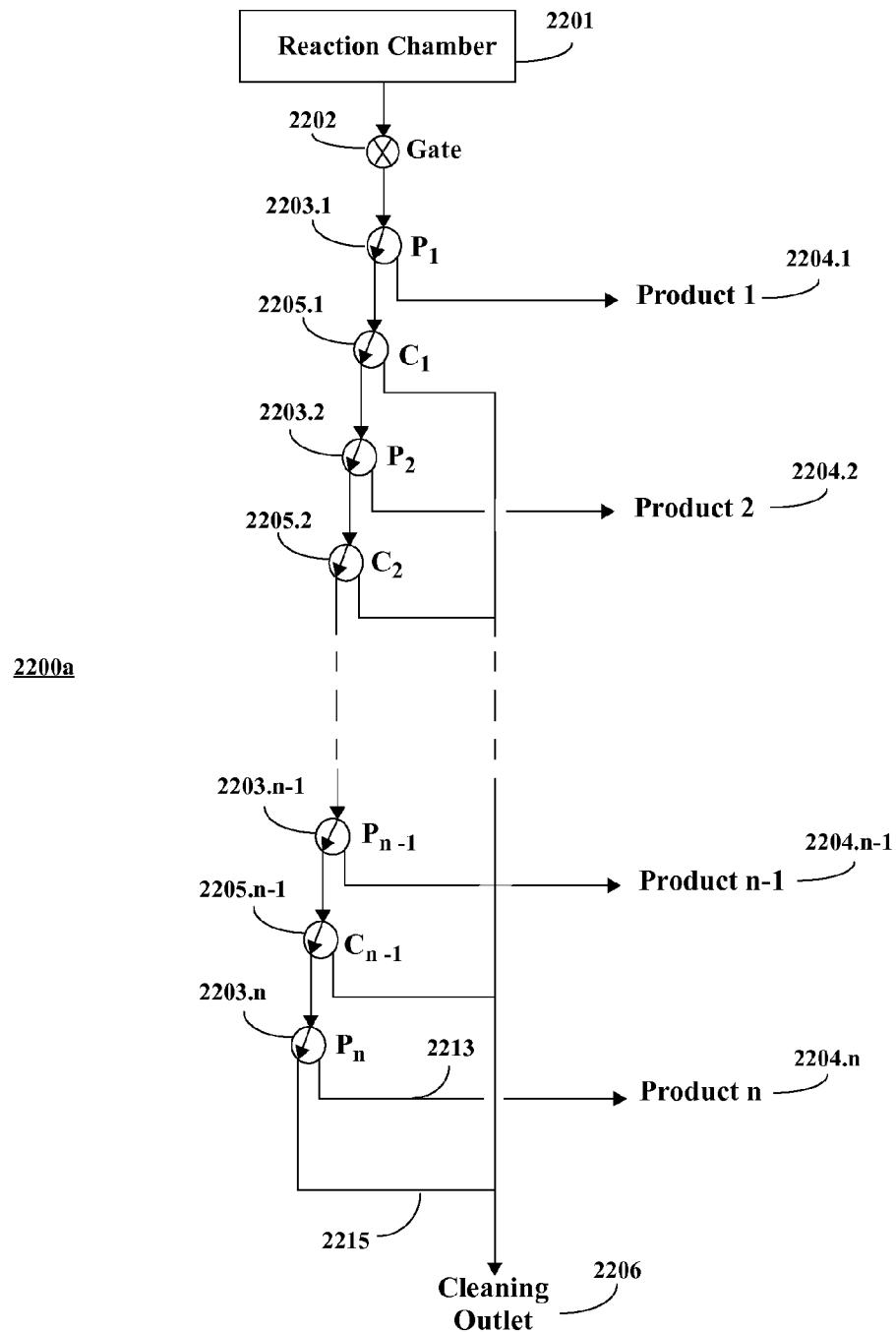

FIG. 22a illustrates a second exemplary multi-port distribution valve complex employing SPDT valves. In this example, a double-length chain of SPDT valves is used to deliver the outflow of a reaction chamber 2201 to an arbitrary number (n) of product outlets 2204.1-2204.n and a cleaning outlet 2206. The additional valves permit the system to clean some regions more often than others and can be used for more sophisticated subsequent solvent recovery and product recovery operations. As with the example depicted in FIG. 21c, an on-off gate valve 2202 is placed after the reaction chamber 2201 that allows the outflow from the reaction chamber 2201 whenever the valve structure 2200a is engaged. As with the example depicted in FIG. 21c, the remainder of the valves are SPDT valves, with each valve utilized to alternately conduct the flow to the corresponding product or cleaning outlet when the valve is so directed, and to the next valve in the series otherwise.

For each product, a pair of SPDT valves comprising a flow valve and a cleaning valve is followed by another similar pair of valves dedicated to handling the next product. Thus the cleaning valve for each product is placed right after the corresponding product flow valve to clean and clear the flow path before a different product flows through the path. Each product output valve 2203.1-2203.n directs the flow to the corresponding product outlet 2204.1-2204.n when in one mode, otherwise letting the flow pass through to the next stage. This is also the case for the valves delegated for cleaning 2205.1-2205.n−1. One aspect of this alternating structure is that one fewer cleaning valve is needed; more specifically, the nth cleaning valve is not needed as the last valve 2203.n directs the outflow to two different paths 2213 or 2215.

When the gate valve 2202 and first SPDT valve 2203.1 is exclusively activated, the outflow will be directed to the Product 1 outlet 2204.1. When the next valve 2205.1 is oriented to the left and the gate valve 2202 is opened, the flow path will be directed to the cleaning outlet 2206. The sequence repeatedly extends up to and includes the delivery of Product n−1 and subsequent clearing/cleaning/drying. For Product n, the final SPDT valve 2203.n in the chain 2203.n will direct the flow to either along path 2213 to the nth Product outlet 2204.n, or along path 2215, in which case the flow is directed to the cleaning outlet 2206.

Figure 22B:
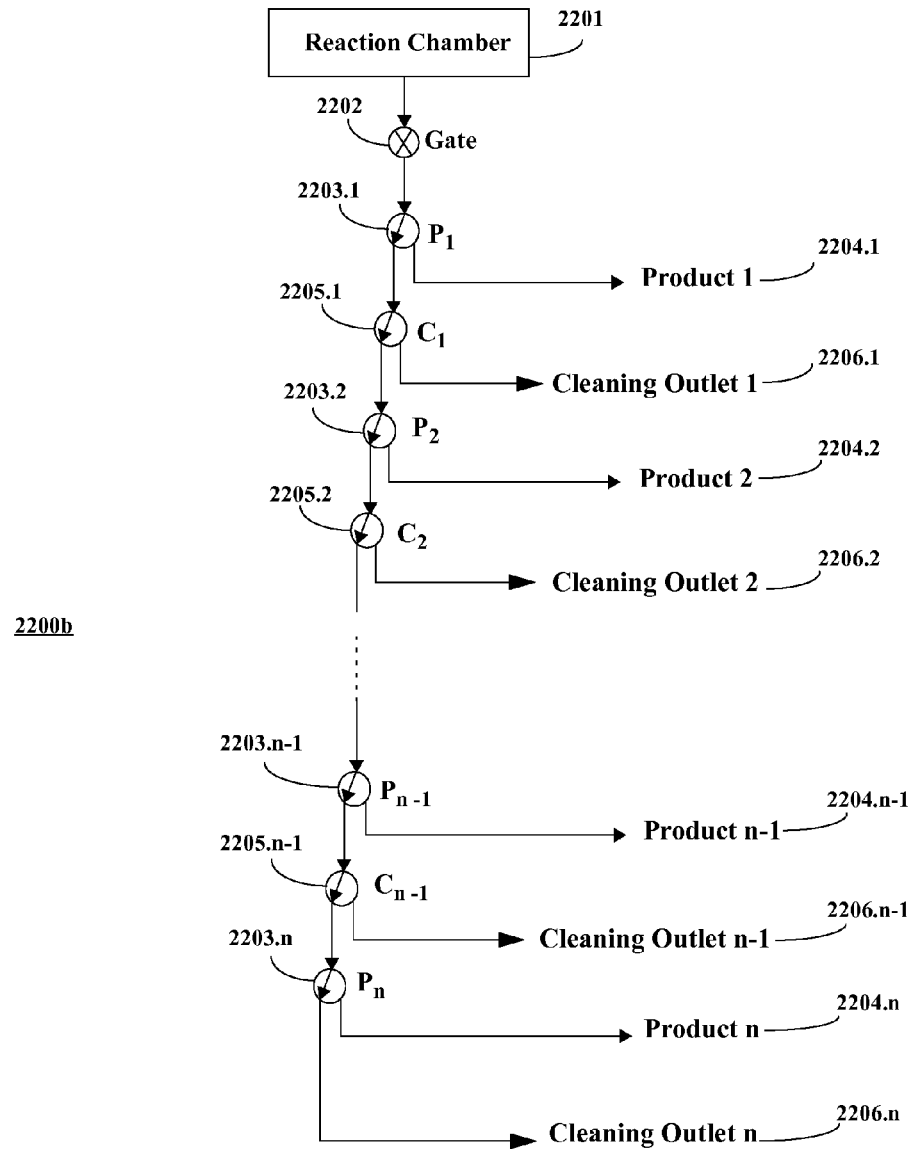

FIG. 22b illustrates a modification of the valve structure 2200a described above in conjunction with FIG. 22a. Instead of the common cleaning outlet 2206 of FIG. 22a, the modified embodiment depicted in FIG. 22b features separate cleaning outlets 2206.1-2206.n. These separate outlets 2206.1-2206.n enable recycling of the mixture of product and clearing/cleaning/drying materials. Separation methods such as filtering or layering may be then applied to these mixtures so as to recover one or more of the constituents that would otherwise be disposed.

Chemical Transport Elements and Their Operation

Returning briefly to FIG. 8b, a number of exemplary operational entities are identified as follows:
Fluid and/or gas reservoirs 825,
Passive interconnection conduits 826,
Controllable valves 827,
Reaction chambers 828,
Heating and cooling elements 829,
Sensors 830,
Pumps 831,
Other (evaporators, condensers, mixers, agitators, bubblers, filters, flow constrictors, chromatography columns, electrophoresis elements, etc.).

Figure 23A:
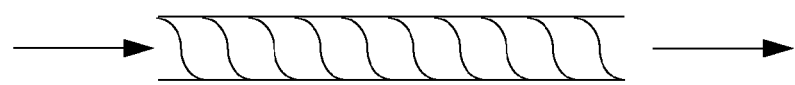
FIGS. 23a-23c depict various types of surface texturing, rib, or fin elements attached to or fabricated into the form of the passive interconnection pathway element conduit walls.
Figure 23B:
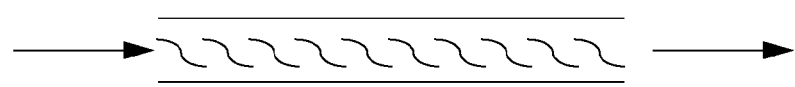
Figure 23C:
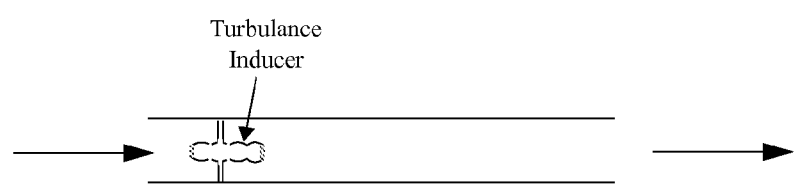

The passive interconnection conduits 826 provide physical transport of fluids, gases, and perhaps other types of chemical material (slurries, powders, etc.) among the other elements listed above as well as yet other entities (such as external connection ports). These passive interconnection conduits 826 permit flows driven by pressure, capillary action (which predominates in small systems), and gravity (which predominates in larger systems). The various valve arrangements described earlier provide flows of chemical species, chemical products, and clearing/cleaning/drying materials. In some situations, the clearing/cleaning/drying processes for other elements attached to passive interconnection conduits 826, and/or the passive interconnection conduits 826 themselves, may benefit from the provision of turbulence-inducing structures along the interiors of the passive interconnection conduits 826. Some examples of such turbulence-inducing structures include:

Various types of continuous-feature surface texturing, rib, or fin elements attached to or fabricated into the form of the passive interconnection pathway element conduit 826 walls, as in the exemplary linear spiraling feature depiction shown in FIG. 23a, Various types of truncated-feature surface texturing, rib or fin elements attached to or fabricated into the form of the passive interconnection conduit 826 walls, as in the exemplary linear spiraling feature depicted in FIG. 23b, Various types of in-line turbulence-inducing elements suspended in the passive interconnection conduit 826, as depicted in FIG. 23c, as well as other types of features familiar to those skilled in the art more which may be subsequently developed for this purpose, such as sophisticated microscale or nanoscale surface texturing patterns imposed on the passive interconnection conduit walls.

In utilizing, selecting, and designing such turbulence-inducing structures, one skilled in the art will typically balance any advantages provided by such structures against the added surface areas and dihedral volumes introduced, which provide areas and volumes where residues can accumulate.

Specialized Interconnection Arrangements

The arrangements depicted in FIG. 14a-FIG. 14d have a quite arbitrary topology. In some situations, it may be advantageous to directly facilitate specific types of interconnection arrangements among specific collections of chemical reaction elements 1413, additional chemical system elements 1421 and associated multi-port selection 1411 and distribution valves 1412. Such specific interconnection arrangements may be motivated by a variety of needs, opportunities, and design considerations, such as:

a. Implementation of a special purpose subsystem;
b. Forced segregation between certain chemical species;
c. Simultaneous (or near-simultaneous) parallelization of analogous or other related processes;
d. (Given sufficiently inexpensive large-scale fabrication or other cost considerations) providing an alternative to clearing, cleaning, and drying by offering a significant or sufficient number of limited-use elements;
e. (Given sufficiently inexpensive large-scale fabrication or other cost considerations) providing an alternative to clearing, cleaning, and drying by offering a significant or sufficient number of single-use elements.

The interconnection topology of such specific interconnection arrangements may cover a wide range of homogenous (chains, rings, arrays, etc.) and inhomogeneous types.

Figure 24:
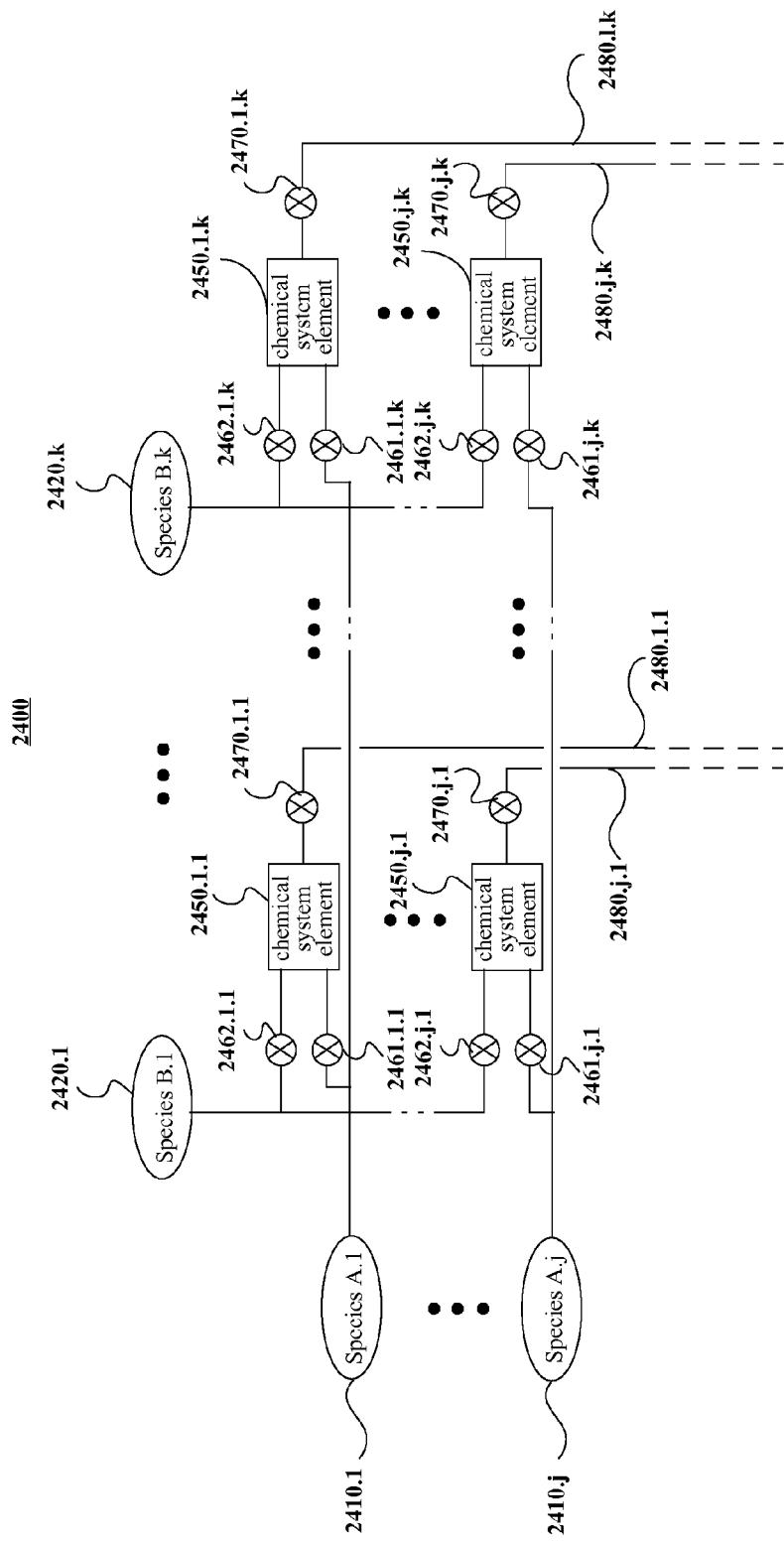
FIG. 24 depicts an example of a two-index array arrangement wherein a plurality of chemical system elements are interconnected to correspond to an matrix of j rows and k columns.

FIG. 24 depicts a simple example of a two-index array 2400 arrangement of particular note wherein a plurality of chemical system elements 2450.1.1-2450.j.k are interconnected so as to correspond to an abstract matrix of j rows and k columns. In this exemplary specialized arrangement, each of the chemical system elements 2450.1.1-2450.j.k is provided with a unique selection of chemical species of two families, one family (here "Species A.1-Aj") 2410.1-2410.j assigned to the "rows" and another family (here "Species B.1-B.k") 2420.1-2420.k assigned to the "columns." Each of the chemical system elements 2450.1.1-2450.j.k is provided with incoming flow valves 2461.1.1-2461.j.k and 2461.1.1-2462.j.k for each of the assigned chemical species from the two families 2410.1-2410.*j* and 2420.1-2420.*k*. For example, chemical system element 2450.1.1 is provided with incoming flow valve 2461.1.1 to control the inflow of Species A.1 2410.1 and incoming flow valve 2462.1.1 to control the inflow of Species B.1 2420.1. Each of the chemical system elements 2450.1.1-2450.*j.k* is provided with its own outgoing gate valve 2470.1.1-2470.*j.k*; for example, chemical system element 2450.1.1 is provided with outgoing gate valve 2470.1.1, in this case thereafter connected to an associated dedicated outflow path 2480.1.1 although other arrangements are obviously possible and apparent to one skilled in the art. As depicted here, none of the chemical system elements 2450.1.1-2450.*j.k* is provided with any means of clearing, cleaning or drying. These could clearly be added. In some implementations of the invention or applications, however, clearing, cleaning or drying provisions may not be necessary nor cost effective (for example should the chemical system elements 2450.1.1-2450.*j.k* be dedicated to specific reaction constituents or dedicated to limited on one-time use).

Control System Attributes

In order for the reconfigurable systems described thus far to be placed into specific configurations, to operate in them, and (in their full potential) to be reconfigured, control systems are typically required. Although there can be hybrid cases and hierarchical constructions (where reconfigurations are made as part of a larger process), the lowest-level control systems may be classified according to which of the following components they comprise:

Configuration Control Systems:
    Configuration management directed to assembling an operational configuration;
    Configuration management control directed to Clearing/Cleaning/Drying;
  Operating Control Systems:
    Process control directed to operating an operational configuration;
    Process control directed to Clearing/Cleaning/Drying.

Figure 25A:
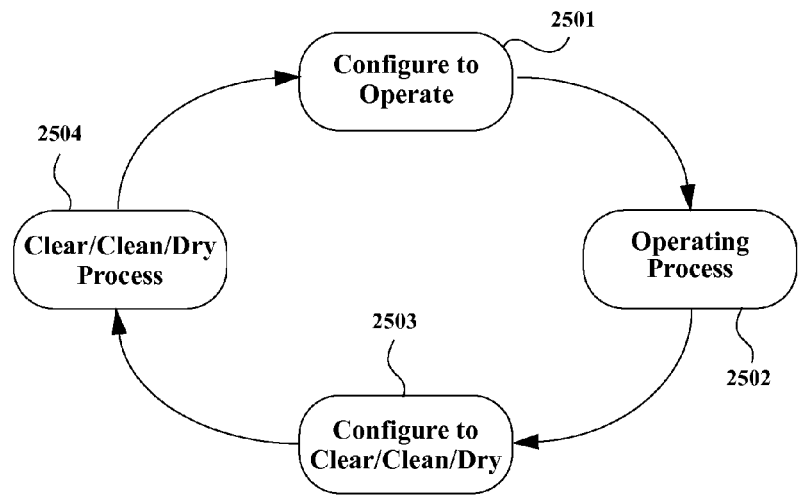
FIGS. 25a-25c depict exemplary state transition diagrams for configuration changes.
Figure 25B:
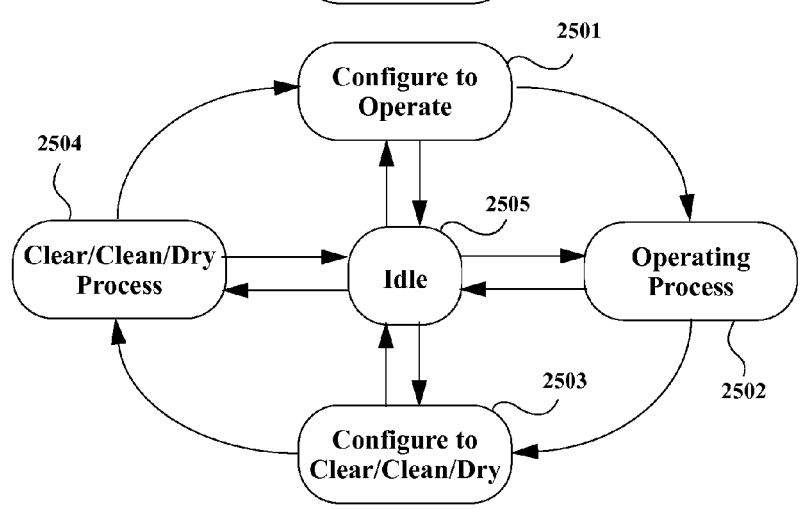
Figure 25C:
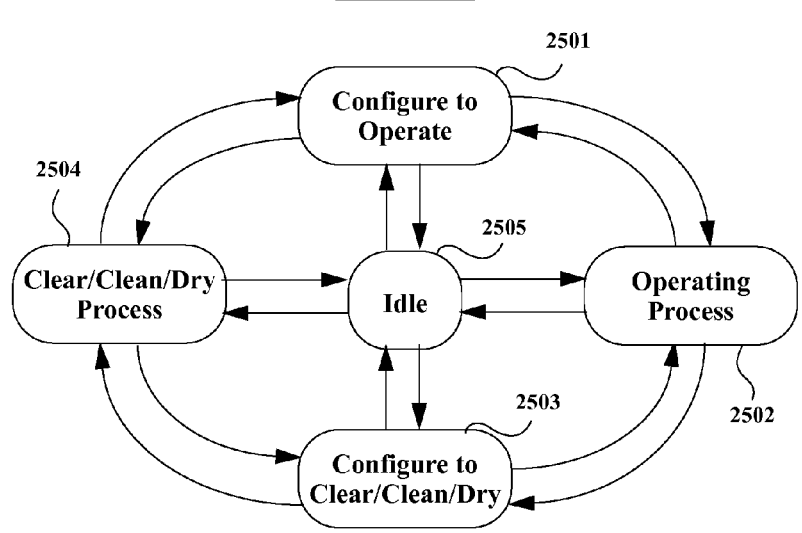

These were seen earlier in FIG. 6 and the four lowest-level control systems components in the above, i.e.:

Configuration management directed to assembling an operational configuration (for example 621 in FIG. 6);
  Configuration management directed to Clearing/Cleaning/Drying (for example 604 in FIG. 6);
  Process control directed to operating an operational configuration (for example 601, 623 in FIG. 6);
  Process control directed to Clearing/Cleaning/Drying (for example 602-603 in FIG. 6), were earlier grouped according to an alternate organization in FIG. 5 and FIG. 7*a*:

Process Control (for example 521, 523 in FIGS. 5 and 703.1-703.*n* in FIG. 7*a*):
    Process control directed to operating an operational configuration;
    Transition Control (for example 522 in FIG. 5, 704.1-704.*n* in FIG. 7*a*):
      Configuration control directed to Clearing/Cleaning/Drying;
      Process control directed to Clearing/Cleaning/Drying;
      Configuration control directed to assembling an operational configuration;

In the case of isolated operational threads for a given collection of chemical system elements, these lowest-level control system components typically would occur mutually exclusively. Additionally, intervals where chemical system elements are idle are also possible and likely. A composite view of some exemplary possibilities for such dynamics is depicted in the state transition diagrams provided in FIGS. 25*a*-25*c*. In the case of multiple operational threads for a given collection of chemical system elements, especially where some chemical system elements are shared among co-active operational threads, there can be exceptions to this mutual-exclusivity, but the operation in a given chemical system element of these lowest-level control system components will typically be mutually exclusive, as depicted in FIGS. 25*a*-25*c*. In FIG. 25*a*, one of the four lowest-level control system components 2501-2504 is active at any one given time. In FIG. 25*b*, an idle state 2505 is introduced that may be reached by any of the four lowest-level control systems components 2501-2504 and that can reach any of these four lowest-level control system components 2501-2504. This allows for pausing both between the operation of the four lowest-level control systems 2501-2504 as well as repeating any of them after a pause. Additionally, the state transition map of FIG. 25*b* as drawn further allows earlier control processes to be revisited, for example allowing a configuration change before a clearing/cleaning/drying action, or allowing a configuration change between epochs of clearing/cleaning/drying. FIG. 25*c* adds this capability without requiring traversal through the idle state 2505.

In many embodiments, these lowest-level control system components 2501-2504 may be in turn operate under higher levels of control, for example as provided by the strategic control elements 701, 710 depicted in FIGS. 7*a* and 7*b* and 1501 depicted in FIGS. 15*a*, 15*b*, and 15*c*. Within the strategic control elements 701 and 1501 there can be additional control structure of arbitrary complexity. In earlier discussions, these strategic control elements 701, 710, 1501 were discussed in the context of managing multiple threads of operation and larger-scale resource allocation and management. However, the strategic control elements 701, 710, 1501 can be used in some embodiments to provide an additional capability of interest and value in software programming, namely nested and hierarchical constructions. These are discussed next.

Nested and Hierarchical Constructions Useful for Software Development

A given procedure may often be separable into two or more sequential and/or parallel sub-procedures focusing on more detailed or lower-level tasks. This permits the given procedure to be implemented in at least two ways:

All of the more detailed or lower-level tasks are handled directly within the implementation of the given procedure, or
  The given procedure relies on at least one subordinate procedure (and often a plurality of subordinate procedures) to perform the more detailed or lower-level tasks.

Figure 26A:
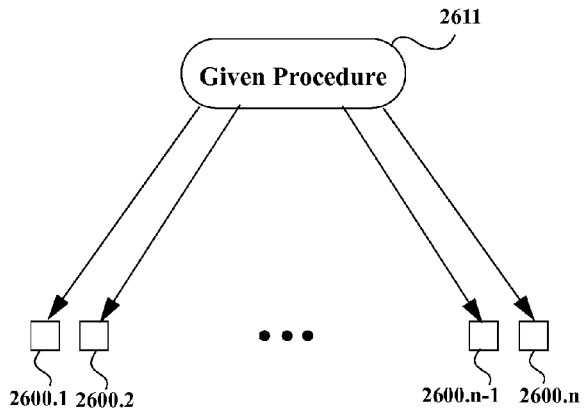
FIGS. 26a-26e depict exemplary procedures for directly controlling hardware resources.
Figure 26B:
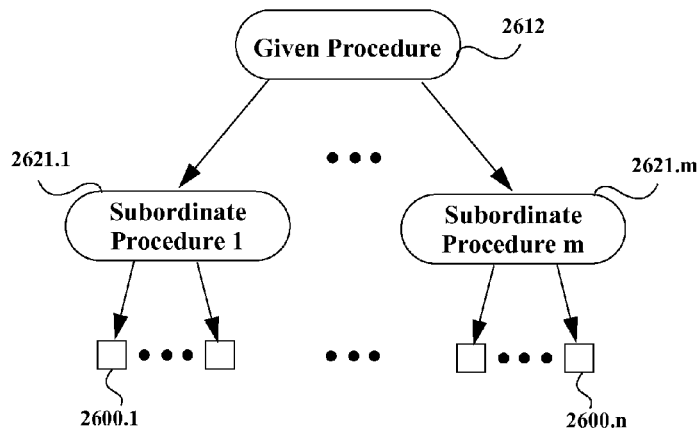

The examples of FIGS. 26*a*-26*e* illustrate these concepts. In FIG. 26*a*, a given procedure implementation 2611 directly controls all hardware resources 2600.1-2600.*n* required by the procedure. In FIG. 26*b*, the given procedure 2611 has an alternate implementation 2612 which in turn controls two or more subordinate procedures 2621.1-2621.*m*, each of which in turn controls all hardware resources associated with that particular subordinate procedure 2621.1-2621.*m*.

Figure 26C:
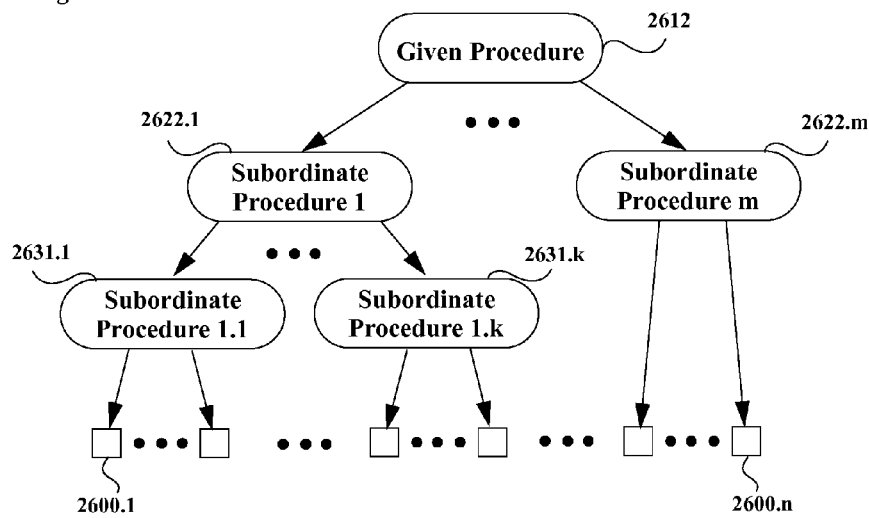

In FIG. 26*c*, the given procedure 2611 of FIG. 26*a* has an alternate implementation 2612 which in turn controls two or more subordinate procedures 2622.1-2622.*m* as in FIG. 26*b*. However, at least one subordinate procedure, here subordinate procedure 2621.1 in FIG. 26*b*, in a similar manner has alternate implementation 2622.1 which in turn controls two or more subordinate procedures 2631.1-2631.*k*, each of which in turn controls all hardware resources associated with that particular subordinate procedure 2631.1-2631.*k*. Note that the same implementation 2612 of the given procedure may be used in both FIGS. 26*b* and 26*c*; thus, the same or similar parent procedure can be used regardless of whether a subordinate procedure controls the resources directly or via further levels of one or more subordinate procedures.

Further aspects provide for the given procedure 2611 of FIGS. 26a and 2612 of FIGS. 26b and 26c to control some resources directly, as is done for all resources in the configuration of FIG. 26a. In the variation depicted in FIG. 26d of the configuration depicted in FIG. 26b, the given procedure 2612 of FIG. 26b has an alternative implementation, given procedure 2613, which, unlike the given procedure 2612, controls some of the resources 2600.1-2600.n of FIGS. 26a-26e directly. Similarly, in the variation depicted in FIG. 26e of the system depicted in FIG. 26c, the same given procedure 2613 of FIG. 26d, unlike the given procedure 2612 of FIG. 26c, controls some of the resources 2600.1-2600.n of FIGS. 26a-26e directly.

In this manner, several advantageous properties are obtained, including:

- a procedure may interact with hardware resources and subordinate procedures interchangeably;
- a procedure may employ mixed levels of subordinate procedures;
- in some embodiments, or via some additional minor modifications clear to one skilled in the art of computer programming, a procedure itself may be in turn used as a subordinate procedure in service to another procedure.

Figure 26D:
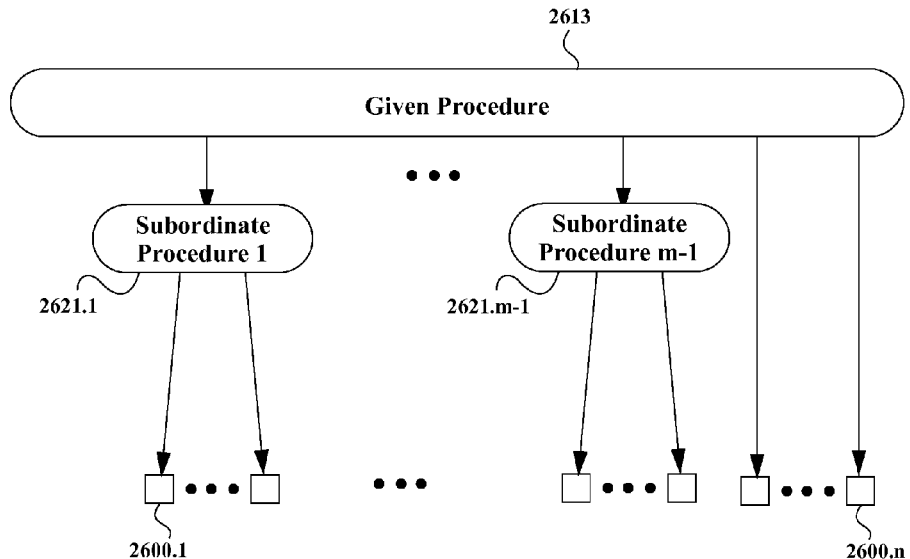
Figure 26E:
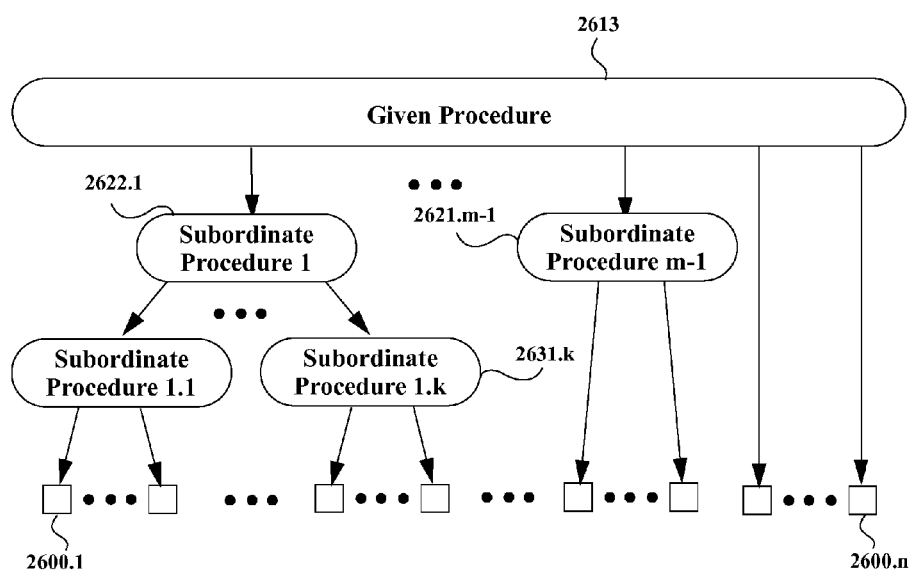

Although not depicted as such in FIGS. 26b-26d, it is also possible for a "parent" procedure such as 2611, 2612, 2613, or 2622.1 to control two or more subordinate procedures in such a manner that those subordinate procedures may co-control a shared hardware resource element. This can be accomplished by:

- message passing between each subordinate procedure and the parent procedure,
- message-passing directly among subordinate procedures, as well as other approaches. Such arrangements can approach the same level of tightly managed resource control that could be obtained in the direct implementation in which the given procedure 2611 communicates directly with the hardware resources 2600.1-2600.n depicted in FIG. 26a.

Before continuing with additional detailed aspects of software and programming, attention is momentarily returned to the lowest-level control system components 2501-2504 and their associated groupings previously described so as to consider details of transitions and associated transition costs which can have significant bearing on scheduling and cost optimization.

Transition Costs

There are at least two major applications contexts that employ the reconfigurable system aspects presented herein.

In a first context, embodiments of the invention are effectively configured once for the lifetime of the embodiment. This is akin to employing a general purpose microprocessor chip for running only one algorithm for its entire lifetime, as is the case for many embedded processors found in a plethora of commercial products. Even in this context, reaction operations and clearing/cleaning/drying operations may be intertwined for quality, maintenance, and other purposes.

In a second context, embodiments of the invention are effectively reconfigured many times over the lifetime of the embodiment, typically to support a plurality of types or family members of chemical reaction processes.

Within the second context of the reconfigurable system aspect of the invention, typically systems-level transitions are required between each stage of the chemical reaction process and the next. This has been called out repeatedly in earlier discussions, in particular in relation to FIGS. 1, 3a-3c, 5, 6, 7a-7d, 13a-13f, and 25a-25c. The ability to support a sequence of chemical reaction processes has significant value, but the reconfiguration transitions have a cost. These issues are considered in more detail in this section.

Figure 27:
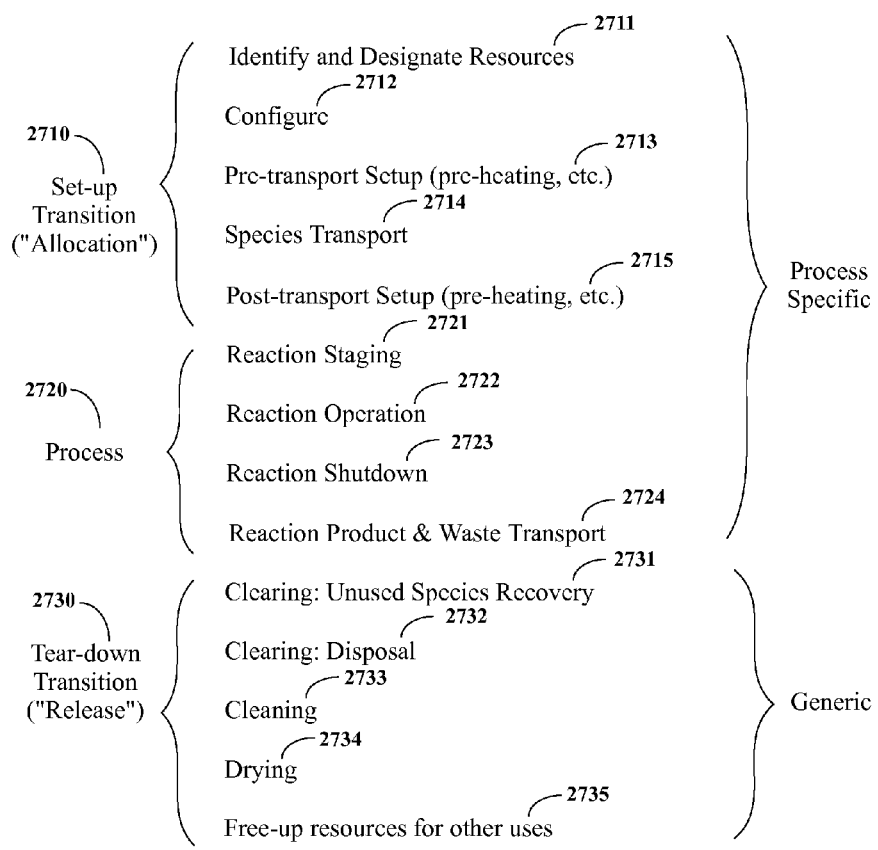
FIG. 27 depicts an exemplary sequence of events in an exemplary chemical reaction process life-cycle.

FIG. 27 depicts an exemplary sequence of events in an exemplary chemical reaction process life-cycle for the set-up, operation, and tear-down within the context of the reconfigurable system aspect of the invention. One skilled in the art will recognize that many variations of this exemplary list are possible yet still lie within the scope and spirit of the invention. For example, the sequence below assumes each chemical reaction process is completely independent of the previous and following ones. But in many applications it may be advantageous to share arrangements and/or preparations with previous or subsequent chemical reaction processes, skip steps in the list, etc. The exemplary chemical reaction process life-cycle, as shown in FIG. 27, can be described as follows:

First is the set-up transition ("Allocation") 2710, which comprises the following steps:

- Appropriate chemical system elements are identified and designated 2711 to be used for the reaction so as to support a particular type or family of chemical reaction process;
- These chemical system elements are configured 2712 so as to support the chemical reaction process;
- Any pre-reaction preprocessing (filtering, pre-heating, dilution, etc.) 2713 of chemical species that may be required prior to the reaction is then performed;
- Next the required species are transported 2714 (in any required or advantageous specific ordering) to the chemical reaction element;
- Any additional preprocessing (mixing, pre-heating, aeration, etc.) 2715 of the contents of the chemical reaction element that may be required prior to the reaction is then performed.

Note that the details of each of these operations are typically specific to the type or family of chemical reaction process.

Next is the actual chemical reaction process 2720 itself, which comprises the following operations:

- Any chemical reaction staging 2721 is performed;
- The chemical reaction itself 2722 is performed (this may include waste removal, such as gas venting);
- The chemical reaction shutdown operation(s) 2723 is (are) performed;
- Products and wastes from the chemical reaction are then transported 2724 from the chemical reaction.

Note that again, in general the details of each of these operations are typically specific to the type or family of chemical reaction process. In some simple or special purpose embodiments, however, it may be advantageous for the product and waste transport operation 2724 to be made sufficiently general to cover all chemical reaction processes supported by the embodiment.

Finally there is the tear-down transition ("Release") 2730, which comprises the following operations:

- If appropriate for the embodiment, any unused chemical species recovery capabilities 2731 are put into operation so as to recover at least some of the unused chemical species from chemical system elements and appropriate transport conduits (typically though use of a clearing gas);
- Any remaining unused chemical species and reaction products are cleared 2732 from chemical system elements and appropriate transport conduits (typically though use of a clearing gas) and disposed of (or directed to exogenous recovery systems);

The chemical system elements and appropriate transport conduits are then cleaned 2733 by rinsing with one or more appropriate solvents, with the results disposed of (or directed to exogenous recovery systems);

Next the chemical system elements and appropriate transport conduits are dried 2734 (typically though use of a clearing gas);

The chemical system elements employed are then freed 2735 for other uses.

Note that, in general, the details of each of these operations are in general generic to the type or family of chemical reaction process and depend only on the previously assembled configuration. One notable exception is for portions of the systems where only gases are involved, in which case the cleaning and drying steps may advantageously be skipped.

Figure 28:
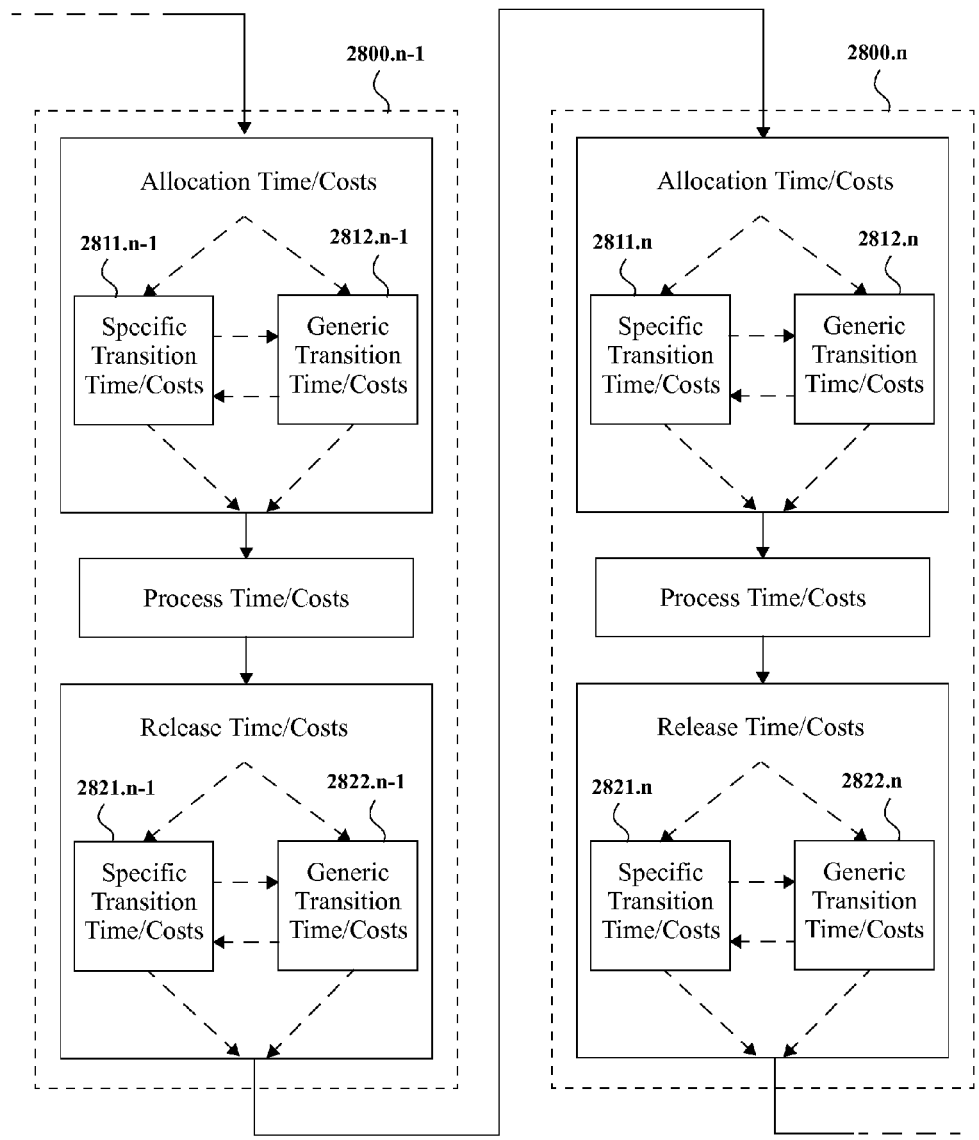
FIG. 28 illustrates a temporal sequence of two chemical reaction life-cycles reflecting the potential for interleaving generic and process-specific transition costs.

In this exemplary event sequence, it is seen that there are time and costs associated with an "allocation" phase of the life-cycle preceding the desired chemical reaction process and time and costs associated with a "release" phase of the life-cycle following the desired chemical reaction process. Further it is seen that, at least in the provided example, there can be both generic and process-specific components of these allocation and release times and costs. FIG. 28 illustrates a temporal sequence of two from a plurality of such chemical reaction life-cycles 2800.$n-1$, 2800.$n$ reflecting the potential for interleaving generic 2812.$n-1$, 2822.$n-1$, 2812.$n$, 2822.$n$ and process-specific 2811.$n-1$, 2821.$n-1$, 2811.$n$, 2821.$n$ components of these allocation and release times and costs.

In the case where each chemical reaction is independently handled, the process-specific components of allocation and release times and costs would depend only on the particular process the allocation and release intervals envelope. In other situations, the process preceding and/or process to-follow may affect the process-specific components of allocation and release times and costs.

Various implementations provide for controllers, schedulers, and optimizers to include such transition time and cost considerations in the programming and/or operation of embodiments of the invention. Such implementations will be described in more detail below.

Control Software

Attention is now directed to control software for controlling the various configuration and operation activities and events described herein.

1. In an exemplary minimal implementation, such software would:

Support a modest to wide range of chemical reaction processes;

Provide a programmable function for configuring the reconfigurable chemical process system in a specific way;

Provide a programmable function for the basic operation of the reconfigurable chemical process system in that configuration, according to a specified process;

This could comprise only a single chemical process, but could alternatively comprise multiple simultaneous chemical processes.

2. At a next level of sophistication, the software would further, for example:

Provide a programmable function for the clearing, cleaning, and drying of chemical system elements within the embodiment at the conclusion of the chemical reaction process.

3. At yet another level of sophistication, the software would further, for example:

Provide a programmable function for the clearing, cleaning, and drying of chemical system elements within the embodiment at the conclusion of the chemical reaction process.

4. At yet another level of sophistication, the software would further, for example:

Provide a programmable function for the sequential reconfiguration and operation of multiple sequential chemical reaction processes through the use, clearing/cleaning/drying, and reuse of chemical system elements.

5. At yet another level of sophistication, the software would further, for example:

Provide a programmable function for scheduling the sequential reconfiguration and operation of multiple sequential chemical reaction processes.

This could comprise only a single chemical process, but could alternatively comprise multiple simultaneous chemical processes.

6. At yet another level of sophistication, the software would further, for example:

Provide a programmable function for the a priori optimization of the scheduling of the sequential reconfiguration and operation of multiple sequential chemical reaction processes.

7. At yet another level of sophistication, the software would further, for example:

Provide a programmable function for the real-time in situ optimization of the scheduling of the sequential reconfiguration and operation of multiple sequential chemical reaction processes.

Other constructions, attributes, and requirements as may be driven by need, practical considerations, or commercial opportunities will be clear to one skilled in the art.

Figure 29:
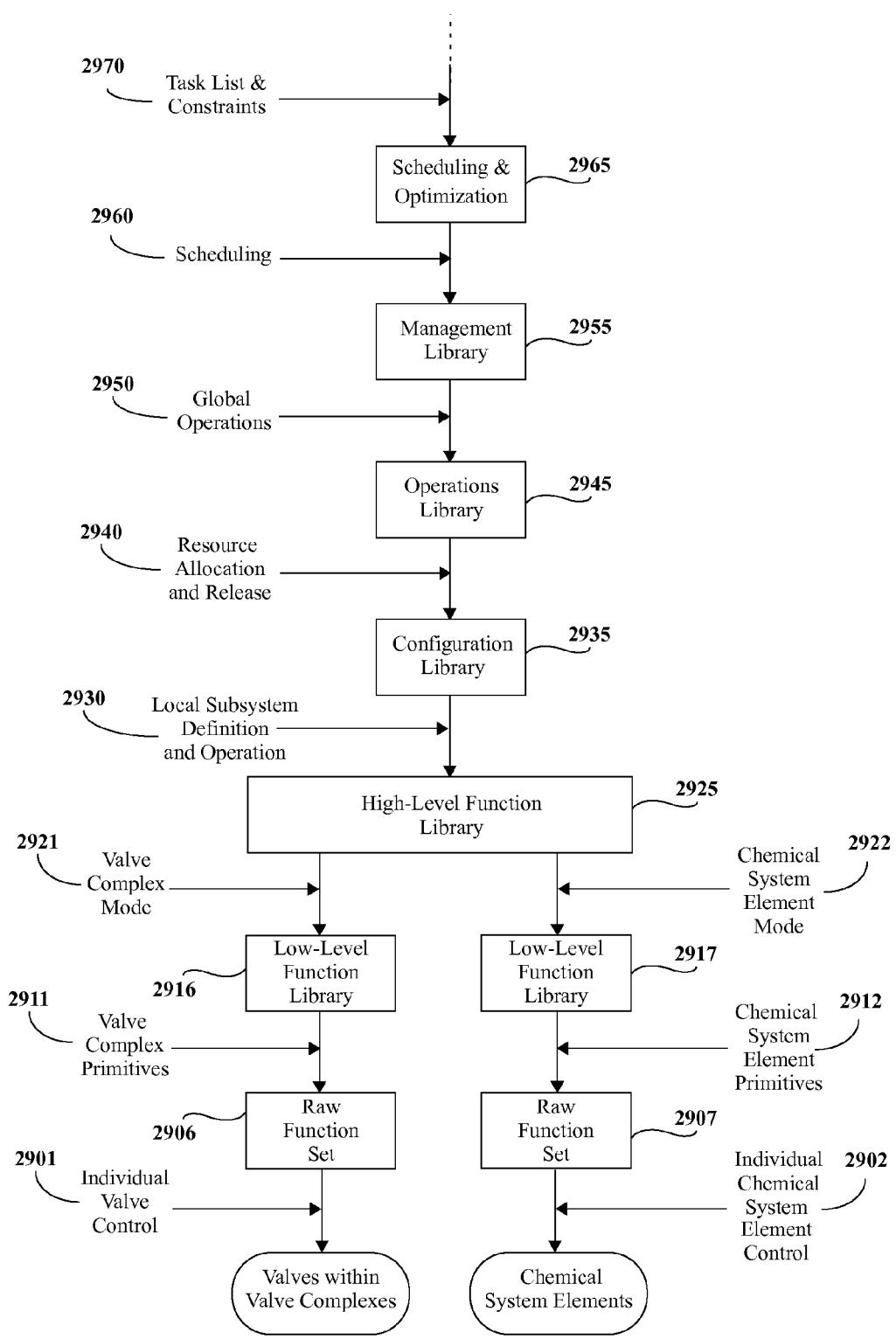
FIG. 29 illustrates an example control software structure and interfaces comprised by an exemplary a multi-level control hierarchy.

FIG. 29 illustrates an example of one type of cascade of control software attributes and requirements in the form of a multi-level control hierarchy with the understanding that one skilled in the art may choose other implementations. At the most primitive levels of instructions are the direct control commands 2901 for the control of individual valves within valve complexes and the direct control commands 2902 for the control of individual chemical system elements. The collection of these commands may be, respectfully, assembled into a raw function set 2906 for the valve complexes and a raw function set 2907 (i.e., "on," "off," flow rate values, etc.) for other chemical system elements. These raw functions may be treated as primitives 2911, 2912 by corresponding low-level function libraries 2916, 2917 which can be used to operate individual valve complexes and chemical system elements, respectively, according to aggregate operating modes. For example, a valve complex may be instructed to activate modes such as "Flow Species 2," "Clear Species 1," etc, which would require the controlled operation of multiple valves. In some embodiments, these low-level function libraries 2916, 2917 may in some instances also include more complex commands, such as short sequences of valve modes.

Entries in these low-level function libraries 2916, 2917 may be used by higher-level library functions residing in a high-level function library 2925. The functions in this high-level function library 2925 may comprise, in this example, definitions 2930 of local subsystems that comprise chemical system elements which are linked by pathway conduits realized by valve complex configurations. In some embodiments, the functions in this high-level function library 2925 may also or alternatively comprise, in this example, operational modes of the resulting local subsystem definitions.

Entries in the high-level function library 2925 may be used by configuration library functions residing in a configuration library 2935. In some implementations the entries in this configuration library 2935 may be static, explicitly a priori comprising all possible configurations supported by the embodiment of the invention. In other implementations the entries in this configuration library 2935 may be entirely dynamic, defined as the result of resource allocation commands 2940 resulting from calculations and decisions made above it, for example as resulting from actions of functions residing in the operations library 2945. In some embodiments, the functions in this operations library 2945 may also or alternatively comprise, in this example, global operations 2950 pertaining to a larger segment, or indeed the entire embodiment, of the invention. These global operations 2950 could pertain to only a single chemical process, but could alternatively pertain to multiple simultaneous chemical processes.

These global operations 2950 and associated functions in the operations library 2945 could be managed using algorithms in a management library 2955. In some embodiments, the management algorithms offer programmable functions for the real-time operation of multiple sequential chemical reaction processes.

If desired, these management algorithms offer programmable functions for the a priori and real-time in situ optimization and scheduling of the sequential reconfiguration and operation of multiple sequential chemical reaction processes. The management algorithms may be used, for example, by algorithms and functions in a scheduling and optimization library 2965, which makes optimization and scheduling decisions based on an incoming task list and specified constraints 2970. In some embodiments, the optimization criteria may be built into the algorithms and functions in the scheduling and optimization library 2965. In other embodiments, the optimization criteria may be partially or fully provided by external data, algorithms, etc.

It will be apparent to one skilled in the art that there are many variations of the example of FIG. 29 that address the exemplary numbered list of features of and requirements for control software provided at the beginning of this section, and as such are within the scope and spirit of the invention. Other constructions, attributes, and requirements as may be driven by need, practical considerations, or commercial opportunities will be clear and available to one skilled in the art.

A software event flow among elements of a functional hierarchy, such as the exemplary arrangement shown in FIG. 29, can be used to define a programming environment and/or programming language hierarchy. For example, each of the types 2901, 2902, 2911, 2912, 2921, 2922, 2930, 2940, 2950, 2960, 2970 of function calls depicted in FIG. 29 can be treated as programming interfaces or portals into the underlying (or "native" system as described thus far. Thus some or all of the types of function calls 2901, 2902, 2911, 2912, 2921, 2922, 2930, 2940, 2950, 2960, 2970 may be made using either libraries 2906, 2907, 2916, 2917, 2926, 2927, 2935, 2945, 2955, 2965 or via this programming interface or portal.

The programming interface or portal may be presented to a programmer as a low-level (or "raw") instruction set (similar to an assembly language) Application Programmer Interface (API), or may be formalized into a richer interpretive language Application Programmer Interface, or developed yet further into a broader Software Development Kit (SDK) providing a more extensive and well-supported applications-level programming environment. By offering access to the hierarchy of function calls 2901, 2902, 2911, 2912, 2921, 2922, 2930, 2940, 2950, 2960, 2970, a wide range of user interfaces can be developed so as to support a wide range of programmers and direct users. More regarding this wide range of user interfaces and user bases will be discussed below.

Figure 30:
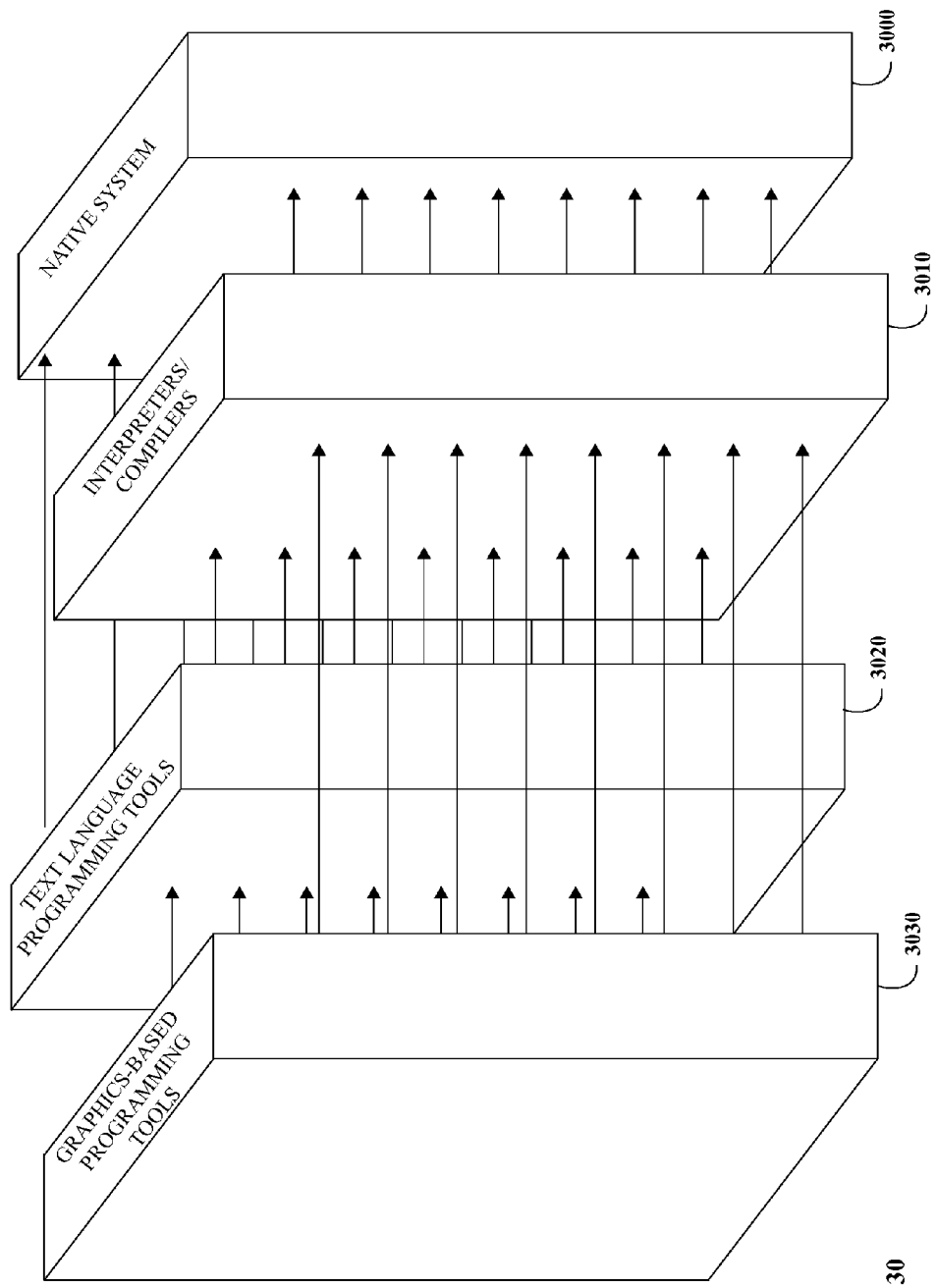
FIG. 30 illustrates an exemplary software development environment used with native system aspects associated with underlying hardware infrastructure.

FIG. 30 illustrates an exemplary software development environment that could be used with native system aspects of the invention associated with the underlying hardware infrastructure. In this example, the native system 3000 may be directly accessed through at least one level of the hierarchy of function calls 2901, 2902, 2911, 2912, 2921, 2922, 2930, 2940, 2950, 2960, 2970 via text-based programming tools 3020 and/or interpreters/compilers 3010. The text-based programming tools 3020 and/or interpreters/compilers 3010 may be used directly so as to present a text-based program development environment to the application programmer. Additionally or alternatively, the text-based programming tools 3020 and/or interpreters/compilers 3010 may be accessed by graphics-based programming tools 3030. The graphics-based programming tools 3030 may present the utilities of the text-language programming tools 3020 and/or interpreters/compilers 3010 to the user in a limited way, or present, in some form, at least some of the broader range of choices inherent in the hierarchy of function calls 2901, 2902, 2911, 2912, 2921, 2922, 2930, 2940, 2950, 2960, 2970.

The native system will find broadest usage if a wide range of programming interfaces can be offered across the widest possible user base. In its full glory, programming can be a highly specialized interdisciplinary affair comprising chemistry/biochemistry/biology, process control, feedback system design, computer programming, parallel processing, scheduling theory, and exotic optimization techniques. However, many applications may be quite simple and the market could be considerably expanded if the user interfaces could be brought into realms more familiar to chemists, biologists, non-specialized process engineers, generic product developers, and even a range of hobbyists.

In one programming language approach, the native system 3000 may be programmed, via an interpreter and/or a compiler 3010, using a BASIC-type text-based language such as PBasic created by Parallax, Inc., 599 Menlo Drive, Suite 100, Rocklin Calif. 95765 for use with their BASIC Stamp® product line. As with the PBasic, simple commands are provided for chemical system element and routing configurations and functions unique to the native system 3000, and these are embedded into the broader well-known and readily-learned BASIC language for incorporating hand-coding of algorithms to even first-time programmers.

For more seasoned programmers, the approach described above may be adapted for the MPLAB® IDE model of the PIC® processor family provided by Microchip Technology Inc., 2355 West Chandler Blvd., Chandler, Ariz. 85224. In fact the Parallax BASIC Stamp® product line incorporates PIC processors, but adds an active on-board interpreter. In particular, Microchip Technology Inc. has developed the programming environment to include a mature C-language implementation. In some embodiments of the invention, the RISC framework of the PIC processor programming language model would require considerable expansion of the RISC instruction list.

In a computer-oriented lab technician approach, the native system 3000 may be incorporated, via interpreter and/or compilers 3010 and text language programming tools 3020 into established laboratory instrumentation and automation environments such as LabVIEW® made by National Instruments Corporation, 11500 N Mopac Expressway, Austin, Tex. 78759. In particular, LabVIEW offers a graphics-based programming environment 3030 with object-oriented capabilities that is well established, has an open, extensible architecture, and already is integrated with a wide range of other laboratory and process control products and software systems. Additionally, LabVIEW's graphical dataflow programming language includes a math-oriented text-based programming language (MathScript®) which is very useful for implementing the mathematical functions necessary for operational process control as is well-known to one skilled in the art. More on process control is provided below.

In yet another approach, programming languages and programming environments for programming the native system 3000 may be modeled upon programming languages and programming environments for signal processing chips. This approach offers some noteworthy synergies as signal processing environments are naturally applicable to implementations of process control systems in that these control systems comprise or closely resemble filters, limiters, and other classic signal processing elements (as is well-known to one skilled in the art or may be found in many books such as that by Thomas E. Martin, *Process Control: Designing Processes and Control Systems for Dynamic Performance*, McGraw Hill, New York 1995, ISBN 0-07-040491-7). There are many text-based, object-oriented, graphics-based, and concurrent programming languages and programming environments that that have been developed for signal processing, for example:

- the C-related language DSPL (see for example A. Schwarte & H. Hanselmann, "The Programming Language DSPL", Proc PCIM 90, 1990 and http://www1.cs.columbia.edu/~sedwards/classes/2006/w4115-fall/whitepapers/DSPL.pdf);
- GABRIEL (see for example E. A. Lee, et. al., "GABRIEL: a design environment for programmable DSPs," Proceedings of the 26th ACM/IEEE Conference on Design Automation, June 1989);
- GOSPL (see for example C. D. Covington et. al., "Graphic Oriented Signal Processing Language—GOSPL", Proc ICASSP-87, 1987).

In one embodiment, the native system 3000 may be co-programmed with a signal processor family in a common signal software development environment.

As for scheduling, in one type of approach skilled programmers may hand-code specialized algorithms based on a wide range of applicable techniques such as those found in the large survey book by Joseph Y-T. Leung, *Handbook of Scheduling Algorithms, Models, and Performance Analysis*, Chapman & Hall/CRC, Boca Raton, 2004, ISBN 1-58488-397-9.

Functions and algorithms such as those found in the Leung survey book may be adapted for the native system 3000 and incorporated into libraries such as that 2965 depicted in FIG. 29, may be provided elsewhere within the programming environment depicted in FIG. 30, or as may be linked to the programming environment depicted in FIG. 30.

Alternatively, in a simple approach to scheduling, a familiar scheduling program such as the very well-known Microsoft Project® product of Microsoft Corporation may be employed as a graphics-based programming tool 3030 to create and export a comma-separated file for the hard-scheduling of events and processes within the native system 3000. The comma-separated file would be interpreted by specialized interpreter and/or compiler operations and entities 3010.

Established scheduling theory, both informal versions such as that underlying Microsoft Project®, and formal, academic versions provide little help for understanding the full range of transition time and transition cost considerations and phenomena that would be encountered in reconfigurations, but these can be at least reasonably approximated by treating them as various types of fixed costs, startup delays, and overheads.

Exemplary Applications

Figure 31:
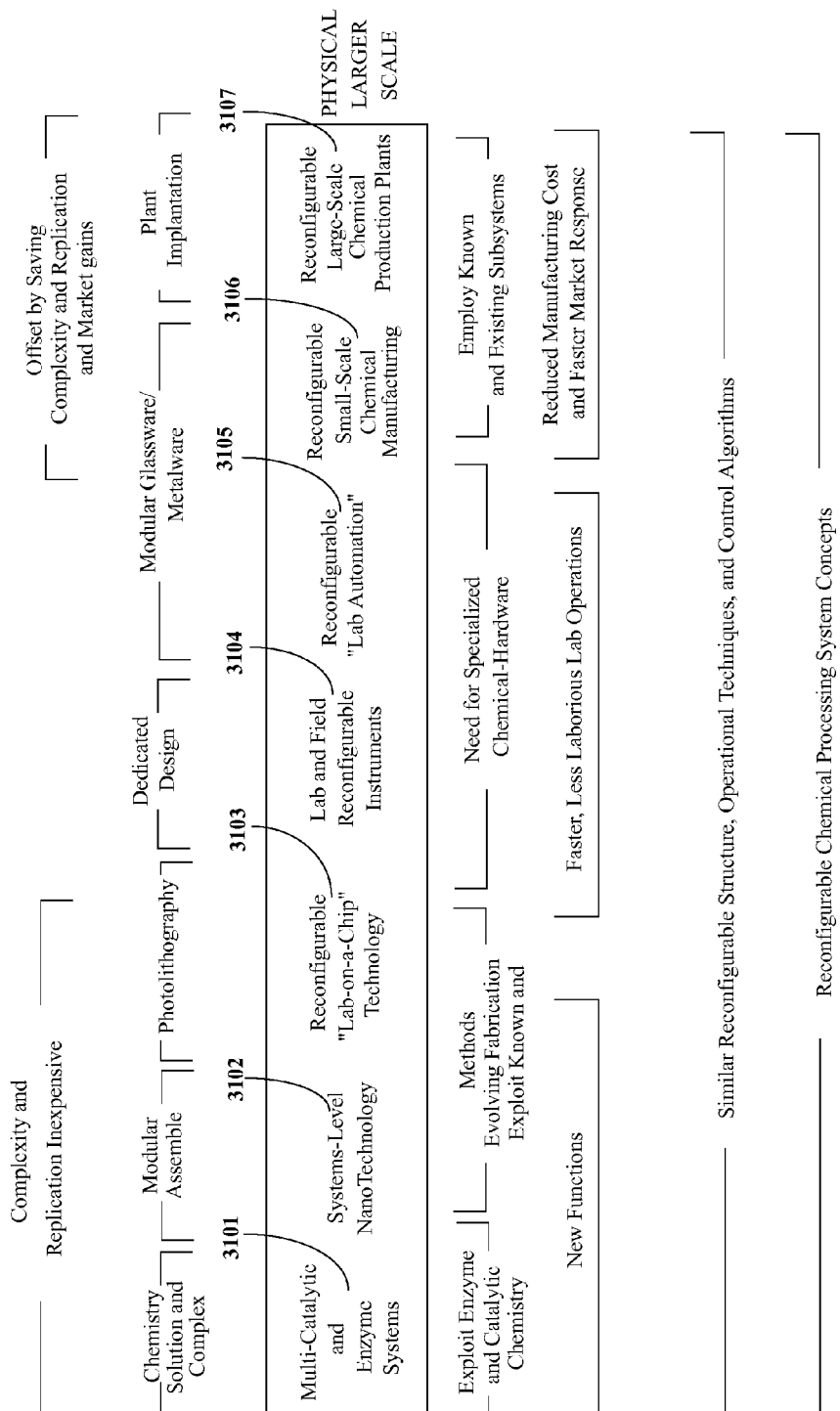
FIG. 31 shows a detailed taxonomy of exemplary attributes and applications for reconfigurable chemical process systems.

The reconfigurable chemical system technology described herein has many applications as touched on earlier in the discussion relating to FIG. 9. FIG. 9 divides these potential applications into two general classes:

Physically Partitioned Chemical Reaction Systems:
Microscale hybrid-process chips
"Lab-On-A-Chip"
Multiple "Lab-Chip" systems
Field-scale instruments
Laboratory-scale Instrument and devices
Chemical production plants
and
Physical Co-Mingled Chemical Reaction Systems:
Catalytically-activated systems
Enzyme networks
Exogenously activated systems FIG. 31 shows a more detailed taxonomy of exemplary applications for reconfigurable chemical system technology. The applications are arranged along a spectrum of increasing scale. The spectrum includes, from smallest scale to largest scale:

Multi-catalytic and enzyme systems 3101,
Systems-level nanotechnologies 3102,
"Lab-on-a-Chip" technology 3103,
Laboratory and field reconfigurable instruments 3104,
Laboratory automation of conventional chemical laboratory glassware and related technology 3105,
Small-scale chemical manufacturing 3106,
Large-scale chemical production plants 3107.

Aspects of FIG. 31 will be discussed throughout the subsections to follow.

Recall that although the discussion thus far and to follow are made in terms of chemical species, chemical reactions, and chemical products, and chemical wastes, embodiments of the invention can be used in biosystems and life-sciences applications. In these embodiments, modifications such as the following can be made:

"Chemical species," "chemical products," and "chemical wastes" would be replaced with more complex substances such as microorganism serums, etc.;
"Chemical reactions" would be replaced with "bioreactions;"
"Chemical system elements" would be replaced with "bioreaction system elements."

Multi-Catalytic and Enzyme Systems Embodiments and Applications

At the smallest physical scale depicted in FIG. 31 are multi-catalytic and enzyme systems 3101 occurring in solutions, complexes, augers, serums, etc. at the macromolecular level. Various principles presented herein may be adapted to the chemical pathways and micro-local reaction environments within these solutions, complexes, augers, serums, etc. Valves and physical routing paths are replaced by reaction inhibitors, catalysis, and reaction pathways. Applying these systems and methods adds new functions and organizations, as well as exciting possibilities for the creation and synthesis of chemical and biological products, product production, and chemistry-based computing.

Systems Nanotechnology Embodiments and Applications

At the next largest physical scale in the spectrum depicted in FIG. 31 are systems-level nanotechnologies 3102, a field which is currently developing very rapidly. Although there is some overlap with the molecular-scale world described above, at nanometer scale entities such as tubes, valves, motors, and enclosed reactions are being developed with features and methods which are expanded by the month. Here modular assembly is readily possible through molecular assembly and optical techniques. Applying the systems and methods presented herein adds a new applications framework and many new areas of potential applications to this rapidly expanding field.

Lab-on-a-Chip Embodiments and Applications

Of particular interest is the next largest physical scale in the spectrum depicted in FIG. 31, the micrometer-scale to millimeter-scale of fabrication that is associated with the rapidly growing area of "Lab-on-a-Chip" technology 3103.

Figure 32A:
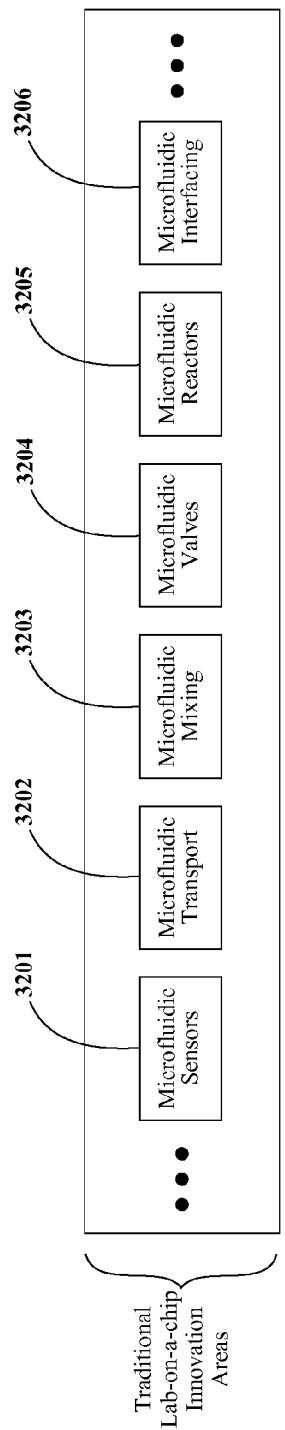
FIGS. 32a-32b illustrate views of currently active "Lab-on-a-Chip" technology research and development combined with selected aspects of the invention.
Figure 32B:
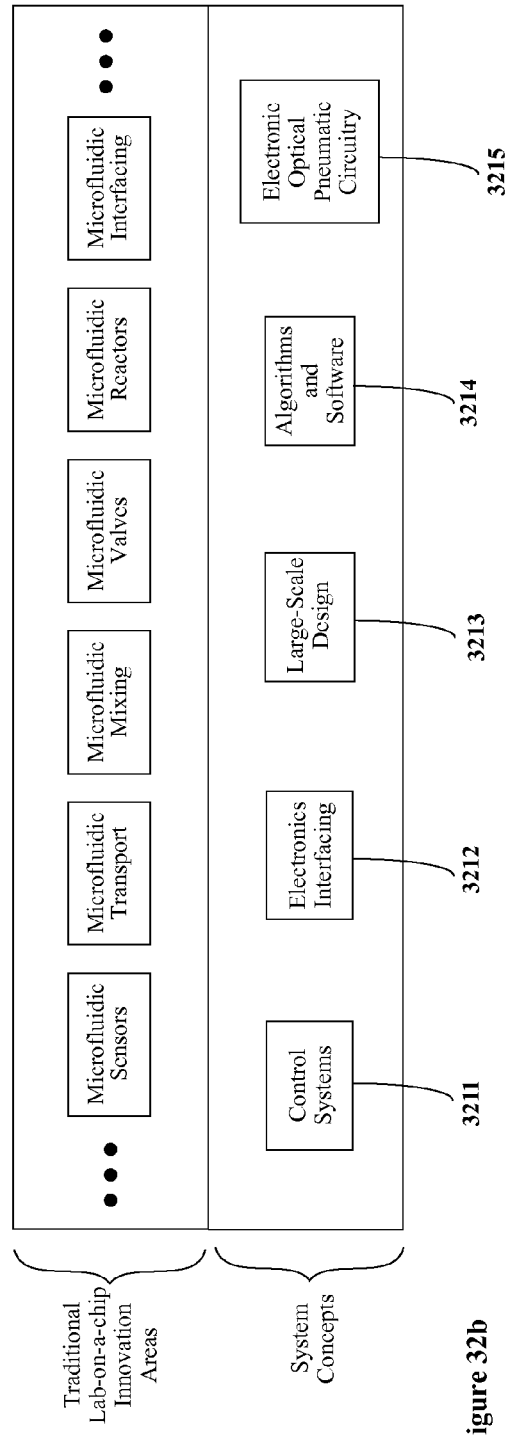

FIG. 32a illustrates several areas of currently active "Lab-on-a-Chip" technology research and development. To date, most "Lab-on-a-Chip" research and development is directed towards microfluidic systems with limited treatment of micro-scale gas flows and gas management. Active research and development areas include a widening array of isolated microfluidic sensors 3201, microfluidic transport technology 3202, microfluidic mixing technology 3203 (which at microfluidic scales cannot adequately rely on diffusion), microfluidic valves 3204, microfluidic reactors 3205, and microfluidic system interfacing 3206 with flows, species, and energy of the outside world Importantly, previous work related to processes that may be performed by a "Lab-on-a-Chip" entity has almost always, if not completely, been concerned with single process implementations with very narrow applications such as DNA sequencing and assay. By applying the systems and methods presented herein, these active innovation areas 3201-3206 are brought together, as shown in FIG. 32b, with control systems 3211, electronics (as well as optical) interfacing 3212, large-scale design 3213, formal algorithms and software 3214, and electronic, optical, and pneumatic "circuitry" 3215 to synergistically create a fundamental new capability explicitly provided for by various embodiments. The resultant new technology could be called "Reconfigurable Lab-on-a-Chip" or "reconfigurable lab chips."

The resultant new "reconfigurable lab chip" technology inherits much from existing "Lab-On-A-Chip" technologies and research trends:
  Usage of small amounts of chemicals; usage of species in very small-scale chemical processes;
  Fabrication from small amounts of materials;
  Fabrication derived from electronic chip fabrication (photolithography, etching, masking, metallization, ion implantation, chemical doping, etc.);
  Evolving micro-machining fabrication techniques;
  Co-integration of electronics, electro-optics, and photonics system elements;
  Very active innovation areas 3201-3206 as depicted in FIG. 32a;
  Ways of thinking about research and applications that inspire further interest and investment.

Figure 33:
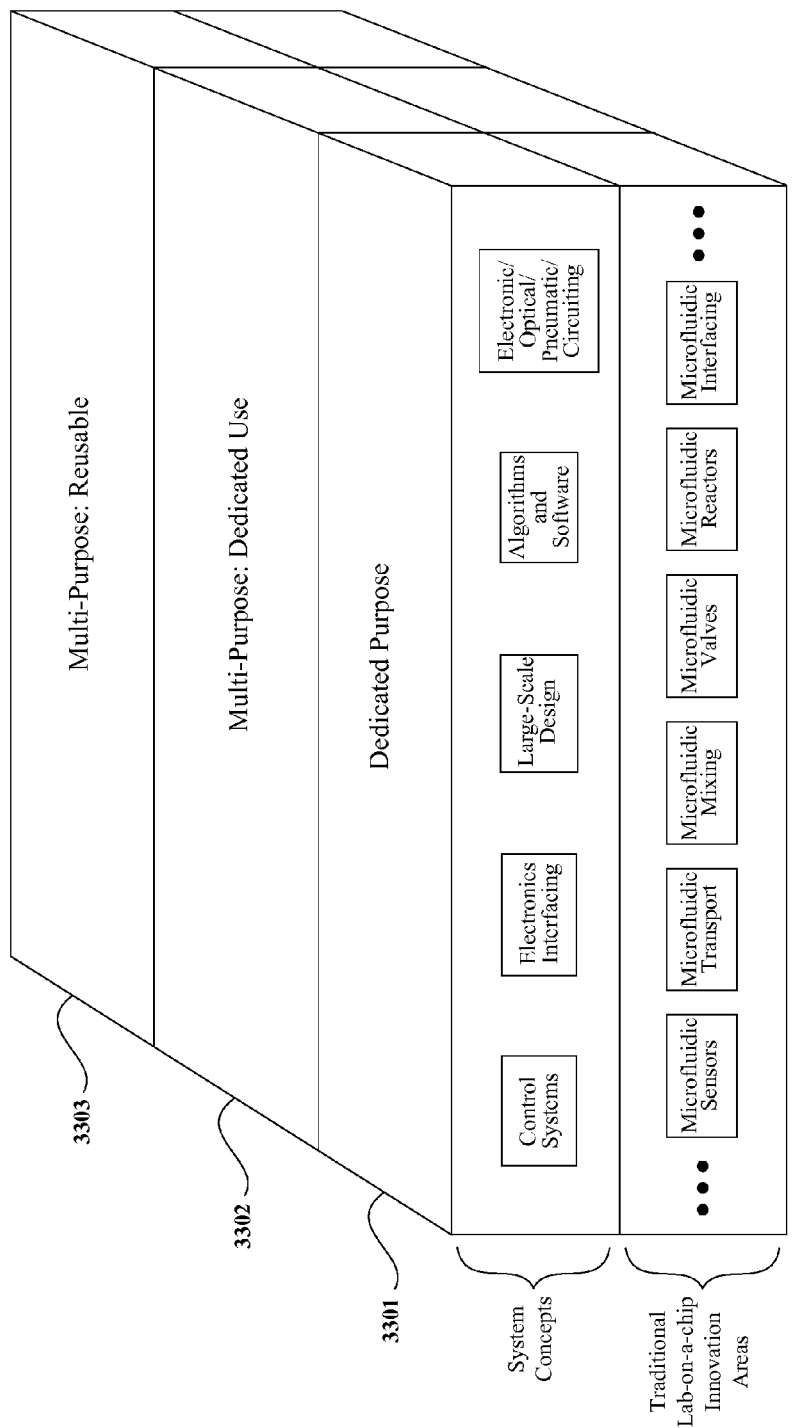
FIG. 33 depicts multi-configuration and multi-use over a lifetime.

Although aspects of the invention can be readily directed to multi-configuration multi-use over an embodiment's lifetime, a wide spectrum of usage is possible due to size, economics, and flexibility, as suggested in FIG. 33:
  Dedicated embodiments where the degree of reconfigurability is limited 3301:
    one-time operation;
    multiple-use;
  Multiple-purpose embodiments that are dedicated to a specific use 3302:
    one-time operation;
    one use;
  Multiple-purpose embodiments that are often or regularly reused for a variety of chemical processes 3303.

Even in cases of one-time use, the cleaning capabilities described herein could advantageously be used to detoxify a used embodiment entity prior to recycling or disposal.

The systems and methods presented herein may be implemented to create a fundamental new technology of inexpensive, multi-purpose, reusable microliter- and nanoliter-scale chemical processors. The resultant "reconfigurable lab chips" could be used to open many doors for chemical and biological processing. In particular, they may be embedded in larger systems like microprocessor and signal processing chips. In some applications, the chip could be used as the centerpiece of a system, while in other applications one or more such chips could be used as components of considerably larger systems.

A vast number of commercial applications may be realized including consumer products, medical implants, medical diagnostic devices, laboratory instruments, field environmental monitoring gear, inexpensive widely deployed food safety testing systems, and a host of others are made possible by the "reconfigurable lab chip" technology, for example.

Additionally, "reconfigurable lab chip" technology facilitates tremendously valuable research possibilities. Three of these are described below.

As a first valuable application to life science research, "reconfigurable lab chips" could be used to explore chemical computation and communication. In living systems, almost all communications, computations, and in fact signal processing is done with chemical and biochemical means. However, human understanding of the types and operation of chemical and biochemical computation and communication is quite limited, and human-design capabilities for these are in their infancy, relegated largely to pharmaceutical drug discovery/development employing minor modifications to existing metabolic and chemical signaling pathways.

As a second valuable application to life science research, the "reconfigurable lab chips" could be used to explore the ultimate reconfigurable and adaptive system, the immune systems of living organisms. Emulations of immune system elements can be implemented and analyzed, employing various degrees of chemical, biochemical, electronic, and photonic realizations of communications, computations, and signal processing.

As a third valuable application to life science research, the "reconfigurable lab chips" could be used to emulate the metabolism of living cells. Emulations of increasingly complex aspects of cell metabolism can be implemented and instrumented, again employing various degrees of chemical, biochemical, electronic, and photonic realizations of communications, computations, and signal processing.

Figure 34:
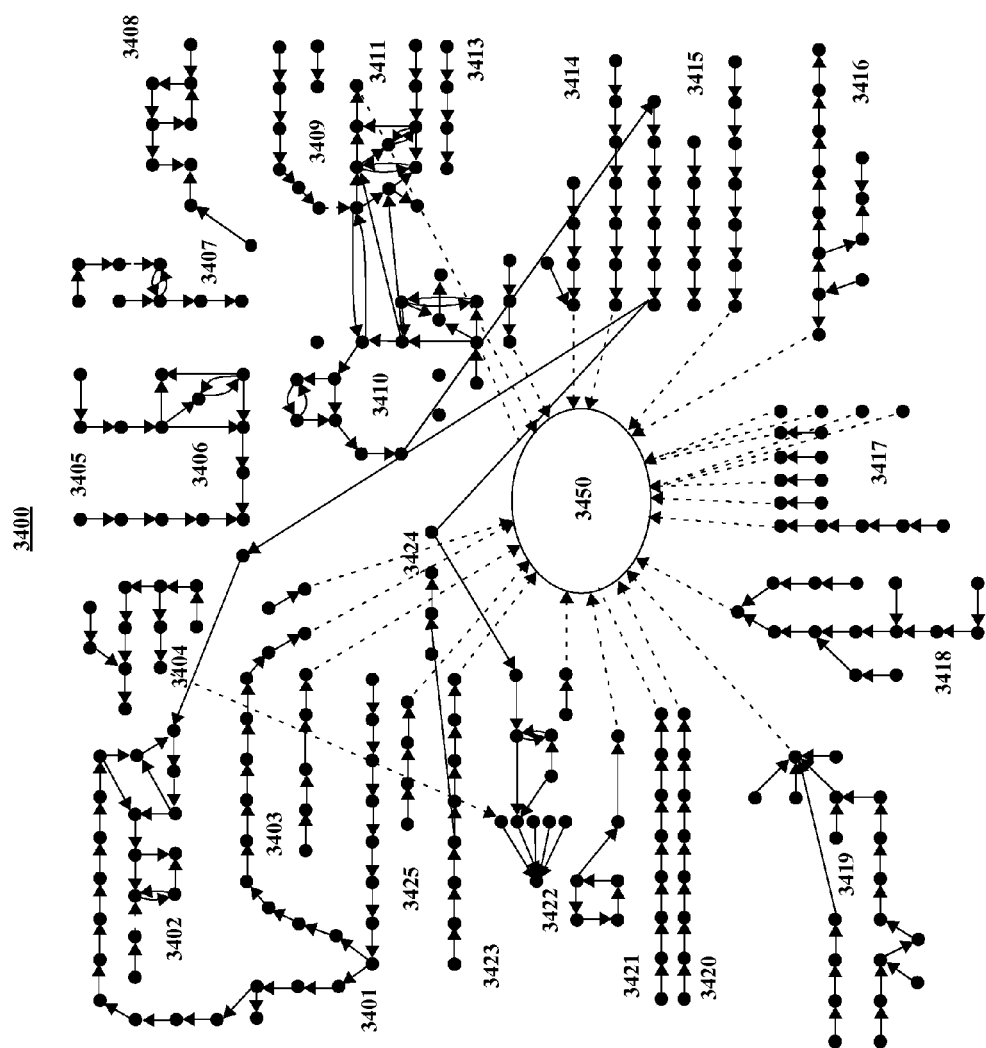
FIG. 34 shows a representation of a metabolic network representing a high-level view of the overall (glutamate-rich substrate) constituents and metabolic pathway structure associated with the bacterium Escherichia coli.

As an example of this third application to life science research, FIG. 34 shows a (flux-balance analysis type) representation of a metabolic network 3400 representing a high-level view of the overall (glutamate-rich substrate) constituents and metabolic pathway structure associated with the bacterium *Escherichia coli* (after and abstracted from FIG. 3 of the *Letters to Nature* article by E. Almass, B. Kovacs, T. Vicsek, Z. Pltval, A.-L. Barabast "Global Organization of metabolic fluxes in the bacterium *Escherichia coli*," NATURE, Vol. 427, No. 26, February 2004). This metabolic network 3400 comprises twenty-five small-scale known biological pathways 3401-3425 many of which are linked (as indicated with dotted lines) to the cell's biomass growth reaction 3450. These pathways together make use of approximately 250 chemical and biochemical compounds.

Embodiments of the present invention as a "reconfigurable lab chip" permit tightly-controlled and easily monitored implementations of this metabolic network 3400 and its twenty-four biological pathways 3401-3425. Of special note is because a cell metabolism is being emulated, there is no need for "reconfigurable lab chip" embodiments used here to support widely varying temperature gradients. The resulting implementations of various kinds of biochemical networks can be coupled to and interact with exogenous biochemical stimulus and/or computer control. Computer control can be used to emulate in situ and test vector conditions on these biochemical networks. Because of the described reconfiguration capabilities, for example, there is no need to fabricate a custom "Lab-on-a-Chip" for each kind of biochemical network. The reconfigurable conduit routing capabilities permit controlled isolation of pathway segments. Larger-scale emulation can be performed by defining appropriate chemical and electronic control interface points and using these as interfaces to interconnect a plurality of "reconfigurable lab chip" embodiments of the invention.

Laboratory and Field Instrument Embodiments and Applications

At the next largest physical scale in the spectrum depicted in FIG. 31 are laboratory- and field-reconfigurable instruments 3104. These may be made by employing the reconfigurable "Lab-on-a-Chip" technology described above, or by applying the methods and systems of the invention directly to larger scales of fabrication and/or existing chemical system elements of larger physical size, such as those found in contemporary desktop HPLC technology. The valve technologies readily applicable to this scale have been available for many years from manufactures such as:

Asco Scientific (Angar), 50-60 Hanover Road, Florham Park, N.J. 07932;

Parker Hannifin, 6035 Parkland Boulevard, Cleveland, Ohio 44124;

Valco Instrument Company, Inc. (VICI), 7806 Bobbitt, Houston, Tex. 77055 as well as others. Applying the described systems and methods adds vast potential for increased generality and functionality to these now essential lab bench and field operated technologies that include devices such as liquid and gas chromatography systems, qualitative and quantitative analysis systems, pathogen detectors, DNA sequencing and assay systems, etc.

Laboratory Automation Overlay Embodiments and Applications

At the next largest physical scale in the spectrum depicted in FIG. 31 are applications involving automation of conventional chemical laboratory glassware and related technology 3105. Actuators for conventional chemical laboratory glassware and associated use in expanding the role of general laboratory automation are addressed in a co-pending U.S. Patent application. In some situations, the methods and systems of the present disclosure may be utilized in moderate-scale to large-scale set-ups of conventional chemical laboratory glassware and related technology.

Applying the described systems and methods allows for families of related experiments or productions to be automated, in many cases resulting in faster, less repetitive and less laborious laboratory operations. Additionally, applying such systems and methods to medium- to large-scale set-ups of conventional chemical laboratory glassware and related technology allows for emulation and design work for processes of smaller (e.g., laboratory instruments, field instruments, and "Lab-on-a-Chip" systems) and larger (e.g., chemical plant) physical scales.

Figure 35B:
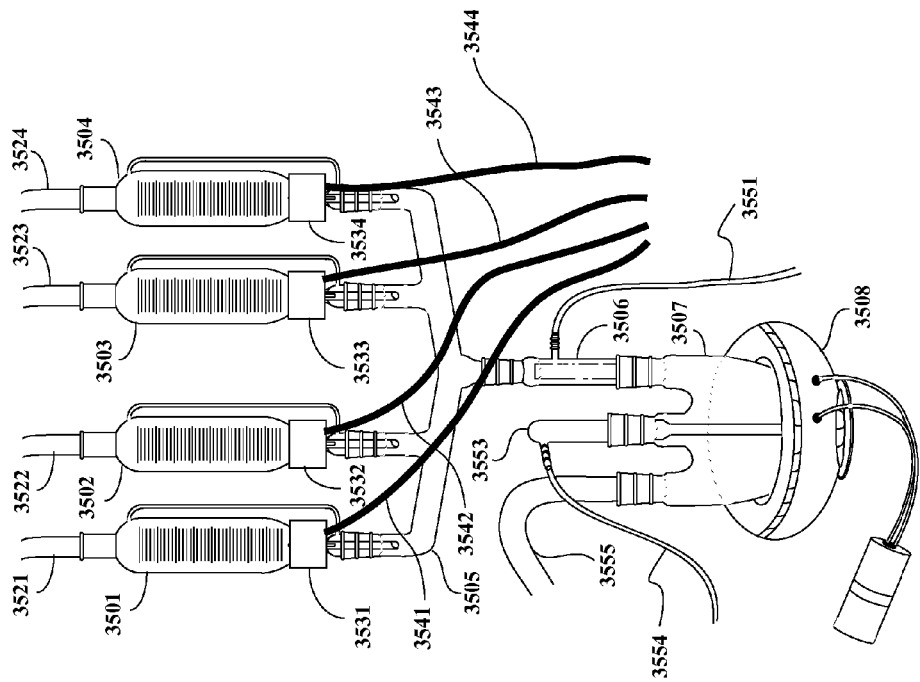
FIGS. 35a-35f depicts a laboratory setup comprising an arrangement of standard conventional chemical laboratory glassware items and related technology.
Figure 35A:
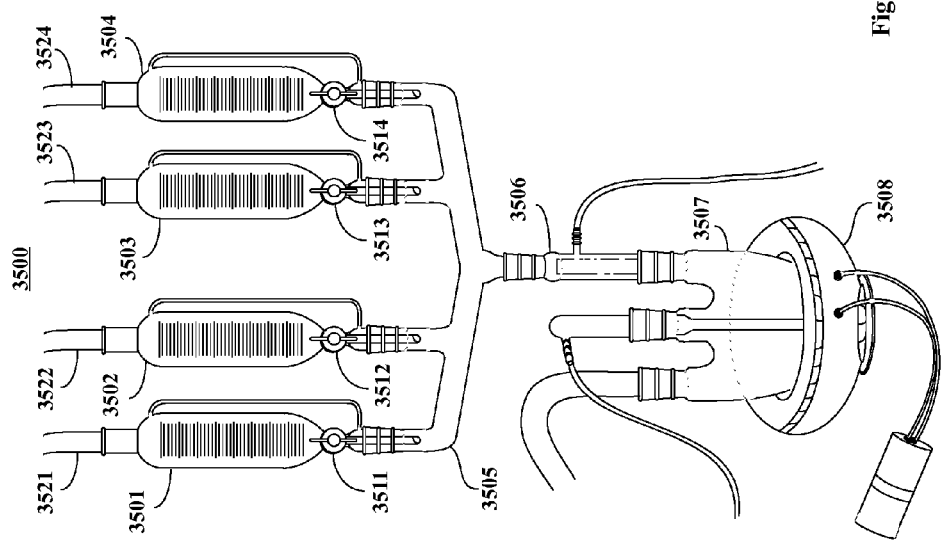

As an illustration of how to apply these methods and systems, FIG. 35a depicts a laboratory setup comprising an arrangement of standard conventional chemical laboratory glassware items (shown connected via mating tapered ground glass "quick-fit" joints) and related technology (tubing connections to external vacuum pumps and gas supplies, an electric heating mantle, undepicted support stands and clamps, etc.). The glassware in this arrangement comprises four pressure-equalizing addition funnels 3501-3504 that each further comprise a corresponding ground glass or Teflon rotating valve ("stopcock") 3511-3514. Each of the four addition funnels 3501-3504 is shown fed by an external source through corresponding inlet tubes 3521-3524 from other parts of a larger set-up, but could also be pre-filled by a human user and sealed with a ground glass or Teflon stopper. The four addition funnels 3501-3504 are arranged to empty into a multiple-inlet ground-glass "quick-fit" glass manifold 3505 that connects through a vacuum adapter 3506 to one of three ground-glass "quick-fit" inlets to a three-neck flask 3507 which is warmed by an electric heating mantle 3508.

FIG. 35b depicts a variation of the arrangement 3500 wherein the four addition funnels 3501-3504 are supplemented by rotating servomotor actuators 3531-3534, each comprising a combined stepper-motor and rotation-angle-sensor unit that is electrically connected to remote controlling equipment via corresponding electric cables 3541-3544. Although specialized actuator units could be fabricated, inexpensive combined stepper-motor and rotation-angle-sensor units and multiple-channel programmable controllers for them are available from numerous manufacturers including Parallax, Inc., 599 Menlo Drive, Suite 100, Rocklin Calif. 95765 which manufactures such devices primarily for hobbyist robotics projects. (The combined stepper-motor and rotation-angle-sensor units themselves comprise a standardized electrical interface provided by numerous manufacturers of radio-controlled airplanes for hobbyists).

Figure 35C:
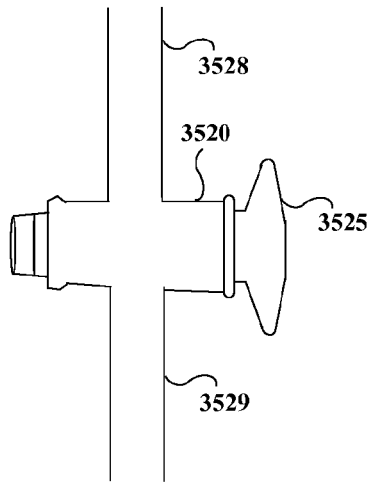
Figure 35D:
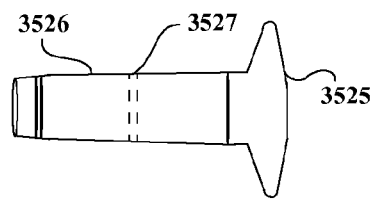
Figure 35E:
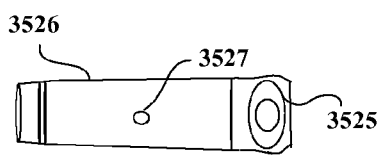

In physically attaching the electrically controlled rotational actuators to the conventional stopcock valve body and handles 3511-3514, the actuator units must be adequately secured and the rotational shaft must be operatively linked to the stopcock valve handles 3511-3514 so the rotation angles can be controlled. FIG. 35c depicts the side view of the body of a conventional stopcock 3520, connecting glass tubes 3528, 3529, and the protruding stopcock valve handle 3525 whose shape makes it easy to grip for precisely-controlled hand operation. FIGS. 35d and 35e depict two orthogonal views of the rotating stopcock component, usually fabricated from glass or Teflon and comprising a shaft 3526 crafted with a through-hole 3527.

Figure 35F:
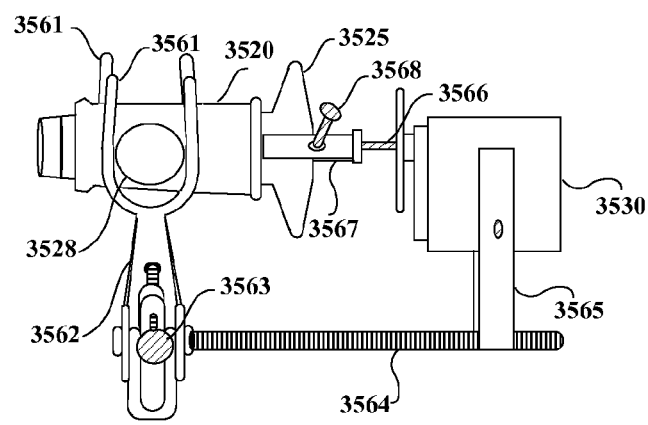

In FIG. 35d, the through-hole 3527 path through the shaft 3526 of the rotating stopcock component is represented by dashed lines, while FIG. 35e depicts a frontal view of the through-hole 3527. In general the through-hole 3527 has a relatively small diameter, making it imperative that the actuator units be adequately secured and the rotational shaft operatively linked to the stopcock valve handle to obtain reliable repeatability of opening and closing operations. The degree of accuracy can be relaxed somewhat by enlarging the diameter of the through-hole 3527 (which is more readily done with a Teflon stopcock shaft 3526 than a glass stopcock shaft). However, with adequate clamping friction and minimal rotationally elastic torsion in the mounting and clamping mechanisms, there would be no need for such enlargement the diameter of the through-hole 3527. FIG. 35f illustrates one approach to attaching an actuator 3530 to the stopcock valve handle 3525 in such a manner. The stopcock body 3520 is grasped by opposing glass-compatible fingers 3561 of a rigid clamping mechanism 3562 comprising at least one conventional tightening set-screw adjustment 3563 for tightening firmly to fit the stopcock body 3520 in order to tightly grip the stopcock body and the connecting glass tubes 3528 (depicted) and 3529 (not depicted). A rigid threaded adjustment rod 3564 attaches at one end to the clamping mechanism 3562 and at the other end to a rigid support bracket 3565 (here shown in exaggerated proportion for the sake of clarity) for the actuator unit 3530, or in some other fashion directly to the actuator housing. The rotating shaft 3566 of the actuator 3530 attaches to a clamp element 3567 (here shown in diminished proportion for the sake of clarity) that envelopes the stopcock valve handle 3525; in some embodiments the valve handle clamp element 3567 may employ a tightening set-screw 3568. Additional support may be provided by these and/or other clamps and support rod arrangements that secure the various glassware elements depicted in FIG. 35*b*. This is an exemplary approach to the precision attachment of a rotational actuator to a conventional stopcock handle, including ones that may be made from glass. If Teflon rotating stopcock elements are used, the rotating shaft of the actuator may be more directly attached to the stopcock handle through the use of drilled holes and/or penetrating fasteners. Many other arrangements are possible as will be clear to one skilled in the art.

The resulting four electrically-controlled additional funnels 3501-3504 depicted in FIG. 35*b*, together with the multiple-inlet glass manifold 3505, form a multi-port selection valve as employed in various methods and systems disclosed herein. This connects to the vacuum adapter 3506 which, via the flexible connecting tubing 3551 which in turn connects to a manifold of valves (not depicted) dispensing vacuum, clearing gas, solvent, and a potentially different drying gas. The vacuum adapter 3506 can be used to:

Equalize the pressure for entering chemical species from the multiple-inlet glass manifold 3505;

Seal or subsidize the pressure during a subsequent distillation phase so that heated vapors in the flask 3507 may be directed through the angled pre-distillation outlet glass tube 3555;

Later force out nearly all the reacted and post-distilled remnant fluid contents from the flask 3507 at the completion of the procedure by applying a pressured clearing gas (and potentially help make any temperature changes needed prior to the subsequent introduction of the cleaning solvent);

Introduce said cleaning solvent to an adequate fill line in the flask;

Force out nearly all the cleaning solvent contents from the flask 3507 by applying pressured clearing gas or potentially an alternate drying gas;

Continue applying said gas until all solvent has evaporated, potentially thermally assisted by appropriate operation of the heating mantle 3508;

Potentially continue applying said gas to make any temperature changes needed prior to the subsequent introduction of chemical species for a subsequent chemical process.

The result is an embodiment applied to an arrangement of standard conventional chemical laboratory glassware items and related technology to create a reconfigurable reusable chemical processing system for use in producing a variety of chemical products. Further, the relatively small degree of reconfigurability of the arrangement of FIG. 35*b* can be considerably magnified by additional undepicted controllable arrangements. Some examples include:

One or more of the inlets to the multiple-inlet glass manifold 3505 may be fitted with provisions for introducing cleaning solvent so as to reduce contamination between processes;

Undepicted distilling apparatus connected to the distillation outlet tube 3555 may have electrically controlled outflow routing and separate cleaning solvent introduction provisions and gas recovery provisions. With this, the arrangement of FIG. 35*b* can be used to support a wider range of processes and products:

In some situations supported by a first combination of chemical species applied from the electrically-controlled addition funnels 3501-3504, the desired product may be the condensed vapors emerging from the distillation outlet tube 3555 resulting from heating of the flask 3507 via the heating mantle 3508.

In other situations resulting from a second combination of chemical species applied from the electrically-controlled addition funnels 3501-3504, the desired product may be a gas emitted through and recovered from distillation outlet tube 3555 where no heating, or a much lower heating temperature, is required.

In other situations resulting from a third combination of chemical species applied from the electrically-controlled addition funnels 3501-3504, the desired product may be the post-distilled remnant fluid contents from the flask 3507 at the completion of the procedure;

In other situations resulting from a fourth combination of chemical species applied from the electrically-controlled addition funnels 3501-3504, the desired product may be one or more of:

Gas initially emitted when chemical species are combined;

Condensed vapors emerging from the distillation outlet tube 3555 resulting from heating of the flask 3507;

The post-distilled remnant fluid contents from the flask 3507 at the completion of the procedure.

In other situations resulting from a fifth combination of chemical species applied from the electrically-controlled addition funnels 3501-3504, only a subset of the fifth combination of chemical species may be initially combined, heating may be applied to boil off the resultant reaction product, and then at least one more chemical species of the fifth combination of chemical species is then added;

The inlets tubes 3521-3524 to addition funnels 3501-3504 may themselves be fed by reconfigurable arrangements not unlike that depicted in or described in relation to that of FIG. 35*b*.

One skilled in the art will understand that this example is illustrative and that the illustrated methods and principles thus readily apply to a wide range of arrangements of conventional chemical laboratory glassware and related technology.

Chemical Plant Applications

At the largest two physical scales considered in the spectrum depicted in FIG. 31 are applications directed to small-scale chemical manufacturing 3106 and large-scale chemical production plants 3107. As the economies of chemical production plants and the chemical substances marketplace continue to evolve, there is considerable opportunity for the perfection and incorporation of flexible reconfigurable chemical systems. Some of the benefits of applying the disclosed methods and systems include the following:

- By broadening the range of production possible for a particular set of facilities within a chemical production plant to support a wide range of chemical reaction environments under full or partially automated operation and reorganization, vast improvements in production efficiency can be obtained. This can be exploited to improve the operation of the plant with reduced operating costs and faster responses to opportunities in the marketplace.
- The reconfigurability of a chemical production plant embodiment can be made to include join-and-segregate capabilities so that facilities can be readily ganged or parallelized as needed depending on the details of the processes to be scheduled.
- Such reconfigurability of a chemical production plant embodiment can further provide short-term facility configuration support for multi-product output as may be advantageous for part of a production cycle, and later allow the otherwise subsequently unused facilities to be used profitably for other chemical production activities.
- The clearing/cleaning/drying provisions provided for by the invention can be incorporated into the reconfigurable facilities and shared across many types of production processes. This can aid in the reduction of waste, pollution, and staff exposures as well as improve the economics of today's marginally profitable processes.

While the invention has been described in detail with reference to disclosed embodiments, various modifications within the scope of the invention will be apparent to those of ordinary skill in this technological field without departing from the spirit or scope of the invention. It is to be appreciated that features described with respect to one embodiment typically may be applied to other embodiments. It is intended that the specification and examples be considered as exemplary only, with the true scope and spirit of the invention being indicated by the following claims.

What is claimed is:

1. A software-reconfigurable, computer-controlled chemical processing apparatus, the apparatus comprising:
    a control system executing configuration and process operation software;
    a plurality of chemical laboratory glassware elements each element comprising at least one chemical interface port;
    a plurality of glass chemical transport elements, each transport element connected to at least one of the chemical laboratory glassware elements; and
    a plurality of electrically-controlled glass stopcock valves comprising glass stopcock valve bodies and associated rotating shaft for rotation within each associated glass stopcock valve body, the associated rotating shaft mechanically coupled to a rotating servomotor actuator, the rotating servomotor actuator comprising a stepper-motor and rotation-angle-sensor unit, the rotating servomotor actuator electrically connected to the control system;
    wherein the electrically-controlled glass stopcock valves and the glass chemical transport elements are arranged to form a chemical interconnection network that connects the plurality of the chemical laboratory glassware elements for processing of chemicals; and
    wherein the apparatus is reconfigurable under the control of the configuration and process software; and
    wherein the control system attains one of a plurality of distinct configurations by reconfiguring the chemical interconnection network.

2. The apparatus of claim 1 wherein the configuration and process operation software comprises software for controlling cleaning of the glassware elements, chemical transport elements, and stopcock valves with solvents.

3. The apparatus of claim 1 wherein the configuration and process operation software comprises software for controlling clearing the glassware elements, transport elements, and stopcock valves with a clearing gas.

4. The apparatus of claim 1 wherein the configuration and process operation software comprises software for controlling drying of the glassware elements, transport elements, and stopcock valves with a drying gas.

5. The apparatus of claim 1 wherein the configuration and process operation software allocates glassware elements, transport elements, and stopcock valves by executing software algorithms.

6. The apparatus of claim 1 wherein the configuration and process operation software simultaneously controls a plurality of independent chemical processes.

7. The apparatus of claim 1 wherein the configuration and process operation software controls chemical processing in real-time.

8. The apparatus of claim 1 wherein the configuration and process operation software configures the chemical interconnection network into one of a plurality of configurations to control the processing of chemicals for a unique application.

9. The apparatus of claim 1 wherein the glassware elements, transport elements, and stopcock valves comprise quick-fit glassware joints.

10. The apparatus of claim 1 wherein the control system comprises at least one digital computer.

11. The apparatus of claim 1 wherein the control system further comprises a plurality of processors arranged in a multi-level control system.

12. The apparatus of claim 3 wherein the clearing of the glassware elements, transport elements, and stopcock valves is performed without disassembly.

13. The apparatus of claim 2 wherein the cleaning of the glassware elements, transport elements, and stopcock valves is performed without disassembly.

14. A flexible, reconfigurable, reusable laboratory apparatus comprising:
    a control system executing configuration and process operation software;
    a plurality of laboratory chemical glassware elements;
    a plurality of laboratory chemical glassware transport elements;
    a plurality of servo-controlled glass stopcock valves comprising glass stopcock valve bodies and associated rotating shaft for rotation within each associated glass stopcock valve body, the associated rotating shaft mechanically coupled to a rotating servomotor actuator, the rotating servomotor actuator comprising a stepper-motor and rotation-angle-sensor unit, the rotating servomotor actuator electrically connected to the control system;
    wherein the plurality of chemical glassware elements, the plurality of laboratory transport elements, and the plurality of servo-controlled glass stopcock valves are connected together to form a chemical interconnection network and wherein the control system operates the servo-controlled valves to select at least one chemical path within the interconnection network to perform at least one chemical process from a plurality of chemical processes.

15. The apparatus of claim 14 wherein the apparatus is used for chemical analysis.

16. The apparatus of claim 14 wherein the apparatus is used for chemical synthesis.

17. The apparatus of claim 14 wherein the apparatus is used for small-scale chemical manufacturing.

18. The apparatus of claim 14 wherein the configuration and process operation software controls chemical processing.

19. The apparatus of claim 14 wherein the configuration and process operation software simultaneously controls a plurality of independent chemical processes.

20. The apparatus of claim 14 wherein the control system further comprises a plurality of processors arranged in a multi-level control system.

* * * * *